United States Patent [19]
Culp et al.

[11] Patent Number: 6,017,354
[45] Date of Patent: *Jan. 25, 2000

[54] INTEGRATED SYSTEM FOR POWERED SURGICAL TOOLS

[75] Inventors: Jerry A. Culp, Oshtemo Twp., Kalamazoo County; Kevin J. Schemansky, Farmington Hills; David E. Monk, Portage, all of Mich.

[73] Assignee: Stryker Corporation, Kalamazoo, Mich.

[ * ] Notice: This patent issued on a continued prosecution application filed under 37 CFR 1.53(d), and is subject to the twenty year patent term provisions of 35 U.S.C. 154(a)(2).

[21] Appl. No.: 08/689,866

[22] Filed: Aug. 15, 1996

[51] Int. Cl.[7] .................................................. A61B 17/00
[52] U.S. Cl. .............................................. 606/170; 604/22
[58] Field of Search ...................................... 606/167, 170, 606/180; 604/22; 318/432, 799, 806

[56] References Cited

U.S. PATENT DOCUMENTS

| | | |
|---|---|---|
| 4,552,143 | 11/1985 | Lottick . |
| 4,705,038 | 11/1987 | Sjostrom et al. . |
| 4,897,789 | 1/1990 | King et al. . |
| 5,017,059 | 5/1991 | Davis . |
| 5,162,725 | 11/1992 | Hodson et al. . |
| 5,300,926 | 4/1994 | Stoeckl . |
| 5,304,763 | 4/1994 | Ellman et al. . |
| 5,383,874 | 1/1995 | Jackson et al. . |
| 5,391,144 | 2/1995 | Sakurai et al. . |
| 5,400,267 | 3/1995 | Denen et al. . |
| 5,433,702 | 7/1995 | Zelman et al. . |
| 5,543,695 | 8/1996 | Culp et al. . |
| 5,601,583 | 2/1997 | Donahue et al. ......................... 606/170 |
| 5,609,560 | 3/1997 | Ichikawa et al. . |
| 5,632,759 | 5/1997 | Rexroth .................................... 606/170 |

FOREIGN PATENT DOCUMENTS

| | | |
|---|---|---|
| 0 304 574 | 3/1989 | European Pat. Off. . |
| 0 329 944 | 8/1989 | European Pat. Off. . |
| 2 517 955 | 6/1983 | France . |
| 39 23 024 | 2/1990 | Germany . |
| 40 40 537 | 8/1991 | Germany . |
| WO 89/05613 | 6/1989 | WIPO . |
| WO 94/10931 | 4/1994 | WIPO . |
| WO 94/10921 | 5/1994 | WIPO . |

OTHER PUBLICATIONS

*The 65K Neuro System*, The Anspach Effort, Inc., Title page, 4 pages.

*The MicroChoice™ Electric Powered Surgical System*, 1996, Title page, 3 pages.

*The Hall Micro E Instruments*, 7 pages.

*Surgical Systems*, Aseptico, 1993, Title page, 7 pages.

The Series 2000 Modular Instrument System, MicroAire 1992, Title page, 7 pages.

PCT Application No. PCT/US97/15242, International Preliminary Examination Report, Nov., 1998.

Primary Examiner—Michael Buiz
Assistant Examiner—William Lewis
Attorney, Agent, or Firm—Flynn, Thiel, Boutell & Tanis, P.C.

[57] ABSTRACT

An integrated surgical tool system (30) for energizing different powered surgical handpieces (32, 33). Internal to each handpiece is a non-volatile memory (72) which stores data regarding the operating parameters of the handpiece. This data, includes information about the speeds at which any motor internal to the handpiece should be driven, the maximum current that should be drawn by the handpiece and the maximum internal temperature of the handpiece. The handpiece is plugged into a complementary control console (36). The control console reads the data in the internal memory. Based on the retrieved data and manual control signals, the control console supplies energization signals to the handpiece so as to cause the appropriate actuation of the handpiece.

37 Claims, 34 Drawing Sheets

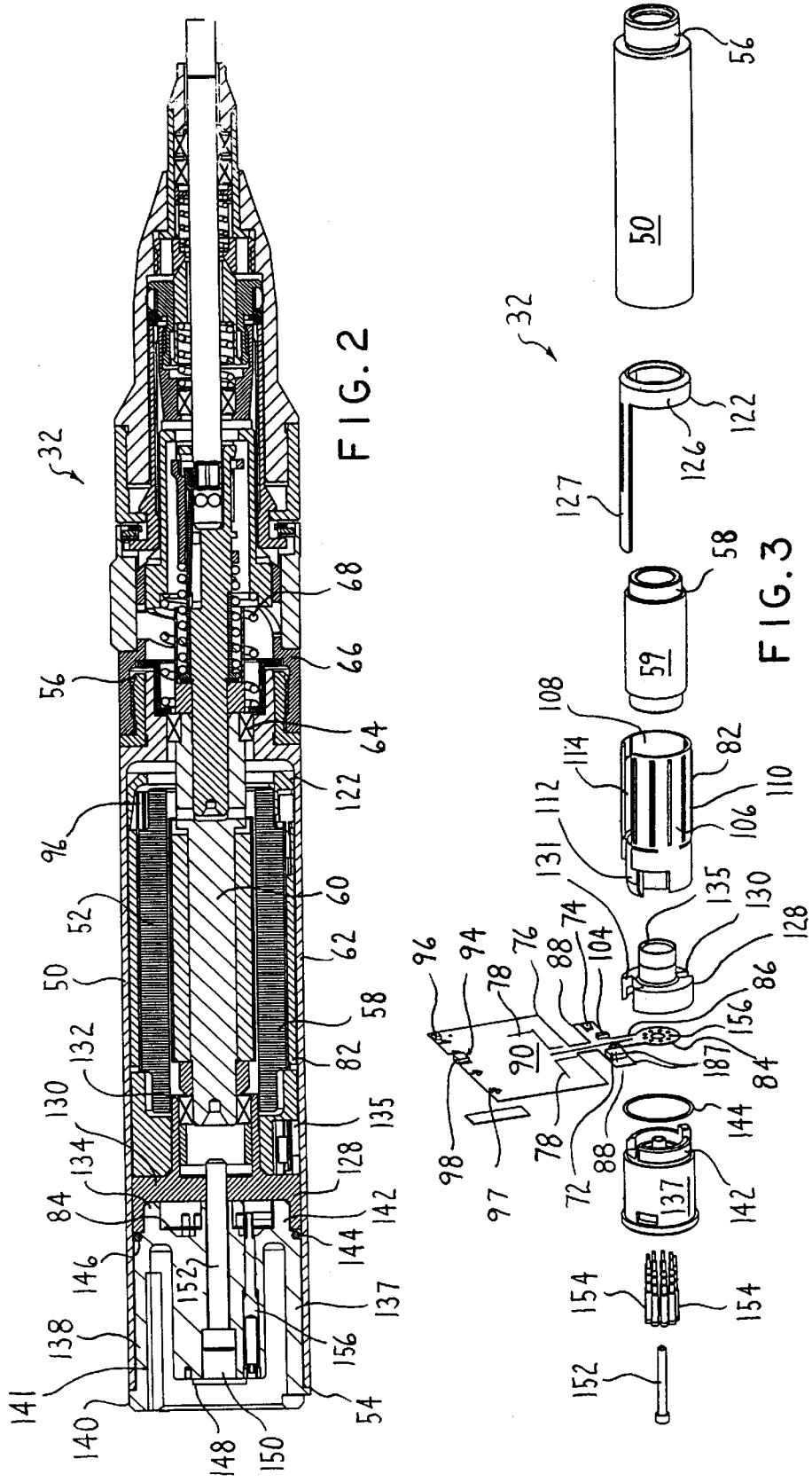

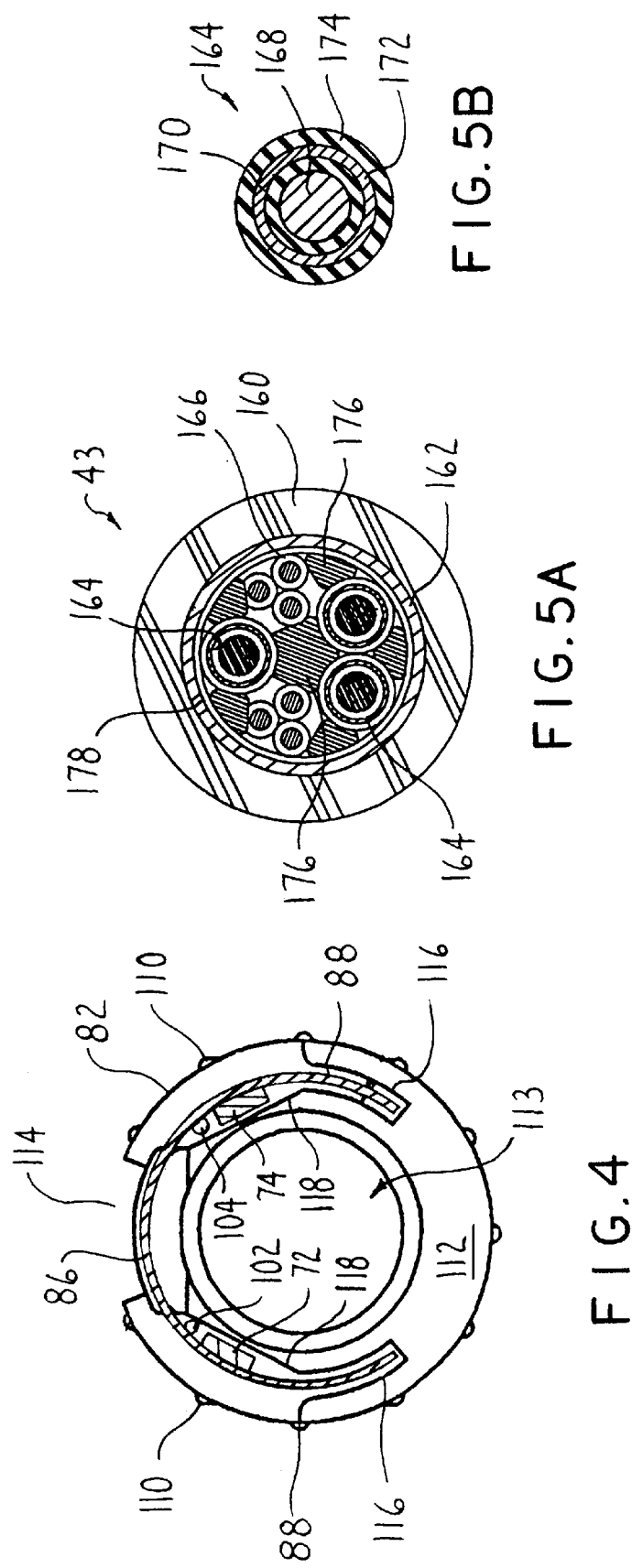

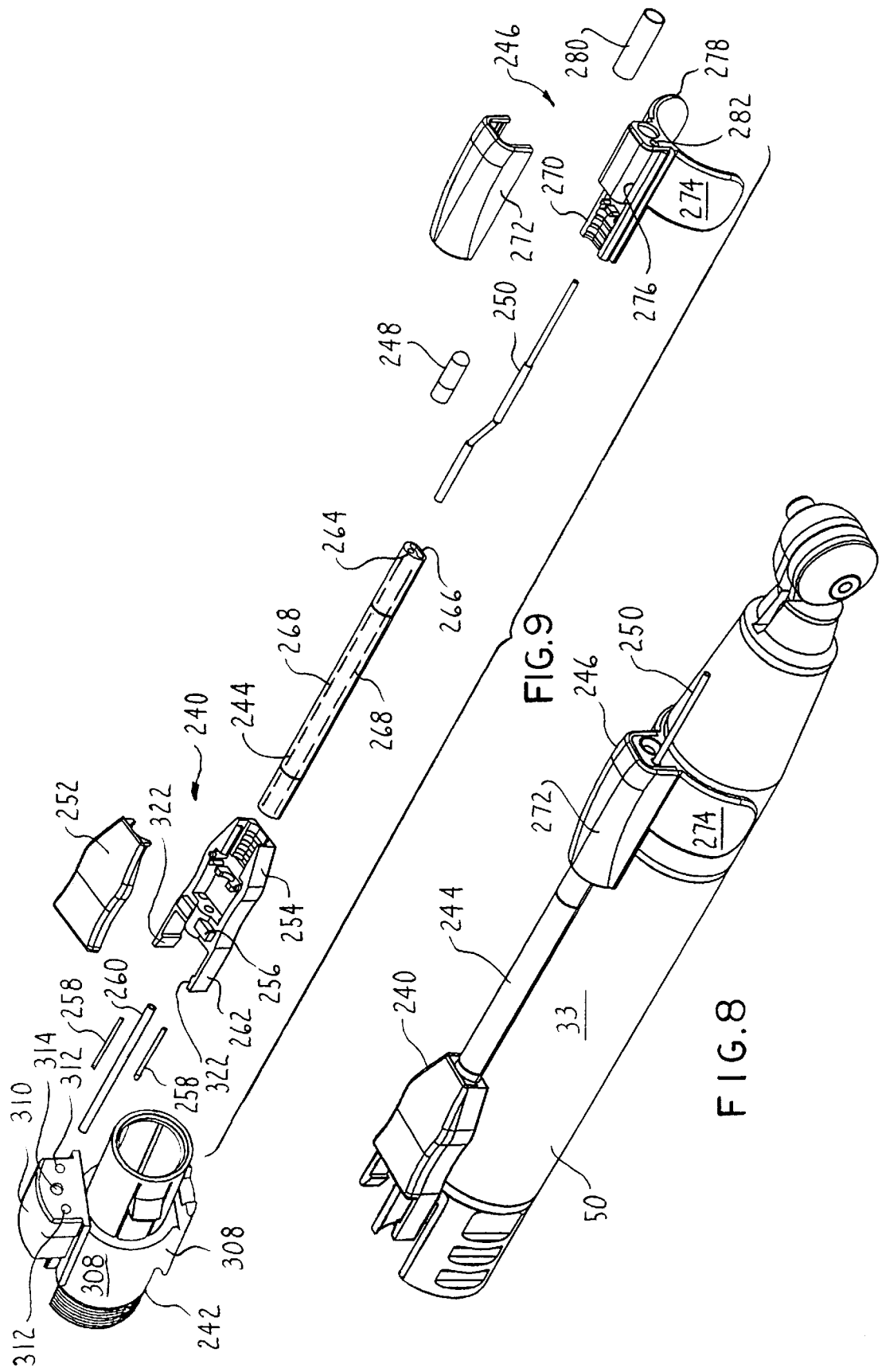

FIG. 13

| | | | 72 |
|---|---|---|---|
| HEADER 342 | DEVICE B FRST SGNL LVL 364 | MTR OSC SPD MIN 391 | SPD CNTRL COEF 420 |
| H.P. I.D. 343 | DEVICE B SCND SGNL LVL 366 | MTR OSC SPD MAX 392 | SPD CNTRL COEF 422 |
| H.P. I.D. 344 | DEVICE B THRD SGNL LVL 368 | MTR GEAR RATIO 394 | TRQU/SPD S.P. 428 |
| H.P. I.D. 345 | DEVICE B FILTER 370 | MOTOR POLES 396 | TRQU/SPD S.P. 430 |
| CODE REVISION 346 | DEVICE A COEF "a" 372 | MIN BIAS CURR 398 | TRQU/SPD S.P. 432 |
| CHECK SUM 347 | DEVICE A COEF "b" 374 | MAX BIAS CURR 400 | ZERO SPD TRQU 434 |
| TABLE LENGTH 348 | DEVICE A COEF "c" 376 | MAX RST CURR 402 | RST/END DLY PULSE 442 |
| H.P. DEF 350 | DEVICE B COEF "a" 378 | MAX ENBL CURR 403 | BRAKE PULSE 444 |
| DEVICE A TYPE 352 | DEVICE B COEF "b" 380 | MAX T.F.A. CURR 404 | CURRENT FILTER 446 |
| DEVICE B TYPE 354 | DEVICE B COEF "c" 382 | CURR/TORQ COEF 406 | TACH. FILTER 448 |
| DEVICE A FRST SGNL LVL 356 | MOTOR STALL SPEED 384 | CURR/TORQ COEF 408 | TIMEOUT 449 |
| DEVICE A SCND SGNL LVL 358 | MTR MIN SET SPD 386 | CURR/TORQ COEF 410 | RES-COMP 450 |
| DEVICE A THRD SGNL LVL 360 | MTR MAX SPD 388 | CURR/CNTRL COEF 412 | WARM RUN 451 |
| DEVICE A FILTER 362 | MTR SET SPD INC 390 | CURR/CNTRL COEF 414 | HIGH CURR 452 |
| | | CURR/CNTRL COEF 416 | PUMP 453 |
| | | SPD CNTRL COEF 418 | LT & WTR 454 |
| | | | SCREEN TYPE 458 |
| | | | CUSTOM SCREEN 460 |

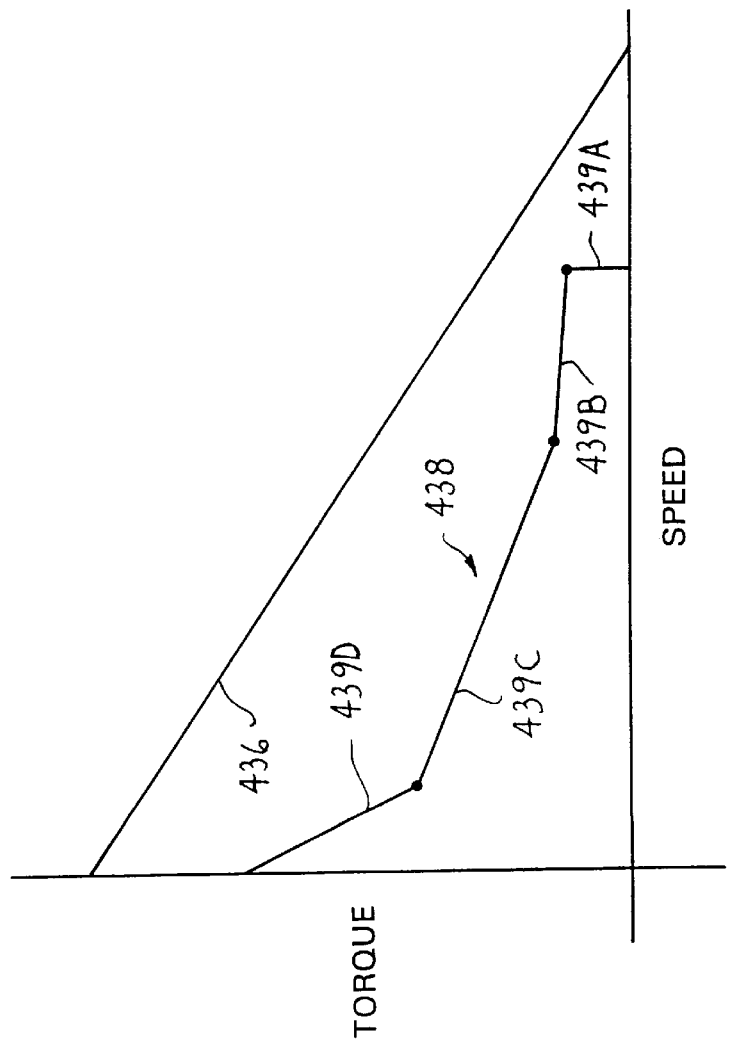

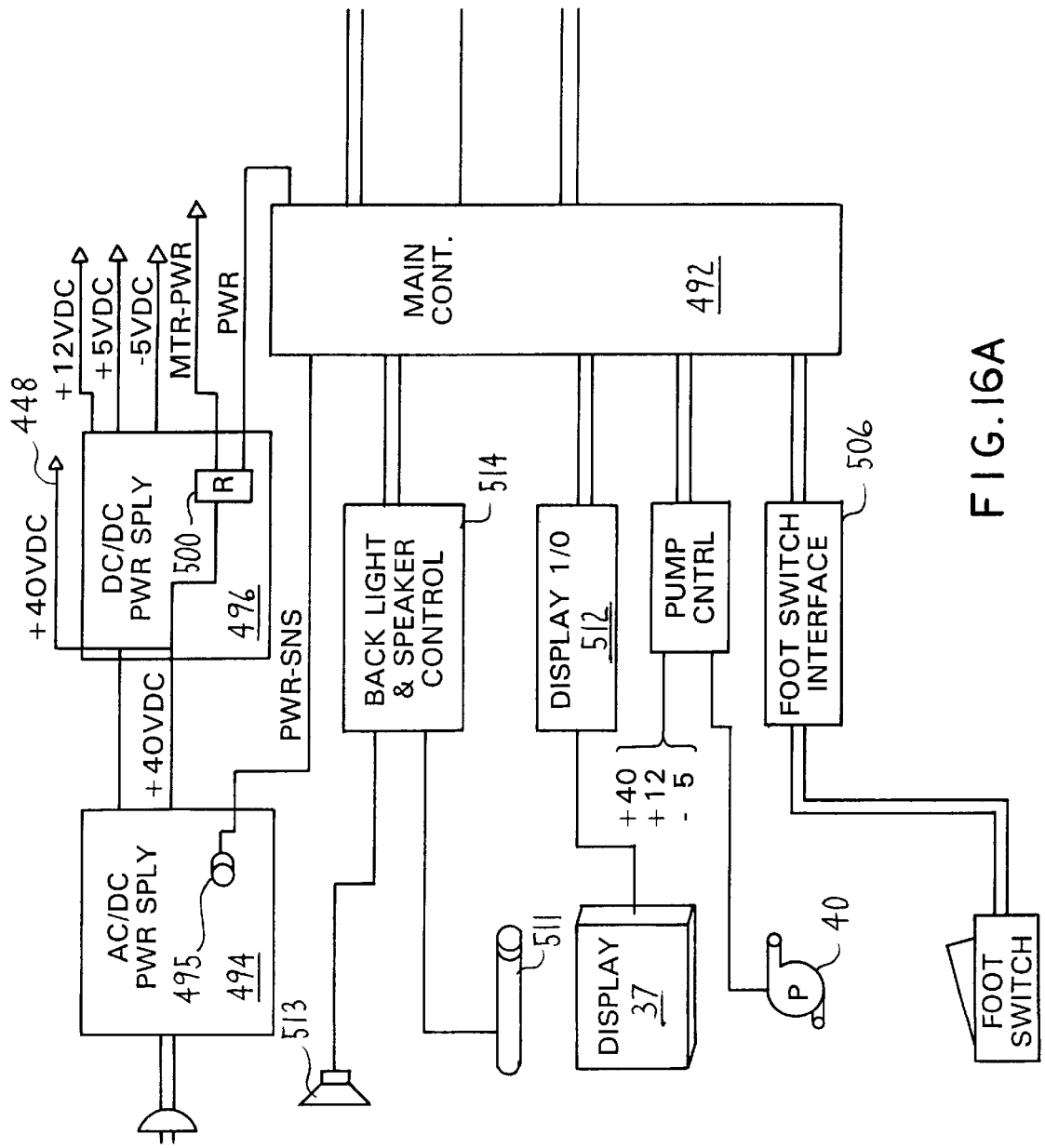

NO HANDPIECE DETECTED they are not without their own disadvantages. Many of
these consoles are arranged so that the medical personnel
have to manually preset their internal electronics in order to
ensure that they be provided the desired energization signals
to the tools to which they are connected. Moreover, given
the inevitable human error factor, time also needs to be spent
to ensure that once configured for a new tool, a console is,
in fact, properly configured. Requiring medical personnel to
perform these tasks takes away from the time the personnel
could be attending to the needs of the patient.

INTEGRATED SYSTEM FOR POWERED SURGICAL TOOLS

FIELD OF THE INVENTION

This invention relates generally to powered surgical tools and, more particularly, to an integrated system for facilitating the use of a number of different surgical tools and the use of these tools with different accessories.

BACKGROUND OF THE INVENTION

In modern surgery, powered surgical tools are some of the most important: instruments medical personnel have available to then for performing certain surgical procedures. Many surgical tools take the form of some type of motorized handpiece to which a cutting accessory like a drill bit, a burr or a saw blade are attached. These tools are used to selectively remove small sections of hard or soft tissue or to separate sections of tissue. The ability to use powered surgical tools on a patient has lessened the physical strain of physicians and other personnel when performing surgical procedures on a patient. Moreover, most surgical procedures can be performed more quickly and more accurately with powered surgical tools than with the manual equivalents that proceeded them.

A typical powered surgical tool system, in addition to the handpiece, includes a control console and a cable that connects the handpiece to the console. The control console contains the electronic circuitry that converts the available line voltage into energization voltage suitable for powering the motor integral with the handpiece. Typically, the control console is connected to receive a signal from the hand or foot switch used to control the tool; based on that signal, the console sends appropriate energization signals to the handpiece so as to cause it to operate at the desired speed.

As the use of powered surgical tools has expanded, so has the development of different kinds of powered surgical tools that perform different surgical tasks. For example, a femoral reamer, used in hip replacement surgery is a relatively slow speed drill that operates at approximately 100 RPM, yet it draws a relatively high amount of power, approximately 400 Watts. Neurosurgery requires the use of a craniotome which is a very high powered drill that operates at approximately 75,000 RPM and that requires a medium amount of power, approximately 150 Watts. In ear, nose and throat surgery, micro drills are often employed. A typical micro drill rotates between approximately 10,000 and 40,000 RPM and requires only a relatively small amount of power, approximately 40 Watts.

As the number of different types of powered surgical tools have expanded, it has become necessary to provide each type of handpiece a mechanism for ensuring that it receives the appropriate energization signals. The conventional solution to this problem has been to provide each handpiece with its own power console. As can readily be understood, this solution is expensive in that it requires hospitals and other surgical facilities to keep a number of different consoles available, in the event a specific set of tools are required to perform a given surgical procedure. Moreover, in the event a number of different surgical tools are required in order to perform a given surgical procedure, it is necessary to provide the operating suite with the individual consoles required by the different handpieces. Having to provide these different consoles contributes to clutter in the operating suite.

An attempt to resolve this issue has been to design consoles that can be used to supply power to different handpieces. While these consoles have performed satisfactorily There have been some attempts to provide surgical tools capable of providing some configuration information to the complementary control consoles. These tools typically take the form of handpieces with one or two resistors that collectively provide one or more analog signals back to the console. The console, based on the magnitude of these analog tool type signals, is capable of performing some basic tool configuration functions such as, identify the type of the tool or cutting instrument attached thereto. While these powered tool systems have proved useful, they are of limited value in that any significant information about the tool, such as an indication of the maximum power that can be applied thereto, or the maximum speed at which its motor can be driven must be contained within the complementary console. In order for a console to properly configure itself for use with a particular handpiece, the console must be preloaded with this data. If the console does not contain this data, the recognition data contained within the tool is of relatively marginal value.

Moreover, as the number of powered surgical tools has expanded, so has the number of accessory features that can be used with the tools. Some tools, for example are provided with hand switches integral with the tool that allow the physician to control the on/off state of the tools as well as the speed of the motor internal to the tool. Still other tool systems are provided with foot switches. This later type of control arrangement is provided for the convenience of medical personnel who, instead of controlling tool speed with their hands, prefer controlling tool speed with their feet. One reason some foot switch tool control assemblies are preferred is that it eliminates the need have a hand switch, which is a physical object that some physicians find interferes with their grasp of the handpiece.

Still other powered surgical tool systems are provided with integrated light and/or water sources. The light source typically includes some type of light emitting member attached to the head of the surgical tool. The light source is provided in the event the surgeon requires a high intensity light to be directed onto the surgical site where a surgical task is being performed. The water source is typically connected to an irrigation pump. A water source is typically attached to a surgical tool in situations where it. is desirable that the surgical site be irrigated essentially simultaneously with the execution of the surgical task.

The conventional solution to providing surgical tools with the desired accessories has been to design individual tools their own fixed accessories. Some tools, for example, are provided with hand switches while other tools do not include these switches. Similarly, some tools are provided with integral conduits for supplying light and/or water to the surgical site while other tools do not include these attachments. In a surgical facility, the choice of surgical tool can be a function of variables such as physician preference and the type of surgical task being performed. It can be quite costly to provide a number of different tools, each with its own set of accessory features, in order to make appropriate accommodation for individual personal preferences and surgical requirements.

Moreover, the tool accessories typically require their own set of control signals to regulate their operation. Often this has been accomplished by providing the accessories, such as the light and water units, with their own control consoles that are separate from the control consoles used to control the application of power to the associated handpieces. The need to provide these additional control consoles further contributes to both the cost of properly equipping an operating suite and the clutter within the suite.

There have been attempts at reducing tool proliferation by providing surgical tools with removable hand switches and removable light and water clips. The hand switches, once removed, reduce some of the structural components that are bothersome to some surgeons. However, these tools are typically provided with some type of permanent holder to secure the hand switch in place. These holders still have the potential of interfering with the grasp of the tools to which they are attached. Moreover, these removable units must still be provided with some type of control unit. In order to maximize the utility of these removable units, as discussed above, they are often provided with their own control consoles. Still another disadvantage of this type of tool assemblies is that their light and water units have complementary control buttons that are depressed in order to control the actuation of these units and their rates of operation. The inclusion of these control buttons further adds to the overall number of control buttons that are presented to the personnel in the surgical suite. The presentation of these buttons, when they are not needed thus presents surgical personnel with extraneous information that may detract their attention from the matters and instrument controls on which they should be concentrating.

Moreover, recently surgical tools have been developed that have different power requirements than conventional handpieces. For example, for some surgical procedures a physician may wish to use a tool that includes a battery pack for applying power. Sometimes, in order to avoid the inevitable problem of the battery drainage, the surgeon may wish to substitute a line-powered power unit for the battery pack. Still other new tools do not even include traditional electrically powered motors. An example of these tools are surgical lasers and ultrasonic scalpels. These tools have their own power requirements and complementary accessories. In order to make these tools available to surgical. personnel, it has been necessary to bring an additional set of control consoles into the surgical suite. Having to provide this additional equipment has further contributed to the cost and complexity of equipping a surgical suite.

SUMMARY OF THE INVENTION

This invention relates to an improved integrated system for powered surgical tools that facilitates the use of tools having different power and control signal requirements and that allows the individual tools to be used with different combinations of accessory units.

BRIEF DESCRIPTION OF THE DRAWINGS

The invention is pointed out with particularity in the claims. The above and further features of the invention may be better understood by reference to the following description taken in conjunction with the accompanying drawings in which:

FIG. 2 is a cross sectional view of one handpiece that can be employed as part of the integrated surgical tool system;

FIG. 3 is an exploded view of the internal components of the handpiece motor;

FIG. 4 is a bottom view illustrating how the flex circuit is housed in a back shell of a handpiece;

FIG. 5A is a cross sectional view of a basic cable used to provide energization signals to a handpiece and that serves as a conduit for control signals exchanged between the handpiece and the control console;

FIG. 5B is a detailed cross sectional view of a single motor conductor within the cable of FIG. 5;

FIG. 8 is an exploded view illustrating how a removable light-and-water clip is attached to a handpiece;

FIG. 9 is an exploded view illustrating the components forming the light-and-water clip of FIG. 8;

FIG. 13 is a block diagram of the data stored in the non-volatile memory within a handpiece;

FIG. 14 is a diagram of illustration how the maximum torque of the motor in the handpiece can vary as a function of the speed of the handpiece;

FIG. 15 is a diagram representative of the data fields within the read/write memory within a handpiece;

FIG. 16 is a blue print indicating how FIGS. 16A and 16B are assembled to form a basic block diagram of the elements forming the control circuit within the console of the integrated tool system;

DETAILED DESCRIPTION

Figure 1:
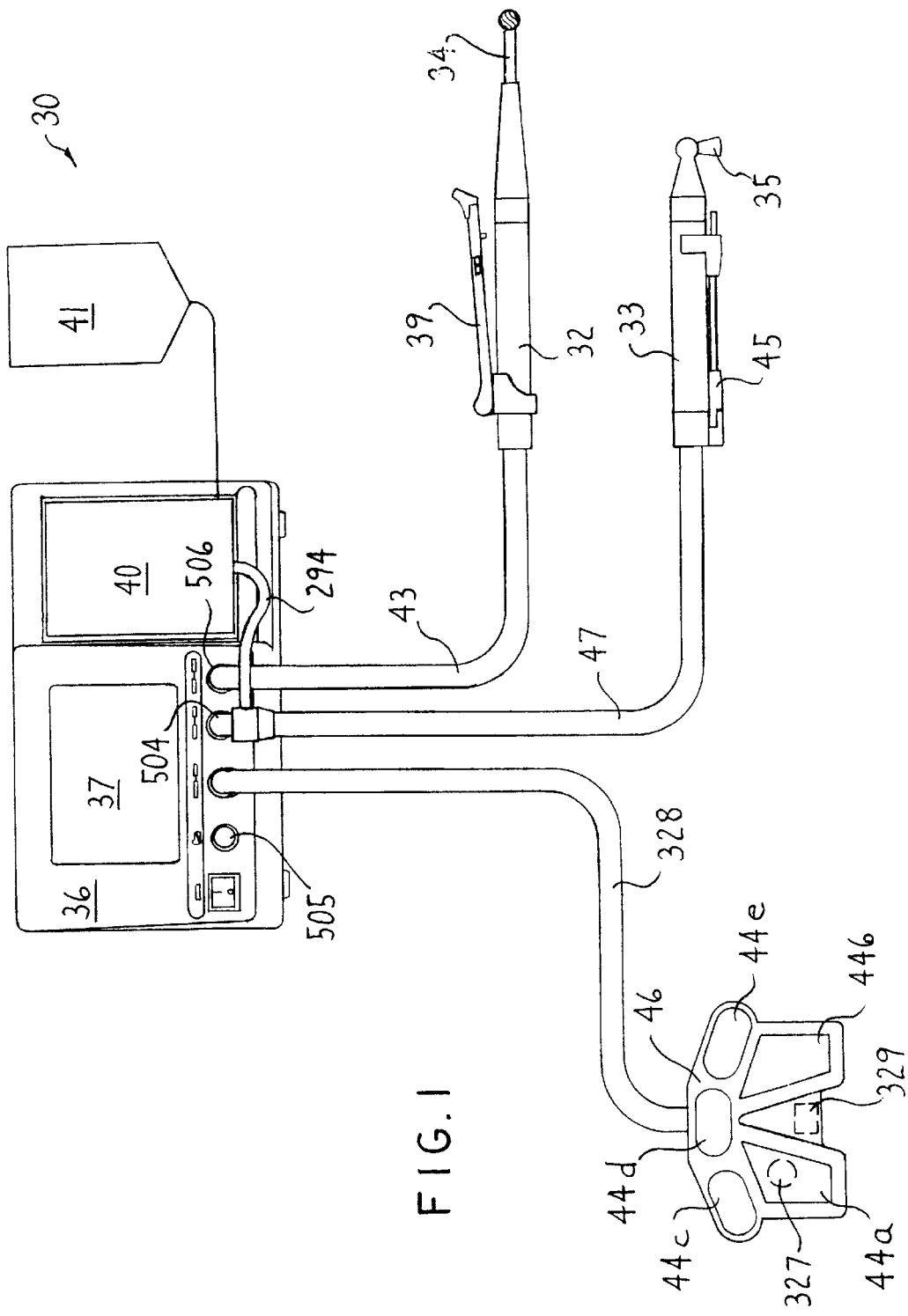
FIG. 1 depicts the basic components of the integrated surgical tool system of this invention.

FIG. 1 depicts the basic components of the integrated surgical tool system 30 of this invention. system 30 includes two surgical tools, referred to as handpieces 32 and 33. Each handpiece 32 and 33 contains an electrically driven motor. A cutting attachment, here a burr 34, is coupled to handpiece 32 so as to rotate with the actuation of the motor. A saw 35 serves as the cutting attachment for handpiece 33. The power for energizing the motor within the handpiece 32 or 33 comes from a control console 36. The control console 36 selectively energizes the handpieces 32 and 33 in response to user-entered commands and further monitors the operation of the handpieces. A touch screen display 37 integral with control console 36 serves as the interface through which information about the handpieces 32 and 33 is presented to surgical personnel and through which some commands used to control the handpieces are supplied to the control console.

The on/off operation and speed of handpiece 32 is controlled by a removable hand switch 39 fitted around the outside of the handipiece. A cable 43 connected between handpiece 32 and control console 36 provide the conductive paths for the signals exchanged between the handpiece and the console. These signals include both the signals generated by the handpiece 32 in response to the state of the hand switch 39 and the energization signals that are applied to the motor internal to the handpiece. Handpiece 33 is not fitted with a hand switch. Instead, the on/off state and motor speed of handpiece 33 are controlled by the depression of pedals 44 integral with a foot switch assembly 46 also part of system 30.

The surgical site to which handpiece 33 is applied is illuminated and selectively irrigated by a light-and-water clip 45 that is removably attached to the handpiece 33. The water that is discharged from light-and-water clip 45 is forced through the clip by a pump 40 that is connected to a source 41 of suitable sterile water. In FIG. 1, pump 40 is depicted as being unit that is removably mountable within control console 36. The water is supplied from pump 40 to the light-and-water clip 45 through a cable 47 that extends from control console 36 and that further includes the conductors over which the signals needed to control the handpiece 33 and the light integral with clip 45 travel. The actuation of the light and the discharge of water through the clip 45 are both regulated by control console 36 based on commands entered through the foot switch assembly 46.

When the system 30 determines that a handpiece 32 or 33 has been plugged into the system, control console 36 reads data stored in memory units internal to the handpiece. Based on the retrieved data, the control console 36 configures itself so that it can supply the appropriately energization signals to handpiece 32 or 33. As part of the initialization process, the control console presents a set of instructions on the display 37 that direct the medical personnel to provide information about any accessories that may be used in conjunction with the handpieces 32 and 33. Once the requisite instructions are received, the control console then regulates the operation of the handpieces 32 and 33 based on the state of the hand switch 39, the pedals 44 and commands entered through the display 37.

FIGS. 2 and 3 depict the basic structure of a handpiece, here handpiece 32, that is part of the system 30 of this invention. Handpiece 32 includes a cylindrical motor housing 50 in which a motor 52 is housed. Motor housing 50 is formed to have an open rear end 54 through which the components forming motor 52 are inserted in the housing. Motor housing 50 is further formed to define a neck 56 at the front end of the housing that has a reduced diameter relative to the main body of the housing. In the depicted version of the invention motor 52 is a brush less, Hapless (sensor less) DC motor. Motor 52 includes three separate windings which are represented by a sleeve-like field coil assembly 58. Integral with field coil assembly 58 is a lamination stack 59 which is located around substantially around the entire outside of the field coil assembly. A rotor 600 is rotatably fitted inside the field coil assembly 54. A set of permanent magnets 62 are secured to the outside of the rotor 56 so as to be located in close proximity to the field coil assembly.

The motor rotor 60 extends out of the neck 56 of the motor housing 50. A bearing assembly 64 fitted in the neck 56 around the rotor 60 holds the rotor steady. A drill housing 66 is fitted around the neck 56 of the motor housing 50 so as to extend around the exposed end of the rotor 56. A coupling assembly 68 is located in the drill housing 60. The coupling assembly, which is not part of this invention, releasable secures the burr 34 or other cutting accessory to the rotor 56 so that the accessory will rotate in unison with the rotor.

Two memory units 72 and 74 are fitted in the motor housing 50 of handpiece 32. A first memory unit, memory unit 72, is a read only memory. In one preferred version of the invention memory unit 72 is a non-volatile random access memory (NOVRAM), a one-time write memory, that has a 2k byte storage capacity. NOVRAM 72 is written to during the manufacture of the handpiece 32 and the data stored therein is retrieved by control console 36 when handpiece 32 is attached to the console. The second memory unit, memory unit 74, is a non-volatile, erasable random access memory. In one preferred version of the invention, memory unit 74 is an electronically erasable programmable read memory (EEPROM) that has a storage capacity of 256 bits. EEPROM 74 is written to by the control console 36 as a result of the use of the handpiece 32. The data contained in EEPROM is both read by control console 36 as part of its initial internal configuration process and is further read when maintenance work is performed on the handpiece 32. In one version of the invention, a DS2505P manufactured by Dallas Semiconductor is employed as the NOVRAM 72 and a DS2430AP from the sane source is used as the EEPROM 74.

The NOVRAM 72 and EEPROM 74 are both attached to a flex circuit 76 that is located in the motor housing 50. The flex circuit 76 is formed from a non-conductive material that will not breakdown when subject to the sterilization environment to which the handpiece 32 is exposed (Saturated steam at 270° F. at 30 psi). One suitable material from which the flex circuit 76 is formed is polyamide like material which is sold by the DuPont Company under the trademark Powerflex AP. Copper traces 78 formed on the flex circuit 76 form the conductive paths both to the memories 72 and 74 and to the other components mounted on or connected to the flex circuit.

The flex circuit 76 is primarily fitted between the lamination stack 59 and a sleeve-like plastic back shell 82 that is fitted around the field coil assembly 58. In the illustrated version of the invention, flex circuit 76 is shaped to have a circular head section 84. As discussed hereinafter, the external electrical connections to the flex circuit 76 are made through the head section 84. An elongated, generally rectangularly shaped spine 86 extends away from the head section 84 of the flex circuit 76. Two aligned arms 88 extend perpendicularly away from the spine 86 a short distance away from the head section 84. NOVRAM 72 is attached to a first one of the arms 88 and EEPROM 74 is attached to the second of the arms 88.

Flex circuit 76 has a rectangularly shaped main body 90 that is centered around the end of the spine 86 and that is spaced away from the arms 88. The main body 90 of flex circuit 76 is the portion of the flex circuit that is located between lamination stack 59 and back shell 82. Carried on the main body 90 of the flex circuit 76 are the conductive traces 78 that provide the electrical connections to the three windings forming field coil assembly 58. In order to facilitate the electrical connections to the windings the end of the main body 90 distal from the head section is formed with three arrow head shaped cutouts 97 to which traces 78 extend.

Also attached to the main body 90 of the flex circuit 76 are two additional devices which are specific to the handpiece in which the flex circuit is fitted. In handpiece 32, a first one of the devices is a Hall effect sensor 94. The Hall effect sensor 94 monitors the position of a magnet internal to the hand switch 39 when the hand switch used to control the on/off state and speed of the motor 50. The second device is a temperature sensor 96 that monitors the internal temperature of the handpiece 32. In the illustrated version of the invention, Hall effect sensor 94 is mounted in a cutout space 98 formed along the perimeter of the flex circuit main body 90 that is distal from the head section 84 of the flex circuit 76. Temperature sensor 96 is secured to the surface of the flex circuit 76 that is directed inwardly towards the field coil assembly 58. Temperature sensor 96 is further attached to the flex circuit so as to be located immediately inside the edge of the main body 90 that is furthest from the head section 84. Consequently, when the flex circuit is fitted in handpiece 32, temperature sensor 96 is located adjacent the forward end of the field coil assembly 58 so as to also be in relatively close proximity with the neck 56 of the motor housing 50 and the bearing assembly 64 fitted therein.

In some versions of the invention, a single conductive trace 78 serves as the address/data bus for both NOVRAM 72 and EEPROM 74. In these versions of the invention a resistor 102 may be series connected into the branch of the trace that extends to one of the memories. Also, it is typically necessary to provide a reference voltage to the sensors 94 and 96 secured to the flex circuit 76. As will be described hereinafter, this reference signal is supplied by the control console 36. Typically, in order to minimize spiking of the reference voltage, a capacitor 104 is connected across the conductive trace 78 over which the reference voltage is carried on the flex circuit and a complementary trace 78 that serves as en analog signal ground.

In order to ensure that the data within memories 72 and 74 is accurately read by control console 36, flex circuit 76 is provided with an additional conductive trace 78 that functions as a dedicated digital ground conductor. This digital ground conductor is only connected to the ground pins of memories 72 and 74. This conductor is separate from the analog ground conductor to sensors 94 and 96. It is also necessary that the digital ground conductor and the associated signal conductor that is connected to memories 72 and 74 be configured as a twisted pair of wires to the maximum extent possible, both on the flex circuit 76 and in the cable 43 connected to the control console 36.

The back shell 82, now described with reference to FIGS. 3 and 4, has a main body 106 with an open front end 108 to facilitate the fitting of the motor 52 and assembled flex circuit 76 in the shell. The main body 106 of the back shell is further formed to have outwardly projecting, longitudinally extending ribs 110. The ribs 110 provide a compression fit between the back shell 82 and the adjacent inside wall of the motor housing 50. In some versions of the invention ribs 110 are at least partially sheared off when the back shell 82 is fitted in the motor housing 50. Integral with the main body 106 of the back shell 82 is an end cap 112. End cap 112 is formed with a bore 113 coaxially aligned with the main body 106 through which the rear portion of the rotor 60 of the motor 50 extends.

Back shell 82 is further formed with an elongated, slot-like opening 114 that extends the length of the shell through both the main body 106 and end cap 112. opening 114 is dimensioned to allow the flex circuit 76 to be positioned so that the head section 84 can be spaced away from the end of the end cap 112, the spine 86 is seated in the opening 114 and the main body 90 disposed against the inside surface of the main body 106 back shell. When the flex circuit 76 is so fitted in the back shell 82, the arms 88 of the flex circuit are located around the outside of the end cap 112. The ends of the arms 88 are then seated in slots 116 formed in the end cap 112, best seen by reference to FIG. 4. In the depicted version of the invention, end cap 112 is further formed with flat surfaces 118 that extend from opening 114 to the slots 116. Flat surfaces 118 are recessed relative to the outsider diameter of the rest of the end cap 112. Memories 72 and 74, resistor 102 and capacitor 104 are attached to flex circuit 76 so as to be directed towards flat surfaces 118 of the back shell 82. Thus, owing to the positioning of the memories 72 and 74, resistor 102 and capacitor 104 in the relatively open spaces defined by surfaces 118, once the handpiece 32 is subjected to the sterilization process, the vapor introduced around these components is able to be drawn away therefrom relatively quickly.

Returning to FIGS. 2 and 3, it can be seen that a front shell 122 covers the outer surface of the flex circuit 76 that projects forward of the back shell 82 and is seated in opening 114 formed in the back shell. Front shell 122 has a ring shaped head section 126 that is seated around the exposed portion of the main body 90 of the flex circuit 76. A stem 127 formed integrally with the head section 126 extends rearwardly therefrom. The front shell 122 is positioned relative to the head section so that the front shell stem 127 is seated in the opening 114 in the back shell so as to cover the portion of the flex circuit seated in the opening.

A rear bearing housing 128 is fitted over the end of the end cap 112 of the back shell 82. Rear bearing housing 128 has a relatively large diameter base 130 with an outer diameter that allows it to be fitted in relatively close proximity against the inside wall of the motor housing 50. The base 130 of rear bearing housing 128 is formed to define an elongated slot 131 in which the spine 86 of the flex circuit 76 is seated. The inside of the base 130 defines a void space 134 in which the head section 84 of the flex circuit 76 is seated. A reduced diameter, bearing sleeve 135 extends forward from the base 130 into the bore 113 defined in the back shell end cap 112. A rear bearing assembly 132 is located in bearing sleeve 135. Rear bearing assembly 132 extends between the bearing sleeve 135 and the end of the motor rotor 60 for holding the rotor for stable rotation.

A one-piece, cylindrical socket holder 137 is fitted in the end of the motor housing 50 so as to cover the rear bearing housing 128 and the exposed head section 84 of the flex circuit 76. Socket holder 137 has a tube-shaped outer body 138 that is dimensioned to be compression fitted against the inside wall of the motor housing 50. The outer body 138 is formed with an outwardly projecting, circumferential flange 140 located at the rear end thereof that limits forward movement of the socket holder 137. Outer body 138 is further formed to define an elongated slot 141 that extends along the inside wall of the outer body to facilitate the proper coupling of the cable 43 to the socket holder 137.

A head ring 142 extends forward from the outer body 138 of the socket holder 137. Head ring 142 has a diameter less than the diameter of the outer body 138. More particularly, the head ring 142 of the socket holder 137 has an outer diameter that allows the head ring to be fitted against the inside circumferential wall of the base 130 of the rear bearing housing 128 that defines space 134. An O-ring 144 located around the outer body 136 of the socket holder 137 seals the inside of the motor housing 50. In the illustrated version of the invention, O-ring 144 is seated in an annular slot 146 defined along the forward outer edge of the outer body 136.

Socket holder 137 further includes a solid, cylindrical socket boss 148. Socket boss 148 extends rearward from the head ring 142 of the socket holder 137 and is inwardly spaced from the outer body 138. Socket boss 148 is formed with a center bore 150 in which a head cap screw 152 is seated. The tip end of the head cap screw 152 is seated in a complementary bore, in the center of the rear bearing housing 128. A set of conductive sockets 154 are seated in a ring of counter-tapered bores 148 formed in a circular ring around the center bore 150. The sockets provide the conducive paths from the cable 43 to the flex circuit 76. The tip ends of the sockets 154 are seated in holes 156 formed in the head section 84 of the flex circuit 76.

FIG. 5A is a cross sectional view of the cable 43 that contains the conductors over which signals are exchanged with a handpiece such as handpiece 32. Cable 43 has an outer jacket 160 formed of insulating material such as silicone rubber. Immediately inside jacket 160 is a braided shield 162 formed of tinned copper. Within shield 162 are the conductors over which energization signals are applied to the handpiece motor 50, the memories 72 and 74 are accessed and the sensors 94 and 96 are monitored. In the illustrated version of the invention, wherein the handpiece motor 50 is a three-winding, brush less, Hapless (sensor less) motor, cable 43 is provided with three motor conductors 164 each of which is tied through flex circuit 76 to a separate one of the windings forming the field coil assembly 58. Six individually insulated signal conductors 166 are provided for serving as the signal path between the control console 36 and the memories 72 and 74 and the sensors 94 and 96.

As seen by reference to FIG. 5B, each motor conductor 164 includes a conductive core 168 formed of copper. An insulator 170 is located immediately around the core 168. A spiral shield 172 is located around the insulator 170. An insulating jacket 174 that extends around shield 172 serves as the outer cover for each conductor 164. Returning to FIG. 5A it can be seen that strands of polyester filler 176 provide cushioning around conductors 164 and 166. The conductors 164 and 166 as well as the strands of filler 176 are wrapped in PTFE tape 178. Jacket 160 and shield 162 are fitted around the wrapped sub-assembly.

Figure 11:
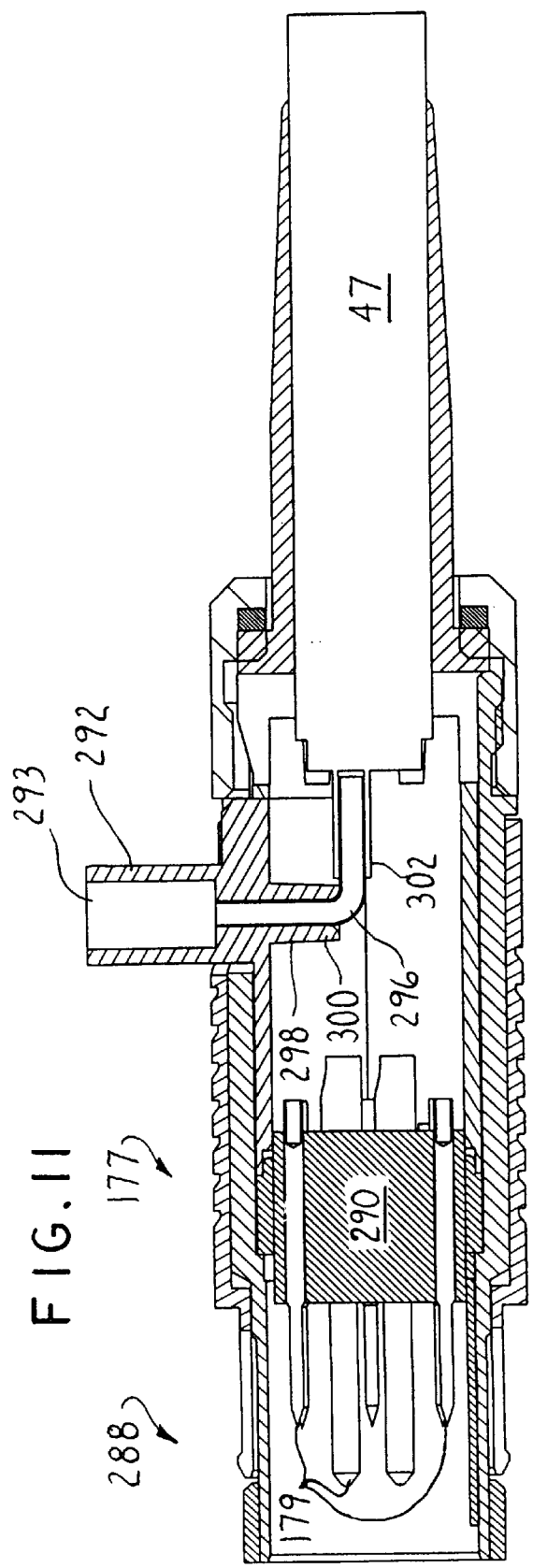
FIG. 11 is a cross sectional view of the console-end plug of the control cable used of FIG. 10.

FIG. 11 depicts the male plug 177 used to connect cable 47 to control console 36. Plug 177 has the same basic components as found in the male plug used to attach cable 43 to the control console 36. Terminal pins 179 are connected to conductors 164 and 166 within the cable provide the electrical connections to complementary socket openings, (not illustrated), on the face of the control console 36. Two of the terminal pins 179 that extend into complementary socket openings in the control console are shorted together. As will be discussed hereinafter, the signal that the control console 36 asserts through the shorted pins 179 is used by the control 36 console to determine whether or not a cable 43 or 47 is attached to a control console socket.

Figure 12:
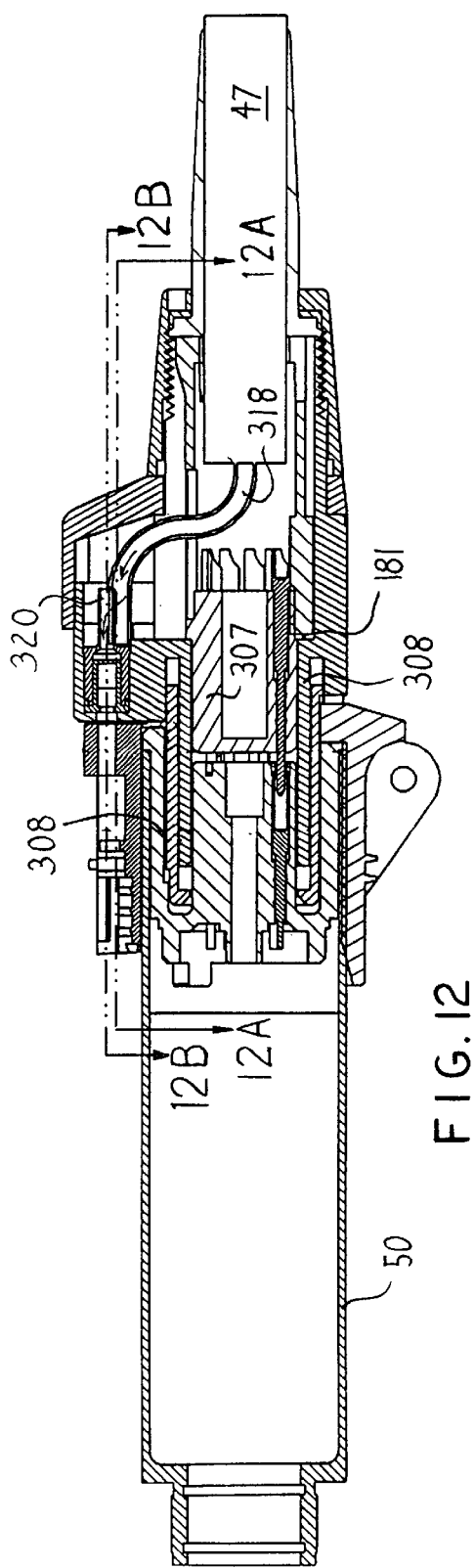
FIG. 12 is a cross sectional view illustrating how the cable of FIG. 10 is coupled to both a handpiece and a light-and-water clip.
Figure 12B:
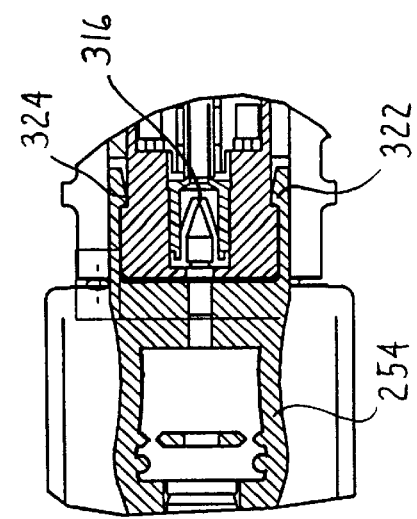
FIG. 12B is a cross sectional view illustrating the water coupling between the cable and light-and-water clip.
Figure 12A:
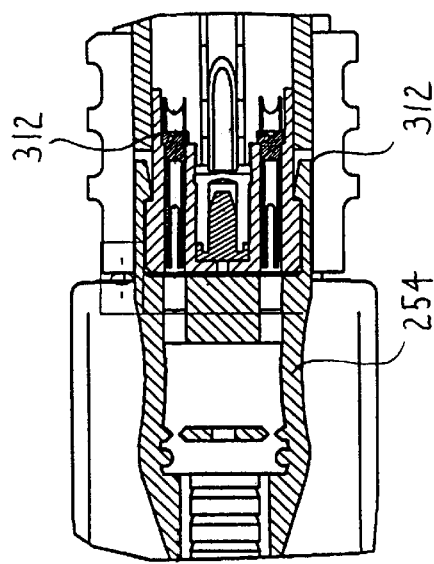
FIG. 12A is a cross sectional view illustrating the electrical coupling between the cable and the light-and-water clip.

An insulated handpiece plug 180 (FIG. 6) provides the connections at the opposite end of the cable 43 between the cable and the handpiece 32. Handpiece plug 180 is provided with a number of pins 181 (FIG. 12) that provide the conductive connections between the conductors 164 and 166 in the cable 43 and the sockets 154 in the handpiece 32. Handpiece plug 180 is provided with a single spline 308 (seen in FIG. 9 with respect to plug 242 of cable 47). The spline has a generally rectangularly shaped profile that extends the length of forward portion of the head that is fitted. into socket holder 137. The spline is designed to be fitted into the complementary slot 141 formed in the socket holder 137 to ensure proper alignment of the pins of the cable 43 with the sockets 154 in the handpiece 32.

Figure 6:
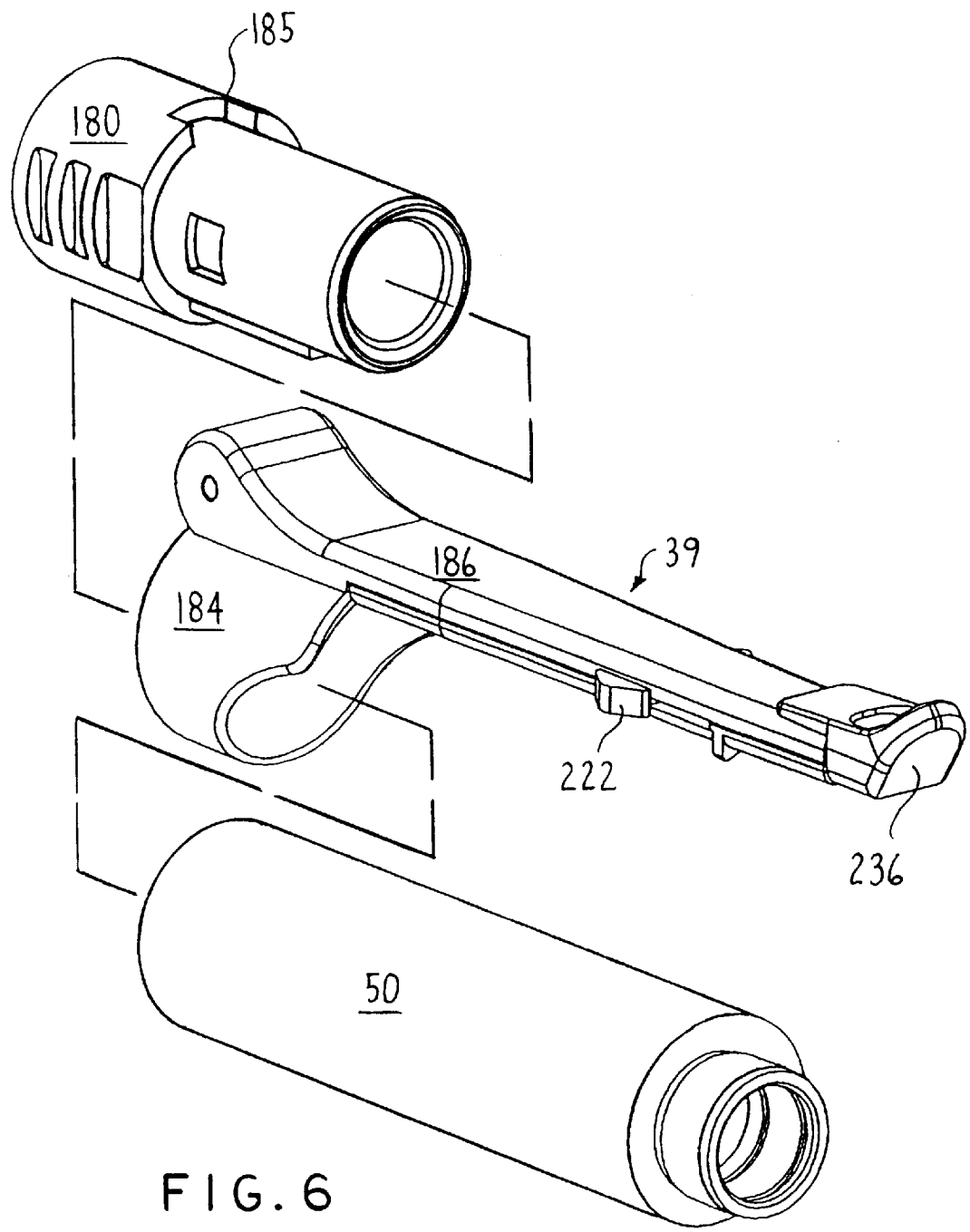
FIG. 6 is an exploded view illustrating how a removable hand switch is attached to a handpiece.
Figure 7:
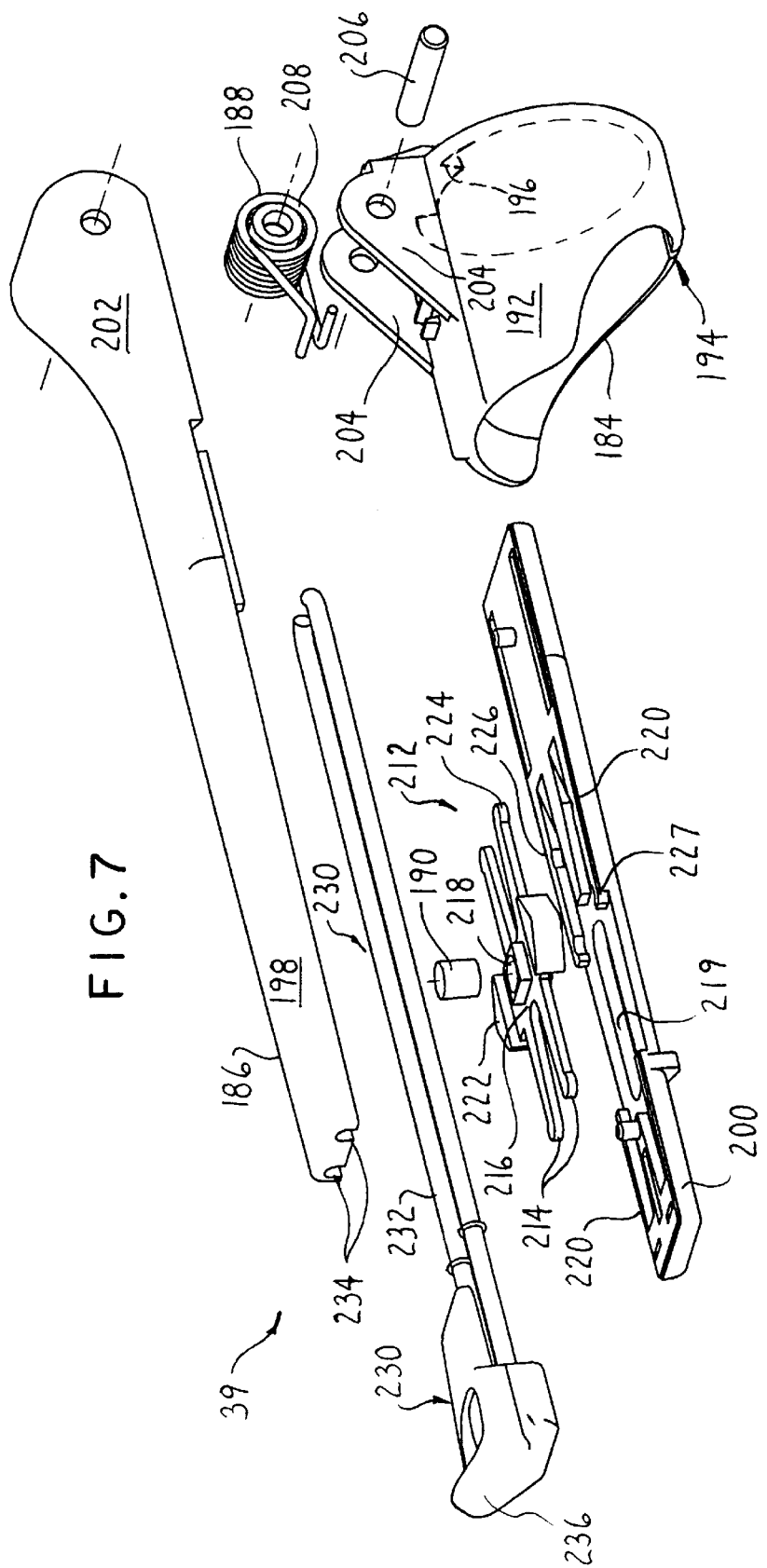
FIG. 7 is an exploded view of the components forming the removable hand switch.

The removable hand switch 39 attached to handpiece 32 is now described by reference to FIGS. 6 and 7. Hand switch 39 includes a slip ring 184 that is removably fitted over the motor housing 50 of handpiece 32. A lever arm 186 is pivotally secured to slip ring 184 so as to extend forward along the length of the handpiece 32. A torsion spring 188 located between slip ring 184 and lever arm 186 biases the lever arm so that it is normally pivoted away from the handpiece. A magnet 190 is fitted in lever arm 186. The position of the magnet 190 is monitored by Hall effect sensor 94 so as to as an indication of the desired operating speed of the motor 50 internal to the handpiece 32.

The slip ring 184 has a plastic, sleeve like main body 192 that is designed to be releasable compression secured over the motor housing 50. In order to ensure a proper fit of the hand switch, the main body 192 of the slip ring 184 is shaped to have an inside diameter that is slightly less than the outside diameter of the motor housing 50. The main body 192 of the slip ring 184 further has an elongated slot 194 that extends the length of the body in order to facilitate the removable clamping action of the slip ring 184 to the handpiece.

Main body 192 of slip ring 184 is also formed with a solid tab 196, (shown in phantom,) that extends inward from the rear end of the main body 192 towards the center axis of the main body. Tab 196 is dimensioned to prevent the slip ring from being fitted over the front end of a handpiece 32 or 31. When cable 43 is coupled to handpiece 32, of the slip ring 184 and radially inward relative to the main body. The inward-directed end of tab 196 is configured to be seated in a complementary cut-out 185 formed in the handpiece plug 180 of the cable 43. The seating of the slip ring tab 196 in cut-out 185 formed in the handpiece plug 180 ensures that the hand switch magnet 190 is aligned with the radial line relative to the center axis of the handpiece along which the complementary Hall effect sensor 94 is located.

Lever arm 186 is formed out of complementary upper and lower shells 198 and 200, respectively, that are ultrasonically welded together. Upper shell 198 has a tail end 202 that is located between two parallel, spaced apart mounting tabs 204 that extend outwardly from the main body 192 of the slip ring. 184. A pin 206 that extends through aligned openings in the tabs 204 and in the tail end 202 of the lever arm upper shell 198 secures the lever arm 186 to the slip ring 184. Torsion spring 188 is fitted around pin 206. In order to prevent spring 188 from compressing against pin 206, a sleeve-like mandrel 208 is fitted in the spring and the pin is rotatably fitted in the mandrel.

Magnet 190 is housed in a movable holder 212 mounted in the lever arm 186. Holder 212 has two spaced apart, longitudinally extending parallel legs 214. A cross web 216 extends between the legs 214. The magnet 190 is mounted in a support collar 218 that is mounted to the cross web 216. In the illustrated version of the invention, magnet 190 is positioned to extend through an elongated slot 219 formed in the lower shell 200. The legs 214 of the holder 212 are mounted in grooves 220 formed in the lower shell 200 of the lever arm 186. Grooves 220 have a greater length than the complementary legs 214 so as to allow the longitudinal movement of holder 212.

The position of holder 212 is set by the manual displacement of opposed tabs 222 that are attached to cross web 216 and that project outwardly from lever arm 186. Holder 212 thus allows the magnet 190 to be positioned in a first position relative to the longitudinal axis of the handpiece 32 wherein the magnet is spaced from the complementary Hall effect sensor 94 and a second position wherein it is longitudinally closed to the sensor. Thus, the magnet is placed in the first position, a safety position, so as to prevent unintended actuation of the motor 52 in the event the lever arm 186 is inadvertently depressed. only when magnet 190 is in the second position, a run position, will the depression of the lever arm 186 bring the magnet close enough to Hall effect sensor 94 so that the sensor will detect the proximity of the magnet. In the described version of system 30, the holder magnet 190 is in the safety position when it is positioned toward the rear end of the handpiece 32.

In the illustrated version of the invention, the far ends of the legs 214 of holder 212 are provided with outwardly curved feet 224. The lower shell 200 is formed with notches 226 at the ends of the grooves 220 in which the feet seat when the holder is placed in the safety position. A second pair of opposed notches 227 are formed integrally with the grooves forward of the first pair of notches. This seating of the feet 224 in the notches 226 or 227 places a resistance on the movement of the holder 212 from, respectively, the safety position or the run position. The imposition of this resistance prevents the unintended movement of the magnet 190 from the position in which it is placed.

An extender unit 230 is retractably seated in lever arm 186. The extender unit 230 is provided to facilitate the use of the hand switch 39 by physicians with different hand sizes and/or different techniques for holding the handpiece 32. Extender unit 230 includes a U-shaped guide rod 232. The opposed legs of guide rod 232 are slidably fitted in complementary openings 234 formed in the front of the upper shell 198 of the lever arm 186. A head piece 236 is attached to the exposed head of guide rod 232 so as to define a finger rest: surface for the surgeon to place his/her finger. The opposed ends of the legs of the guide rod 232 are bent inwardly to prevent the extender unit 230 from being totally withdrawn from the lever arm 186.

The light-and-water clip 45 that is secured to handpiece 33 is now initially described by reference to FIGS. 8 and 9. Light-and-water clip 45 includes a rear shell 240 that is secured to a complementary handpiece plug 242 attached to one end of cable 47. A flexible silicon carrier tube 244 extends forward from the rear shell 240. Carrier tube 244 defines the conduits through which the irrigating water flows and in which the conductors that carry the illuminating voltage for the light bulb are seated. The head end of the carrier tube 244 is attached to a front shell 246 that is snap-fitted to the forward end of the handpiece 33. A bulb 248 is seated in the front shell 246 for illuminating the surgical site. A rigid outlet tube 250 is attached to the front shell 246 for providing a fluid conduit through which the irrigating water is discharged onto the surgical site.

Rear shell 240 of light-and-water clip 45 includes upper and lower halves 252 and 254, respectively, that are secured together. Seated inside a cross web 256 formed in the lower half 254 of shell 240 are two outwardly directed conductive pins 258. Pins 258 provide the electrical connection to the handpiece plug 242. A rigid water inlet tube 260 extends outwardly from cross web 256 to provide a conduit for the irrigating water. As can be seen by reference to FIG. 9), the lower half 254 of rear shell 240 is provided with legs 262 that extend rearward of cross web 256. Legs 262, in addition to facilitating the coupling of clip 45 to handpiece plug 242, protect pins 258 and tube 260 so as to prevent the exposed ends thereof from being inadvertently bent.

Carrier tube 244 is clamped at one end between the upper and lower halves of rear shell 240. The carrier tube 244 is formed with a first conduit 264 in which the water inlet tube 260 is fitted. carrier tube 244 has a second conduit 266 extending the length thereof that has a dumbbell-shaped profile. Insulated conductors 268, shown in phantom, are fitted in the opposed ends of conduit 266. Conductors 268 are connected to pins 258 and serve as the conductive paths over which the energization signals are applied to the bulb 248.

It is anticipated that carrier tube 244 will have a length that will allow the associated front shell 246 of light-and-water clip 45 to be attached to handpiece 33 forward of the motor housing. Moreover, the flexible nature of carrier tube 244 allows the front shell 246 to be rotated relative to the fixed position of the rear shell 242. This allows the bulb 248 and water outlet tube 250 to be selectively positioned by the surgeon around the circumference of the handpiece 33.

Front shell 2445 of light-and-water clip 45 has a main frame 270 and a complementary cover 272 that is snap-fitted over the main frame. Main frame 270 is shaped to have an approximately C-shaped clamping member 274 that is dimensioned to be snap fitted over the handpiece 33. A head piece 276 is attached to the clamping member 274. The shell cover is snap fitted over head piece 276 so as to facilitate the securing of the forward end of carrier tube 244 therebetween. Head piece 276 is formed with a first bore 278 in which bulb 248 is seated. (Not shown are the connections between bulb 248 and the conductors 268 in the carrier tube.) A heat shield 280 is fitted around bulb 248 to prevent the heat generated by the bulb from radiating.

Outlet tube 250) is seated in a second bore 282 formed in head piece 276. In the depicted version of the invention, outlet tube 250 has two opposed sections that are parallel and axially offset from each other and an intermediate section that connects the opposed sections. The portion of tube 250 that extends rearward from head piece 276 is fitted into the conduit 264 in carrier tube 244 for receiving the irrigating water. The opposed end of outlet tube 250 projects forward from front shell 246 for delivering the water to the surgical site.

In preferred versions of the invention both the rear shell 240 and front shell 246 of light-and-water clip 45 are shaped so that the thickest sections thereof extend out no further than 0.5 inches from the adjacent outside surface of the handpiece to which they are attached. In still more preferred versions of the invention, these shells extend out no more than 0.3 inches. The front shell clamping member 274 has a length no greater than 0.6 inches. The carrier tube 244 that serves as the conduit for the water and conductors has, in many versions of the invention a maximum width of 0.4 inches and a top height of 0.25 inches. In more preferred versions of the invention the maximum limits of these dimensions are 0.25 and 0.2 inches respectively. Collectively, these features ensure that the coupling of light-and-water clip 45 to a handpiece does not significantly interfere with handling of the handpiece.

Figure 10:
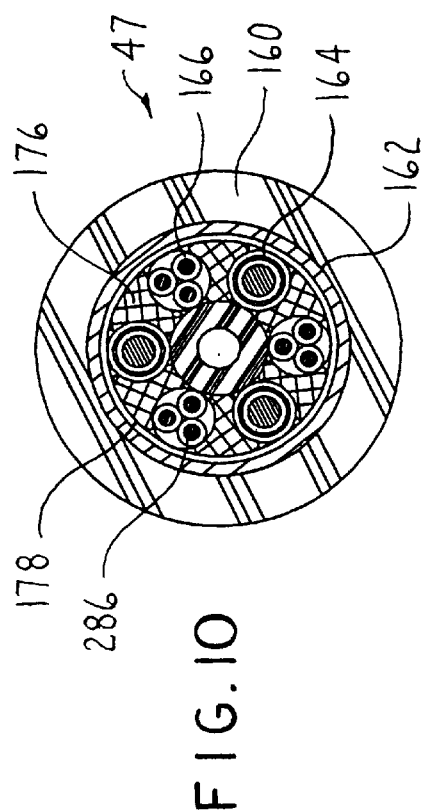
FIG. 10 is a cross sectional view of the control cable used with the light-and-water clip of FIG. 9.

Cable 47, through which signals are exchanged with handpiece 33 and water delivered to light-and-water clip 45, is now described by reference to FIG. 10. Cable 47 has the same basic outer jacket 160, braided shield 162 and motor conductors 164 described with respect to cable 43. An irrigation tube, 286 extends longitudinally down the center of cable 47. Cable 47 is also provided with nine signal conductors 166 arranged in groups of bundles of three. The cable 47 is constructed so that the motor conductors 164 and bundles of signal conductors 166 are located are alternatingly and circumferentially arranged around the irrigation tube 286. Strands of polyester filler 176 are located adjacent irrigation tube 286 to separate the motor conductors 164 and bundles of signal conductors 166 from each other. Conductors 164, 166, filler strands 176 and irrigation tube 286 are wrapped in PTFE tape 178.

FIG. 11 illustrates a console plug 288 attached to one end of cable 47 for connecting the cable to control console 36 and pump 40. The plug 288 has generally a metal or plastic body designed to be fitted into a complementary socket, (not illustrated,) mounted in the face of the control console 36. One end of cable 47 is fitted in the opposed end of the plug 288. A solid pin holder 290 is mounted inside plug 288. The conductive pins 179 that provide the electrical connection between the control console 36 and the conductors 164 and 166 are mounted to pin holder 290 so as to extend outwardly therefrom. It should be recognized that plug 288, in addition to having sufficient conductive pins 179 to facilitate required connections to the motor and devices internal to the handpiece 33, also has additional pins to provide an energization voltage to the bulb 248 mounted in clip 45.

Console plug 288 is further formed with an inlet stud 292 through which irrigating water from pump 40 is introduced into cable 47. Inlet stud 292 extends perpendicularly away from the main axis of the plug, the axis along which pins 179 are oriented. Inlet stud 292 is formed with a bore 293 designed to receive a complementary outlet tube 294 (FIG. 1) from the pump 40. An L-shaped connector tube 296 provides the fluid communication path from inlet stud 292 to tube 286 within cable 47. One end of connector tube 96 is fitted in an inwardly directed mounting stud 298 that is axially aligned with inlet stud 292. More specifically connector tube 296 is fitted in a bore 300 formed in stud 298 so that the tube is open to the bore 293 in the inlet stud 292. The opposed end of connector tube 296 is fitted into an extension 302 of irrigation tube 286 that extends rearward of the end of cable 47.

FIGS. 9, 12, 12A and 12B depict the structure of handpiece plug 242 of cable 47 and how the plug is connected to handpiece 33 and light-and-water clip 45. Plug 242 includes a main body 306 formed of plastic to which the end of cable 47 is attached. Main body 306 is formed with a solid pin holder 307 that is dimensioned to received within the outer body 138 of the socket holder (FIG. 2) attached to the end of the handpiece. The pins 181 that provide the electrical connections to the handpiece are mounted in pin holder 307 and extend forwardly therefrom. As seen best in FIG. 12, the main body 306 of the plug 242 is further shaped to have an outwardly directed spline 308. Spline 308 seats in complementary slot 141 to facilitate proper alignment of pins 181.

Handpiece plug 242 further includes a head 310 that is attached to the outside of the main body 306 so as to be located diametrically opposite the spline 308. Head 310 is provided with two conductive sockets 312. Sockets 312 are positioned to receive the complementary conductive pins 258 that extend rearwardly from the rear shell 240 of clip 45. The signal conductors 166 in cable 47 that supply the energization current to the bulb 248 are attached to the sockets 312, (connections not shown).

The head 310 of handpiece plug 242 is further formed with a forward directed outlet bore 314 that is located between and slightly above sockets 312. Outlet bore 314 is dimensioned to receive the water inlet line 260 that extends from the light-and-water clip 45. A duck-billed seal 316 is seated in bore 314 and positioned to be opened by inlet line 260. Seal 316 thus prevents water from being discharged from cable 47 when there is no light-and-water clip 45 attached and opens to allow liquid flow when the clip is in place. Water from cable 47 is directed into bore 314 through an extension line 318 integral with irrigation tube 286 that extends from the end of cable 47. The extension line 318 is coupled into a sealed chamber 320 formed in the head 310 of the handpiece plug 242 from which bore 314 extends. In the depicted version of the invention, chamber 320 is dimensioned so that extension line 318 is coupled into the chamber at a position that is closer to the longitudinal axis of the associated handpiece than the position from which bore 314 extends from the chamber.

Legs 262 that extend rearward from the light-and-water clip 45 secure the clip to the head 310 of the handpiece plug 242. Each leg 262 is formed with an inwardly directed foot 322. The feet 322 seat against opposed inwardly directed steps 324 formed in the handpiece plug head 310 forward of the forward face of the head. Feet 322 are pivoted away from the handpiece head 310 by the manual inward compression of the sides of the lower half 254 of the rear shell of light-and-water clip 45.

Returning to FIG. 1, the structure of the foot switch assembly 46 is now discussed. In the depicted version of the invention, foot switch assembly 46 has five pedals 44a, 44b, 44c, 44d and 44e. Pedals 44a and 44b which are opposed right and left main pedals are relatively large in size are spring biased so as to assume a normally fully extended position. Pedals 44a and 44b carry magnets, (not illustrated) the positions of which are monitored by complementary Hall effect sensors 327 (one shown in phantom). The selective depression of pedals 44a and 44b actuates the associated handpiece 32 or 33. More particularly, in one configuration of the system, the depression of pedal 44a is used to cause the associated handpiece motor to rotate in a first direction while the depression of pedal 44b is used to cause the handpiece motor to rotate in the opposite direction. Alternatively, the system 30 can be configured so that depression of one pedal 44a or 44b causes the associated handpiece motor to rotate in a single direction and the depression of the other pedal is used to cause the motor to engage in oscillatory rotation. A NOVRAM 329 (shown in phantom) internal to the foot switch assembly stores data about the characteristics of the output signals of the particular sensors 327 mounted in the assembly.

Pedals 44c, 44d, 44e are located above pedals 44a and 44b. Pedals 44c, 44d and 44e control the state of three bistate switches, respectively, foot switch assembly left, center and right switches. In one configuration of the invention the surgeon can depress pedal 44c if irrigation, the actuation of pump 40, is desired. Pedal 44d is depressed in order to indicate which handpiece 32 or 33 the surgeon wants as the active handpiece. Pedal 44e is actuated by the surgeon to indicate if he/she wants the bulb 248 associated with the active handpiece 32 or 33 to be actuated. Foot switch assembly 46 is connected to control console 36 by a cable 328. Cable 328 carriers conductors over which signals generated by the Hall effect sensors associated with pedals 44a and 44b and the signals selectively transmitted through the switches associated with pedals 44c, 44d and 44e are supplied to the control console 36. Cable 328 also carriers conductors connected to the NOVRAM 329 so as to enable the control console to retrieve the data stored therein.

FIG. 13 is a block diagram of the data fields contained within the NOVRAM 72 within a handpiece such as handpiece 32. NOVRAM 72 contains three basic types of data: header data which provides basic identification about the handpiece in which it is installed; encyclopedia data which describes the operating characteristics of the handpiece; and custom screen data that contains instructions about any custom images that the handpiece requires presented on display 37.

The first data presented is the header data and the first field is a header length field 342 which provides an indicate of the portion of the memory occupied by the header data. A set of handpiece identification fields 343, 345, and 345 follow header length field 342. Handpiece identification fields 343–345 contain such information as the name of the handpiece, for example, sagittal saw, the part number for the handpiece, the handpiece serial number, and a code identifying the manufacturer of the handpiece. A code revision field 346 contains an indication of the version of the data in the NOVRAM 72 that is being read. A check sum field 347 contains data useful for error detection/error correction of the data read from the handpiece. The data contained in fields 342–347 are the header data.

The encyclopedia data follows the header data. the first field of encyclopedia data is a table length field 348. Table length field 348 contains an indication of the size of the NOVRAM 72 in which the encyclopedia is contained. Following table length field 348 is a handpiece definition field 350). Handpiece definition field 350 contains information that Describes the characteristics of the handpiece. This information can include a description of: whether the handpiece is a micro duty or heavy duty handpiece; if the forward/reverse direction controls are convention or in reverse orientation, whether the motor is run with or without feedback; whether the light and water accessories can be used with the handpiece; and the number of significant digits that should be presented on the image formed on display screen 37.

The next two data fields, fields 352 and 354, are device type fields that identify the characteristics of devices that are installed into the handpiece. In one version of the invention, each field 352 and 354 is a four bit field. Each one of the 16 bit combinations serves to identify whether or not a device is present and the features of the device. For example, in one code scheme bit combination 00000 is used to indicate no device is present and combination 0001 is used to indicate the signal generated by the device is a main trigger (combination forward and reverse trigger). This code may be contained within NOVRAM 72 if the device is the described Hall effect sensor 94 (FIG. 3). In this code scheme, combination 0100 is used to indicate that the device is an internal handpiece temperature sensor 96 (FIG. 3) and that the signal generated device is representative of the temperature of the handpiece.

The next 8 fields, fields 356–370, are voltage level fields that contain information about range of signals that the devices internal to the handpiece generate and how they control the actuation of the handpiece 32. Four of the fields, fields 356–362, contain information about the signal produced by first device, hereinafter generically referred to as device A. Fields 356–370 contain information about the signal produced by the second device, hereinafter referred to as device B.

The information contained in fields 356–370 are a function of the nature of the associated devices. For example if the devices are sensors that generate signals represented of the user-selected operating speed of the motor and the temperature of the device, fields 356–362 and 366–370 would, respectively, contain data about the motor speed signal and the thermal state of the handpiece. Table 1 below identifies the type of the data that is potentially present in these fields.

TABLE 1

Data type based on device type.

| Data Field | Device Is Speed Sensor | Device Is Temp. Sensor |
| --- | --- | --- |
| 356, 364 | Maximum Voltage From Sensor (Voltage Representative of Maximum Speed) | Voltage Representative Of Device Shut-Down Temperature |
| 358, 366 | Minimum Voltage From Sensor (Voltage Representative of Minimum Speed) | Voltage Representative of Device Warning Temperature |
| 360, 368 | Hysterises Voltage (Voltage Above Minimum Voltage At Which Motor Is Initially Actuated) | Undefined |

Fields 362 and 370 contain filter value data in the event there is a need to digital filter the signals generated by devices A and B, respectively.

It should be recognized that the foregoing description merely described the data contained in fields 356–370 for just two types of devices. The data contained in these fields may be significantly different for other types of devices. For example, one potential device integral with a handpiece may by a set of buttons that represent a plurality of switches the physician can selectively depress. With this type of device, the depression of a specific set of buttons would cause a unique signal to be generated by the handpiece 32 that the control console 36 would, in turn, recognize as a specific command If these buttons form an installed device, the associated fields 356–362 or 364–370 could contain data indicating the type of command a particular signal produced by the device represents. Two such commands for example could be commands to raise and lower the maximum speed at which the motor internal to the handpiece can operate.

Fields 372–382 contain data regarding the coefficients used to process the signals produced by devices in the handpiece. Fields 372–376 contain data for three coefficients used to process the signal generated by device A. Fields 376–382 contain data for three coefficients used to process the data used to process the signal generated by device B.

In general it is contemplated that the data produced by devices A or B be processed using the following polynomial function:

$$y = ax^2 + bx + c$$

Where:

x is the digitized version of the signal produced by device A or B y is the result used by the downline processing modules internal to the control console. It is contemplated that fields 372 and 378 contain the data representative of coefficient "a"; fields 374 and 380 contain the data representative of coefficient "b"; and fields 380 and 382 contain the data representative of coefficient "c". Thus, the data in fields 372–382 provides coefficients for greater than first order correction of variations from the normal of the signals produced by the handpiece devices that occur due to differences in the output characteristics of the individual devices.

Fields 384–392 contain data used to establish the operating speeds of the motor 52 (FIG. 2) internal to the handpiece. Field 384 contains data representative of motor stall speed, the minimum speed (revolutions per second) at which the motor 52 should operate when the signal from the associated handpiece device A or B is at the minimum voltage level. Field 386 contains an indication of the lowest maximum speed which the user can establish for the motor 50. This data makes it possible for the medical personnel to establish their own set point for the highest maximum speed at which they want the motor to function, if they wish that speed to be below the established maximum speed. Field 388 contains data representative of the highest speed at which the motor can operate. Inferentially, the data stored in field 388 is also representative of the highest maximum speed set point at which the user can program the handpiece. Field 390 contains data indicating the incremental difference in speed that the maximum speed set point of the motor can be adjusted. For example, field 390 contains data indicating whether the maximum speed set point can be adjusted in increments of 100 RPM, 500 RPM or 1000 RPM.

Fields 391 and 392 contain data that is used if the motor can be operated in a forward-reverse oscillatory mode. Field 391 contains an indication of the lowest speed at which the motor can be operated in the oscillatory mode. Field 392 contains data representative of the maximum speed at which the motor can be operated at when in the oscillatory mode.

Field 394 contains data about the gear ratio of the handpiece 32. This data is used to calculate the true speed of the cutting attachment coupled to the handpiece. In the handpiece, handpiece 32, a cutting attachment is directly coupled to the motor rotor 60. Therefore for this particular handpiece 32, field 398 would contain data indicating a 1:1 ratio between the rotation of the motor and the rotation of the cutting attachment. Field 396 contains data about the number of poles internal to the motor. Control console 36 uses this data to regulate the application of energization current to the individual poles.

Fields 398 and 400 contain data about the bias current that is applied to the handpiece in order to energize the devices A and B internal to the handpiece 32 or 33. Fields 398 and 400, respectively, contain data about the minimum and maximum bias current that is applied to the handpiece 32 or 33, Fields 402–404 contain data regarding the maximum current the motor should draw when in different phases of its cycle of operation. Fields 402 and 403 contain indication of the maximum current the motor should draw during its initial start up cycle. More specifically, field 402 contains data indicating the maximum current that should be drawn when the motor is in the reset phase of the start up cycle. Field 403 contains an indication of the maximum current the motor should draw during the enable phase of the start up cycle. Field 404 contains an indication of the maximum current at which the motor should perform an adjustment of the coefficient of a transfer function used to the motor should draw during its run time.

Fields 406, 408 and 410 contain the coefficients used in an equation to calculate the current set point based on defined torque set point. These coefficients are needed, because, as explained hereinafter, the memory also includes an indication of the maximum torque the motor should deliver for given motor speeds. While ideally the current drawn-to-torque generated ratio should be linear, there may be some variation. Consequently, coefficients that used in a greater-than-first order equation are stored within the memory so that the control console can perform a relatively accurate torque-to-current conversion. In the described version of the invention, three coefficients, enough for providing the constants for a quadratic equation, are supplied.

Fields 412, 414 and 416 contain the coefficients employed during motor control when the control console is engaged in current control mode of the motor. Fields 418, 420 and 422 contain the coefficients employed when the control console is engaged in the speed control mode of the motor. In both modes, the control console is engaged in proportional integral differential control of the motor. That is the control console modifies the feedback signals received by the motor in order to ensure its precise operation.

Fields 428–434 contain data representative of the torque/speed set points that define the safe operating range of the motor. As seen by line 436 of FIG. 14, a motor has a linear speed-to-torque ratio wherein there is an inverted linear relationship between the maximum speed at which a motor can be driven and the torque the motor should be allowed to develop at that speed in an open loop drive mode. If, for a given speed the motor develops excess torque, the energization current applied to the motor may cause undesirable results to occur such as ranging from the excessive heating of the motor to the wearing out of the components forming the motor.

In the integrated tool system 30 of this invention, fields 428–434 contain set point data that allow the control console to internally map a custom speed/torque plot 438 for the motor internal to the handpiece 32. Fields 428, 430 and 432 each contain data indicating for a given percent of the maximum speed of the motor an indication of the percent of the maximum torque the motor should be allowed to develop. For example, field 432 may contain an indication that when the motor is operating at 20% of its maximum speed it should develop more than 65% of the maximum permissible torque. The maximum speed upon which these values are based is the maximum speed specified in motor maximum speed field 388. The fourth speed/torque field, field 434, contains an indication of the maximum torque, the zero speed torque, the motor can develop. The three other torque set points are based on the maximum torque specified in field 434.

Line segments 439A to 439D of plot 438 depict the profile of the speed-to-torque relation generated as a result of the plotting of the set point data in fields 428–434. Line segment 439A is extends from the from the speed/torque set point specified in the first, highest speed field, field 428, to the maximum speed/zero torque set point. As can be seen by plot 438, in preferred versions of the invention, this first speed/torque set point is selected so that line segment 439A is substantially vertical. Thus, when the motor is running at the maximum speed, the surgeon has some ability to generate a torque with the motor, bear down at a surgical site, without having the motor speed drop off.

Line segments 439B, 439C and 439D of plot 438 are shallow sloped diagonally plots. These plots are arranged so that as the torque generated by the motor increases the speed decreases at differing rates of deceleration. The diagonal profile of these plots thus ensure that as the torque generated by the motor increases the speed of the motor will slow at a rate which will be tactually sensed by the surgeon. This gives the surgeon the opportunity to manipulate the handpiece in such as to reduce the occurs of the motor being overdriven to the point where it stalls out. In the depicted plot 438, it can be seen that the slope of the individual line segments is such that at lower torque limits the maximum speed decreases relatively slowly and that at the maximum torque limit for the motor, represented by line segment 439D, the speed decrease is set to be quite pronounced. This later affect is intended to provide the surgeon with a sensory notice that the motor is producing the maximum amount of torque it can develop.

With regard to plot 438 it should also be recognized that the two points that define line segment 439D are the speed/torque set point data contained in the last intermediate field, field 432 and the zero speed/maximum torque point specified in field 434.

Field 442 contains data representative of the length of the reset, enable and delay pulses that are applied to the internal components of the console in order to ensure the correct start up of the motor. This field may also contain data indicating the maximum rate at which the motor should be allowed to accelerate. Field 444 contains data representative of the frequency of the braking signals should be applied to the motor, the period in which the braking signals should be applied to the motor and the braking signals that need to be applied to the motor in order to ensure its complete stopping. Field 444 may also contain data indicating the maximum rate at which the motor can be decelerated. The data in fields 442 and 444, in addition to controlling the starting and stopping of the motor are also useful in controlling its actuation when the motor is being driven in the oscillatory mode.

Field 446 contains data used to control the filtering of the current signal. Data used to control the filtering of the tachometer signal is contained in field 448. A field 449 contains what is referred to as time out data. The time out data contained in field 449 is used by the control console 36 to regulate the negation of the energization signals to the motor in the event the motor draws a current greater than that it should be drawing at any given instant. Field 450 contains resistor compensation data. The data in field 450 is used to establish the impedance of the speed feedback loop internal to the control console 36.

Field 451 a warm run definition for the handpiece. The warm run definition represents a internal handpiece temperature at which the handpiece would be considered running in a warm state. Field 452 contains a high current data about the handpiece. If during operation of the handpiece, the current draw of the handpiece exceeds the level specified in field, the handpiece is considered to be in a high current draw state. As will be discussed hereinafter, the data in fields 451 and 452 are used to facilitate the recordation of the operating history of the handpiece.

Fields 453 and 454 contain data useful for controlling any accessory units that may be used in conjunction with the handpiece. In one version of the invention fields 453 and 454, contain data relevant to the operating parameters of, respectively, the pump 40 and the bulb 248 integral with the light-and-water clip 45. More particularly, field 453 contains data indicating the maximum and minimum operating speeds of the pump 40 for the handpiece and the rate at which the speed of the pump can be incremented. Field 454 contains data indicating the maximum intensity of the bulb 248.

The data contained in fields 348–434 and 442–454 represent the encyclopedia data within NOVRAM 72.

Fields 458 and 460 represent the data fields that contain instructions regarding the image presented on the display 37 for operation of the handpiece 32. Field 458 is a screen type field that provides an indication of if the handpiece uses the standard image or, if not, the number of custom images it requires. Field 460 contains instructions for generating the custom images the handpiece requires. Field 460 thus contains the custom screen data. It should be recognized that, in practice, field 460 is both larger in size and contains more sub-fields than screen type field 458.

In the described version of the invention the data contained within fields 342–434 and 442–460 occupy approximately 500 bytes of memory and NOVRAM 72 has 2k bytes of memory. The excess memory in NOVRAM 72 makes it possible to write different versions of the data in different blocks within the NOVRAM. The capability of the NOVRAM 72 to hold multiple versions of the data is useful if, for example, during manufacture of the handpiece 32 an initial effort to write the data in the NOVRAM fails. Moreover, during the useful life of the handpiece 32 it may be desirable to provide NOVRAM 72 with new operating data. The new operating data may be required if, as a result of maintenance testing it is determined that the operating characteristics of the handpiece have changed.

The data stored in EEPROM 74 within handpiece 32 are now described by reference to FIG. 15. Field 466 is an odometer field. In the odometer field 466 data representative of the total time in second and/or minutes the motor 52 integral with the handpiece 32 has been actuated. This field is updated by the control console 36 during the operation of the handpiece 32. There is also a scheduled service field 467 in which an indication of when, in terms of total time of operation, the handpiece 32 should next be subjected to a preventive maintenance inspection. The data in the maintenance flag field 468 is set by personnel charged with the manufacture and maintenance of the handpiece 32.

When the handpiece 32 is attached to the control console 36, the control console compares the total time the handpiece 32 has been actuated from the odometer field 466 to the scheduled service field 467. If, as result of this comparison it appears that the handpiece 32 is approaching a point in its run time cycle at which maintenance will soon be required or is required, the console 36 will generate an appropriate message on display 37. The console 36 may also allow use of the handpiece 32 only if the surgeon makes it a specific acknowledgement that he/she is aware that the time period for performing maintenance on the handpiece is past due. A service history field 468 contains an indication in past run times, of when the last three services of the handpiece occurred.

EEPROM 74 also includes a maximum temperature field 469. Maximum temperature field 469 contains an indication of the maximum internal temperature of the handpiece 32 as monitored by temperature sensor 96 during the operation of the handpiece. When the control console 36 initializes the system 30 for use with the handpiece 32, the console retrieves the temperature data stored in the warm run field 454. If, during the use of the handpiece 32, the temperature of the handpiece exceeds the past highest temperature, control console 36 writes the new temperature into field 469. The data in the maximum temperature field 469 is then read from EEPROM 74 during the maintenance of the handpiece 32 in order to assist in the evaluation of whether or not the handpiece is operating within acceptable parameters.

EEPROM 74 also contains warm run time field 470 in which an indication of the total time the handpiece is run at a temperature exceeding that specified in the warm run definition field 454 is stored. There are also maximum current drawn and high current run time fields 471 and 472, respectively. Maximum current drawn field contains an indication of the instantaneous maximum current drawn by the handpiece. High current run time field 472 is used to store an indication of the total time of operation for the handpiece at which it draws a current that exceeds that specified in high current definition field 452.

The average speed at which the handpiece is run is stored in an average speed field 473. The total times the handpiece is plugged into a control console 36 is recorded in a times coupled field 474. EEPROM 74 also includes an override count field 475. Override count field 475 contains an indication of the number times a condition has arisen in which, in order for the handpiece to be operated, an override command must be entered through the control console.

Figure 16B:
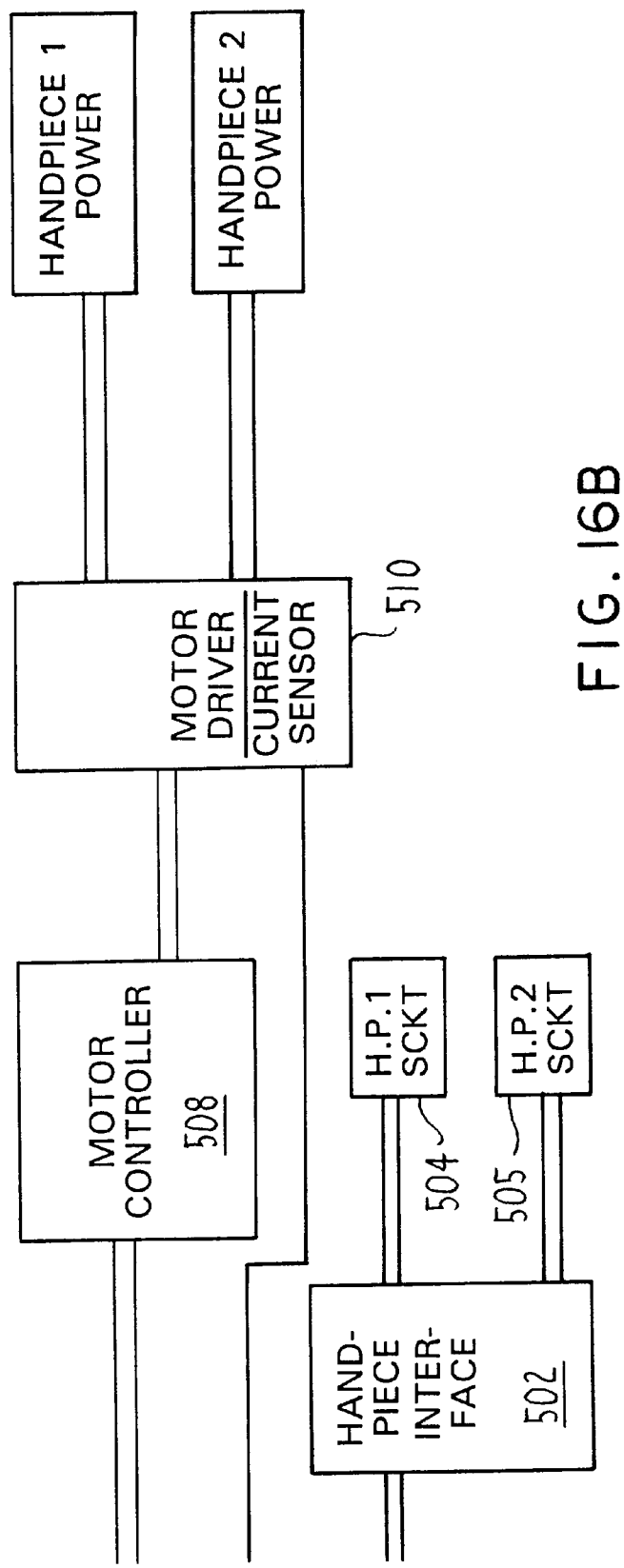

The basic structure of the control circuit internal to the control console 36 is now described by reference to the block diagram formed when FIGS. 16A and 16B are assembled together. A main controller 492 is responsible for overall control of the system 30. The main controller 492 is the component internal to the control console 36 that reads the data stored in the handpiece memories 72 and 74 and foot switch assembly memory 329 and that acts on the data stored in the memories. The main controller 492 receives input commands from a number of sources such as the sensor 94 that monitors hand switch 39, the foot switch pedals 44a, 44b, . . . and the touch screen display 37. Based on instructions embedded in the main controller 492, the retrieved data, the input commands and the signals from the sensors 94 and 96, the main controller 492 controls the application of energization signals to the handpiece 32, the pump 40, the intensity of the light emitted by the bulb 248 integral with light-and-water clip 45 and the information that is presented on the touch screen display 37.

The AC line voltage that is used by the control console 36 to both energize the handpiece 32 and the control console is initially converted into a 40 VDC signal by an AC-to-DC converter 494. In some preferred versions of the invention, the AC-to-DC converter 494 is a plug-in module that can be physically removed the body of the control console 36. This makes it possible to provide AC-to-DC converters 494 with different power ratings to be attached to the control console 36. For example, it could be possible to provide a 200 Watt Ac-to-DC converter or a 400 Watt converter depending on the power requirements of the handpieces 32 or 33 with which the console will be used. In these versions of the invention, the AC-to-DC converter 494 is configured to assert a POWER_SUPPLY_SENSE (PWR_SNS) signal to the main controller 492. The PWR_SNS signal provides the main controller 492 with an indication of the power rating of the AC-To-DC converter 494. This provides the main controller 492 with information it needs to determine if the control console 36 can supply the power required by a particular handpiece 32 or 33 attached to the console.

A temperature sensor 495 may be fitted inside some AC-to-DC converters 494. This sensor 495 could be located adjacent a critical, heat-generating part of the converter 495 such its transformer or power diodes. In the event the sensor 495 determines the converter 494 is overheating as may occur if large amounts of power are drawn for extended periods of time, or in the event of a component failure, the sensor will assert a signal to the main controller 492. In some versions of the invention, the signal asserted by temperature sensor 495 is a specific PWR_SNS signal. Also, it may be possible to send two different signals depending on the state of the sensor 495; a first PWR_SNS signal can be sent if the converter 494 is only starting to overheat and a second signal can be sent to indicate that the overheating has reached a critical stage. In converters 494 that supply relatively low amounts of power, for example, converters that draw 200 Watts or less of power, sensor 495 may not be required.

The 40 VDC is applied directly to a DC-to-DC voltage converter 496. Voltage converter 496 converts the 40 VDC signal into +12 VDC, +5 VDC and −5 VDC signals that are applied to other components of the control console 36 as energization signals. The 40 VDC is distributed from voltage converter 496 to the other components of the control console 36 over a 40 VDC rail 498. In order to minimize the complexity of the remaining block and schematic diagrams, only a few representative locations where the +12 VDC, +5 VDC and −5 VDC signals are needed are illustrated. The 40 VDC is also distributed through voltage converter 496 over a dedicated conductor as a MOTOR_POWER (MTR_PWR) signal which is applied to the active handpiece 32 or 33. The MOTOR_POWER signal originates from the output terminal of a relay 500 internal to voltage converter 496. The state of relay 500 is controlled by a signal generated by the main controller 492.

The data in the memories 72 and 74 internal to the handpieces 32 and 33, as well as the output signals from the sensors 94 and 96, (the devices), internal to the handpieces are supplied to the main controller 492 from a handpiece interface 502. Handpiece interface 502 is connected to the output terminals of the handpieces 32 and 33 through two separate handpiece sockets 504 and 505, respectively. The signals generated by the pedals 44a, 44b, . . . associated with the foot switch assembly 46 are supplied to the main controller through a foot switch interface 506.

The application of the energization signals to the handpiece is regulated by a motor controller 508. Motor controller 508 is connected to the main controller 492 so as to receive basic commands regarding the speeds at which the motor internal to the handpieces 32 and 33 should run and how the motor should be actuated. In response to receiving commands from the main controller 492, the motor controller 508 generates trigger commands to a motor driver and current sense circuit 510. Motor driver and current sense circuit 510 performs two basic functions. First, in response to the trigger commands generated by the motor controller 508, it selectively applies the MOTOR_POWER signal to the motor of the active handpiece 32 or 33. Secondly, the motor driver and current sense circuit 510 monitors the current applied to the motor of the handpiece 32. Signals representative of the sensed current are supplied to both the main controller 492 and the motor controller 508.

A display input/output controller 512 both controls the presentation of images on the touch screen display 37 and the generation of system commands based on the depression of the switch images presented on the display. The display input/output controller 512 receives the basic commands regard the particular image that should be presented on the touch screen display 37 from the main controller 492. Based on those commands, the display input/output controller 512 generates the specific bit-level commands that cause the desired image to be presented. The display input/output controller further monitors the touch screen display 37 to determine which of the switch images presented on the screen have been depressed and sends that information to the main controller 492.

A backlight and speaker controller 514 are also connected to the main controller 492. The backlight and speaker controller 514 controls the intensity and contrast of a fluorescent backlight 511 associated with the touch screen display 37 that provides the backlighting needed to make the image presented on the display visible. The backlight and speaker controller 514 also controls the generation of warning tones by a speaker 513. A pump controller 515 controls the application of energization signals to irrigation pump 40. When the pump 40 is designed as a module adapted to be fitted into control console 36, pump controller 516 may be integrally attached to the module in which the pump is installed.

Figure 17:
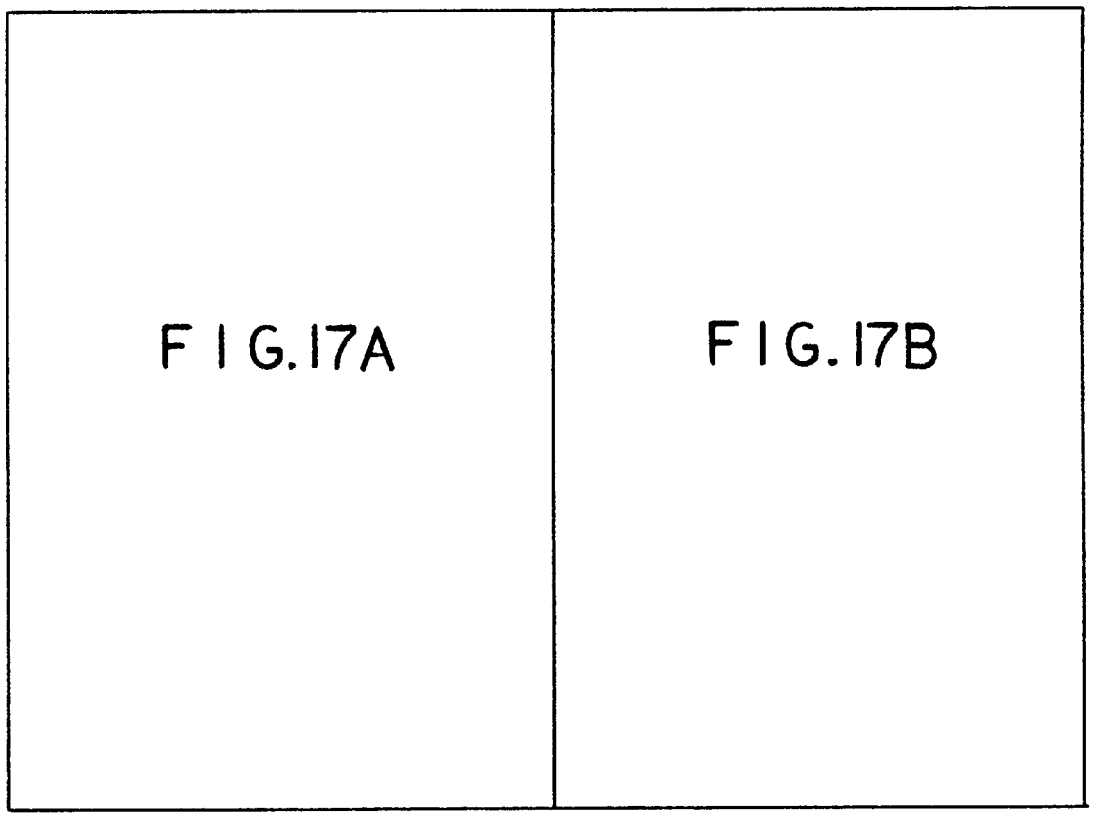
FIG. 17 is a blue print indicating how
Figure 17A:
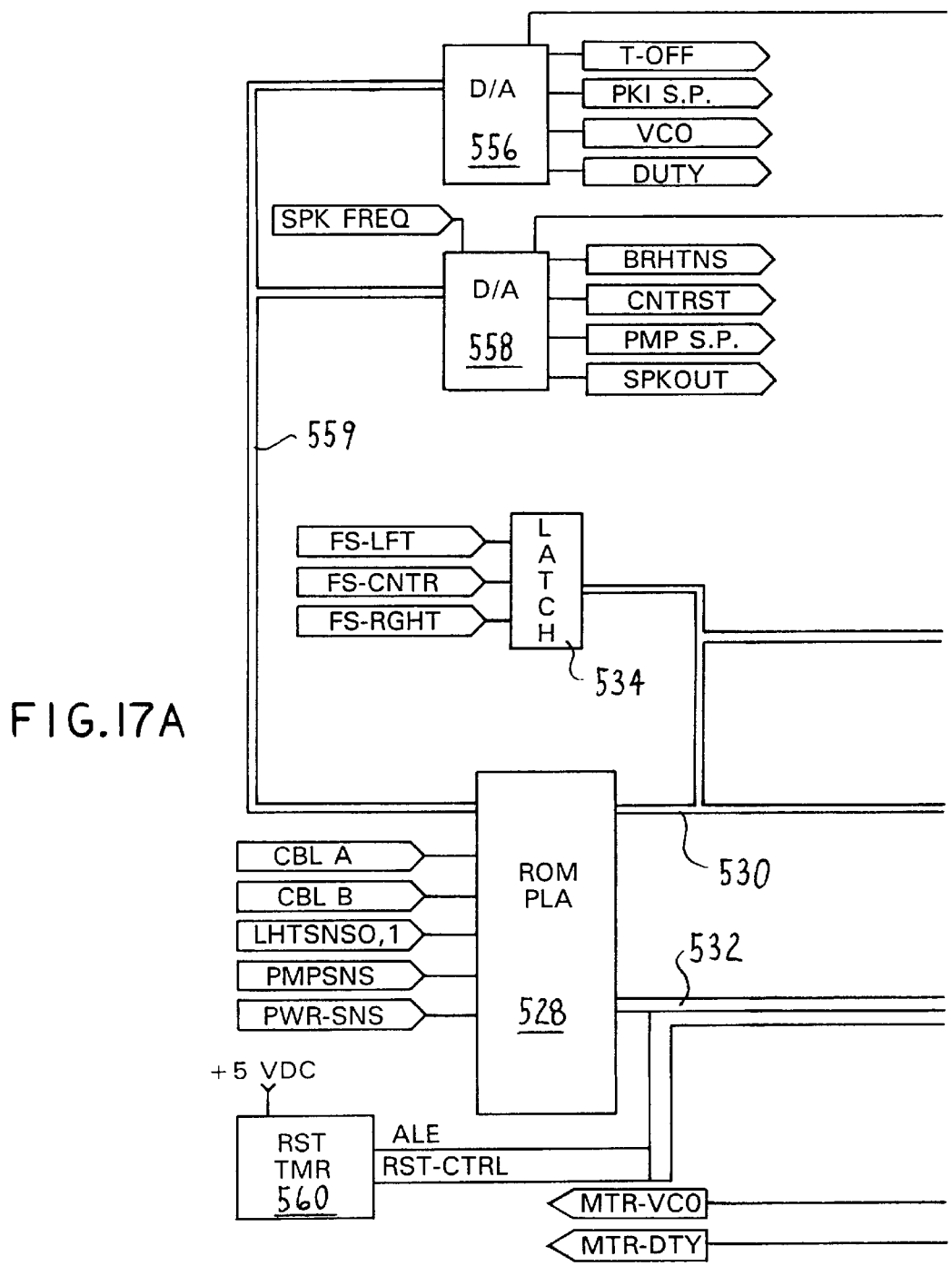
FIGS. 17A and 17B are assembled to form a block diagram of the main components of the main processor of the control circuit.
Figure 17B:
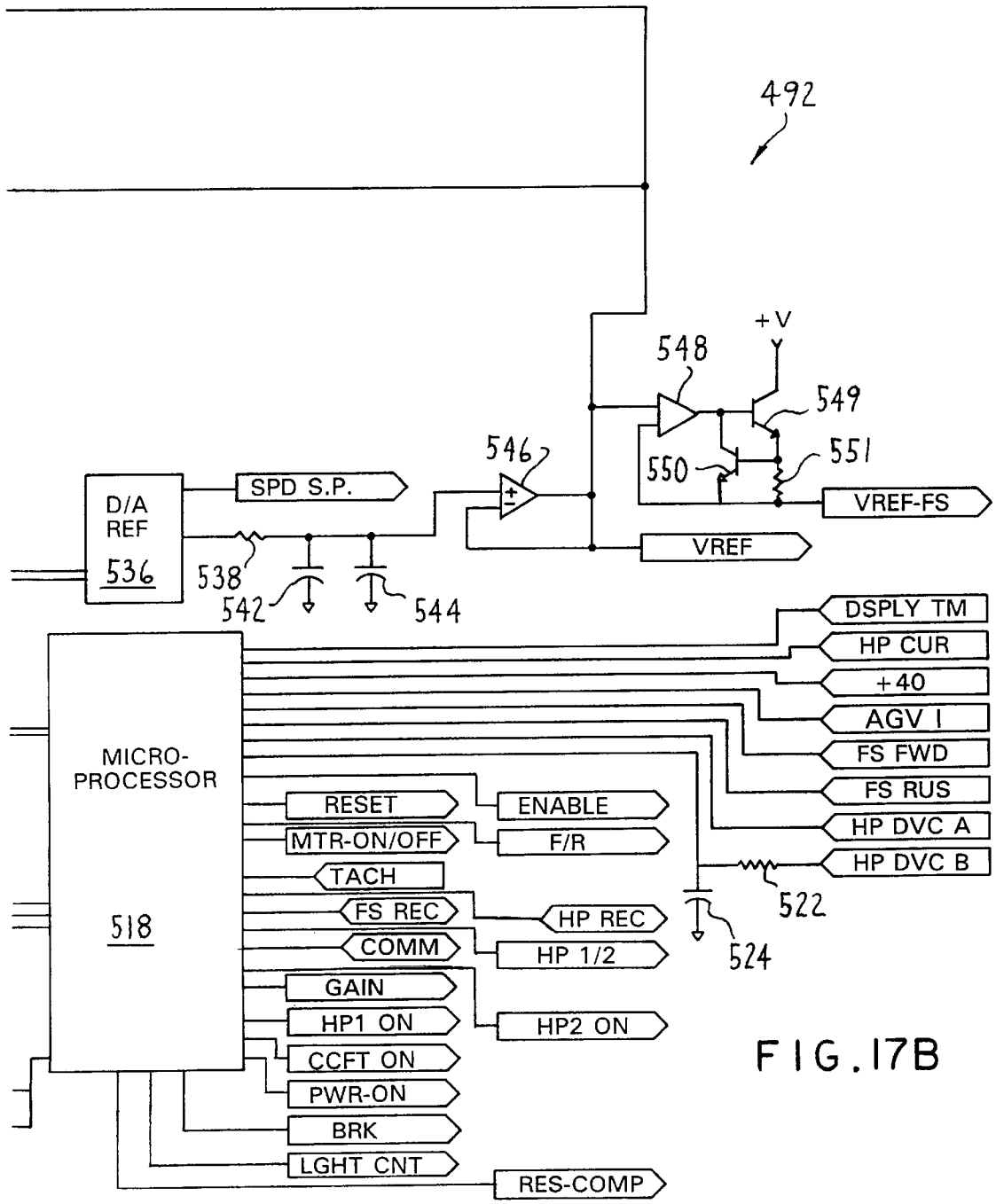

As seen by reference to FIGS. 17A and 17B, the main controller 492 includes a microprocessor 518. In the described version of the invention, microprocessor 518 is capable of exchanging both analog and digital signals with the complementary components forming the control console 36. One suitable microprocessor that can be employed as the microprocessor 518 of this invention is the 80C552 manufactured by Phillips Semiconductor. Microprocessor 518 retrieves the data stored in the memories 72 and 74 of handpieces 32 and 33 as HANDPIECE_RECOGNITION (HP_REC) signals from the handpiece interface 362. The handpiece interface 502 also provides microprocessor 518 with the signals generated by the devices A and B internal to the handpiece, HP_DVC_A and HP_DVC_B signals, respectively, and a signal representative of the current drawn by the devices internal to the handpiece, an HP_CUR signal. Microprocessor 518 provides the handpiece interface with an indication of which of the two handpieces 32 connected to the control console 36 should be considered the active handpiece with a digital HP_1/2 signal.

The data stored within memory 329 internal to the foot switch assembly 46 are provided to the microprocessor 518 through foot switch interface 506 as FS_REC signals. In the described version of the invention both the HP_REC and FS_REC signals are forwarded to microprocessor 518 over serial data buses. Microprocessor 518 also receives from foot switch interface 46 FOOTSWITCH_FORWARD (FS_FWD) and FOOTSWITCH_REVERSE (FS_RVS) signals that are representative of the signals generated as result of the depression of foot switch assembly pedals 44a and 44b, respectively.

Microprocessor 518 generates a set of signals to motor controller 508 for controlling the basic production of the motor energization signals. The digital signals include: a MOTOR_ON\OFF (MTR_ON\OFF) signal that provides a basic control of whether or not motor controller and current sense circuit 510 is able to generate the signals used to control the energization of the motor; RESET (RST) and ENABLE (ENB) signals that are cycled in order to control the initial generation of the energization signals; a FORWARD/REVERSE (F/R) signal that regulates the sequence in which the energization signals should be generated; and a BRAKE (BRK) signal that is asserted whenever the microprocessor 518 determines there is a need to generate energization signals that facilitate the deceleration of the motor 52 in the handpiece 32. Microprocessor 518 also generates an analog SPEED_SET_POINT (SPD_SP) signal to motor controller 508 that indicates the speed at which the motor 52 internal to the handpiece 32 is to be energized. Microprocessor 518 receives directly from motor controller 518 a variable frequency digital TACHOMETER (TACH) signal that is representative of motor speed.

Microprocessor 518 also selectively forwards to motor controller 508 a VCO signal, a MOTOR_VCO (MTR_VCO) signal, a DUTY signal and a MOTOR_DUTY (MTR_DTY) signal. These signals are asserted by microprocessor 518 when the control console 36 is used to be provide energization signals to a handpiece that is operated in a direct drive mode. A handpiece is operated in the direct drive mode when the energization signals applied thereto are not applied directly to a brush less, Hallless motor 52 such as contained within the described handpiece 32. For example, direct drive mode energization signals are provided to a handpiece that is functioning as charged battery pack for a specific type of surgical tool. Alteratively, direct drive mode energization signals are provided to handpieces wherein the actual tool is some type of motorless device such as a laser or an ultrasonic tool.

The VCO and DUTY signals are the actual signals asserted by microprocessor 518 to regulate the direct drive energization of the handpiece. These signals are multi-bit parallel signals. As discussed hereinafter, other components internal to the main controller 492 convert these signals into analog formats for their use by motor controller 508. The MOTOR_VCO and MOTOR_DUTY signals are asserted to control when the motor controller 508 is regulated by the VCO and DUTY signals. The MOTOR_VCO and MOTOR_DUTY signals are one-bit signals that are directly forwarded by microprocessor 518 to motor controller 508.

Separate HANDPIECE1_ON\OFF (HP1_ON) and HANDPIECE2_ON\OFF (HP2_ON) signals are generated by the microprocessor 518 to the motor driver and current sense circuit 510. The HANDPIECEx_ON\OFF signals are used to establish to which of the handpieces 32 or 33 the energization signals are applied. A RESISTOR_COMPENSATION (RES_COMP) signal is generated by microprocessor 518 to motor controller 508 to regulate the configuration of.the speed feedback loop internal to the motor controller 508.

Microprocessor 518 also generates PEAK_I_SET_POINT (PK_I_SP) and TIME_OFF (T_OFF) signals both of which are applied to the motor controller 508 to regulate the application of energization voltages to the motor 52. The PEAK_I_SET_POINT signal represents at any given instant the maximum current the motor 52 is allowed to draw. The TIME_OFF signal is used to establish the time out period in which the assertion of energization signals to the motor is negated after the drawn current exceeds the limit defined by the PEAK_I_SET_POINT signal. Both the PEAK_I_SET_POINT signal and the TIME_OUT signal are generated as multi-bit parallel signals. Other components of main controller 482 convert these signals into analog format signals for assertion to motor controller 508.

A two-bit GAIN signal is also generated by microprocessor 518. The GAIN signal is forwarded to the motor control and current sense circuit 510 for establishing the gain of an amplifier that processes the signal representative of the current drawn by the active handpiece 32 or 33. The GAIN signal, as described hereinafter, is set with the PEAK_I_SET_POINT signal.

Four multi-bit parallel signals are also generated by microprocessor 518 to control ancillary components of the system 30. These signals are: BRIGHTNESS (BRHTNS) and CONTRAST (CNTRST) signals that regulate the characteristics of the image presented on display 37; a PUMP_SET_POINT signal that represents the user-selected operating speed for pump 40; and a SPEAKER_OUT signal representative of a user-selected volume for the speaker 513. The other components of main controller 492 that convert these signals into analog format will be hereinafter described.

Microprocessor 518 receives from motor driver and current sense circuit 510 an AVERAGE_I (AVG_I) signal representative of the average current drawn by the motor 52 internal to the active handpiece 32 or 33.

Figure 19:
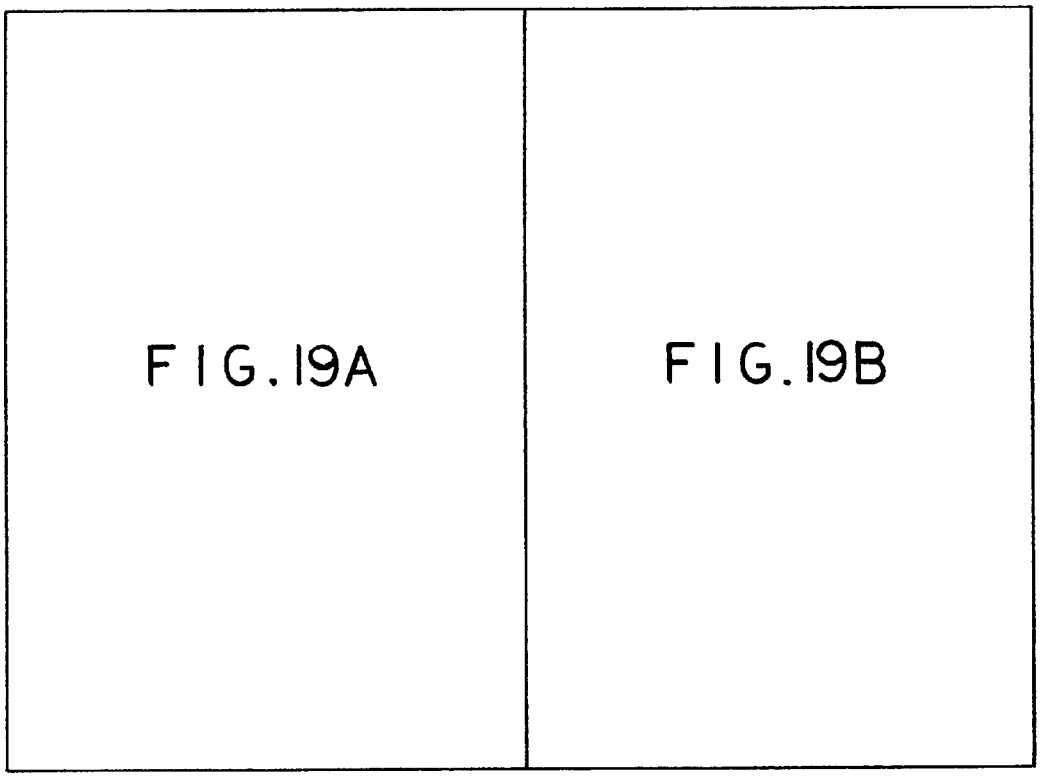
FIG. 19 is a block diagram illustrating how

Data signals representative of the images to be generated on the touch screen display 37 and of the commands entered through the display are exchanged between microprocessor 518 and the display input/output controller 512 over a communications (COMM) bus 520 (FIG. 19 A). In one version of the invention, communications bus 520 includes two simplex serial communications lines along with an enable line over which control signals regulating the writing on to and reading from the communication lines are transmitted.

The on/off state of two of the lights that form part of the system 30 are controlled directly by microprocessor 518. Microprocessgor 518 generates a LIGHT_CONTROL (LGHT_CNT) signal to regulate the on/off state and intensity of the bulb 248 mounted to the active handpiece 32 or 33 through handpiece interface 502. A CCFT_ON signal that regulates the on/off state of the fluorescent backlight 511 associated with the touch screen display 37 is selectively generated by the microprocessor 518 to the backlight and speaker controller 514.

Microprocessor 518 both monitors the 40 VDC signal produced by AC-to-DC converter 494 and controls the state of the relay 500 that regulates the transmission of the 40 VDC signal as the MOTOR_POWER signal. The 40 VDC signal is applied to microprocessor 518 over the 40 VDC rail 498. Normally, microprocessor 518 asserts a MOTOR_POWER_ON (PWR_ON) signal to the relay 500 to close the relay so that the 40 VDC is applied to the motor driver and current sense circuit as the MOTOR_POWER signal. If, however, microprocessor 518 determines that the 40 VDC either falls below or rises above predefined tolerance limits, it will interpret the voltage fluctuation as a fault condition. If this determination is made, microprocessor 518 negates the assertion of the MOTOR_POWER_ON signal so as to prevent the application of any energization signals to the handpieces 32 or 33. Micrcoprocessor 518 will also negate the MOTOR_POWER_ON signal if it detects any other critical faults within the system 30.

In the illustrated version of the invention, microprocessor 518 also receives from the display input/output controller a DISPLAY_TEMP (DSPLY_TMP) signal representative of the signal of the touch screen display 37. The DISPLAY_TEMP signal is used by the microprocessor 518 to perform real time adjustments of the contrast of the display 37 in order to compensate for changes in contrast that occur as a result of the fluctuations in the temperature of the display.

As shown with regard to the HP_DVC_B signal, the analog signals received directly by microprocessor 518 are applied to the microprocessor 518 through a load resistor 522. A capacitor 524 is tied between the junction of the load resistor 522 and the microprocessor 518 in order to filter any unusual voltage variations from the received signal. Similar load resistors and filter capacitors, though not illustrated, are used to process the many, if not all, of the other analog signals applied to microprocessor 518.

Main controller 492 also includes a ROM-PLA 528 that is connected to microprocessor 518. ROM-PLA 528 stores the instructions microprocessor 518 retrieves in order to determine the processing functions it is to execute. One ROM-PLA 528 employed in control console 36 is the PSD311 manufactured by WSI. ROM-PLA 528 also receives some digital input signals from other components forming the control console 36 and generates digital output signals that are processed by other components forming the main controller 492. The primary data and address exchange between microprocessor 518 and ROM-PLA is over a main processor address-and-data bus 530. The signals that control of the reading of data from and writing of data to the ROM-PLA 528 are exchanged between microprocessor 518 and the ROM-PLA over a read-write control bus 532.

In the depicted version of the invention, ROM-PLA 528 receives as inputs CABLE_A (CBL_A) and CABLE_B (CBL_B) signals that indicate whether or not a cable 43 or 47 is attached to the sockets on the face of the control console 36. If a cable 43 or 47 is plugged into a socket, the short circuit across the two tied together contact pins 179 (FIG. 11) is detected and recognized by the main controller 492 as an indication of an attached cable.

ROM-PLA 528 receives from the handpiece interface 502 a LIGHT_SENSE (LHT_SNS) signal. This signal indicates whether or not a light clip is attached to the active handpiece 32 and, if there is, whether or not the bulb is functioning. In the depicted version of the invention, the LIGHT_SENSE signal is a two-bit signal. A PUMP_SENSE (PMP_SNS) signal is supplied to the ROM-PLA 528 from the pump controller 515 whenever a pump 40 is connected to the system 30.

The PWR_SNS signal, depicted as a multi-bit signal, is supplied from the AC-to-DC converter to the ROM-PLA 528. The PWR_SNS signal is used by the microprocessor 518 and the ROM-PLA 528 determine the amount of power the AC-to-DC converter 494 can supply. The PWR_SNS signal also contains an indication of temperature of the converter 494. In the event the PWR_SNS signal indicates that the temperature internal converter 494 rises above a warning level, microprocessor 518 causes the display 37 to generate a warning message, If the PWR_SNS signal indicates the converter temperature rises above a critical level, microprocessor and ROM-PLA 528 cease energization of the handpieces and causes a message to generated to indicate the cause of the system 30 shutdown.

Microprocessor, 518 also supplies to ROM-PLA 528 over bus 530 the PEAK_I_SET_POINT, TIME_OFF, DUTY, VCO, BRIGHTNESS, CONTRAST, PUMP_SET_POINT and SPEAKER_OUT signals generated by the microprocessor. A parallel-to-serial converter internal to ROM-PLA 528 converts these signals into digital pulses that are outputted through a single output line.

Status signals that indicate whether or not a particular pedal 44c, 44d or 44e that is part of the foot switch assembly 46 has been depressed are supplied to the microprocessor 518 through a latch 534. The latch 534 receives from the foot switch interface 506 signals FS_LFT, FS_CNTR and FS_RGHT indicating whether or not a particular pedal 44c, 44d or 44e, respectively, has been depressed. The signals are supplied from the latch to the microprocessor 518 over the main processor address-and-data bus 530.

Main controller 492 further includes a dedicated digital-to-analog converter 536 that continually generates a SPEED_SET_POINT (SPD_SP) signal that is representative of the user-desired speed the motor 52 internal to the active handpiece 32 or 33. Digital-to-analog converter 536 is connected to the main processor address-and-data 530 bus for receiving a digital signal from microprocessor 518 upon which the SPEED_SET_POINT signal is based. In one preferred version of the invention, the digital signal is a 12-bit signal and the address-and-data bus 530 only has 8 data lines. In these versions of the invention, the most significant 8 bits of the signal are initially latched into digital-to-analog converter 536 and then the remaining 4 least significant bits are latched into the converter.

In the depicted version of the invention, digital-to-analog converter 536 also generates an analog VREF signal which serves as a reference voltage for other components internal to the control console 36. The basic reference signal produced by the digital-to-analog converter 536 initially is applied to a resistor 538. The signal is then tied to ground through two capacitors 542 and 544 in order to filter out any variations in the signal. The filtered signal is applied to the noninverting input of an amplifier 546. The output signal from amplifier 546 functions as the basic VREF signal. The VREF signal is applied as feedback to the inverting input of amplifier 546 so that the amplifier 46 functions as low impedance buffer.

The VREF signal produced by amplifier 546 is applied to the noninverting input of amplifier 548. The output signal from amplifier 548 is applied to the base of an NPN transistor 549 and the collector of NPN transistor 550. The collector of transistor 549 is tied to the +12 VDC voltage source and its emitter is tied to the base of transistor 550. A VREF_FS, a reference signal that is supplied to the foot switch assembly 46, is then taken off a resistor 551 also tied to the base of transistor 549. The VREF_FS signal is also supplied as a feedback signal to both the inverting input of amplifier 548 and the emitter of transistor 550.

The main controller 492 thus provides a precision, low-impedance VREF_FS signal to the foot switch assembly 46 from a source that is separate from the source of the primary VREF signal. Amplifier 548 provides overload protection for the VREF_FS signal. Thus, in the event there is a short in either the foot switch assembly 46 or in the cable connecting the foot switch assembly to the control console 36, the affects of the short are isolated from the other components of the control console.

Main controller 492 further includes two combined multiplexed digital-to-analog converters 556 and 558. Digit-to-analog converters 556 and 558 are connected to the ROM-PLA 528 to receive the pulse signal representations of the PEAK_I_SET_POINT, TIME_OFF, DUTY, VCO, BRIGHTNESS, CONTRAST, PUMP_SET_POINT and SPEAKER_OUT signals generated thereby and to selectively convert these signals into their analog equivalents. The ROM-PLA 528 connection to converters 556 and 558 is over a dedicated converter bus 559. Based on the clock signals received in conjunction with the pulse signals, digital-to-analog converter 556 converts the PEAK_I_SET_POINT, TIME_OFF, DUTY, VCO signals into their analog equivalents. Digital-to-analog converter 558 converts the BRIGHTNESS, CONTRAST, PUMP_SET_POINT and SPEAKER_OUT, and PEAK_I_SET_POINT signals into their analog equivalents.

One conductor of converter bus 559 is a serial data conductor, not identified, that serves as the conductor over which the eight digital pulse signals are sent from ROM-PLA 528 to both converters 556 and 558. Command signals sent by ROM-PLA 528 over other conductors forming converter bus 559 simultaneously with the pulse signals control the assertion of the individual signals produced by converters 556 and 558.

The amplitude of the analog signals generated by converters 556 and 558 are set by reference to reference signals. The VREF signal produced by digital-to-analog converter 536 serves as the reference signal upon which the PK_I_SP, T_OFF VCO, DUTY, PMP_SP, BRHTNS and CNTRST signals are based. The reference signal for the SPKR_OUT signal is a SPEAKER_FREQUENCY (SPKR_FREQ) signal that is produced by the display input/output controller 512. Since the volume signal produced by the analog conversion of the volume control signal is modulated by the SPKR_FREQ signal, the resultant SPKR_OUT signal is an analog audio drive signal that is applied, after amplification, to the speaker 513 in order to cause the generation of the desired audio tones.

The main controller 492 also has a reset timer 560 that functions as a failsafe reset circuit. Reset timer 560 monitors the state of an address latch enable (ALE) signal that is transmitted from microprocessor 518 to the ROM-PLA 528 over read-write control bus 532. In the event reset timer 560 determines the address latch enable signal remains in one particular state beyond a predetermined time period, the reset timer asserts a RESET_CONTROLLER (RST_CTRL) signal. The RESET_CONTROLLER signal is forwarded to microprocessor 518, ROM-PLA 528 and to the display input/output controller 512 to initiate the start of a control console 36 reset sequence. In the depicted version of the invention, the RESET_CONTROLLER signal is forwarded to microprocessor 518 and all other components that respond to this signal over a branch of the read-write control bus 532.

Reset timer 560 is also tied to the rail over which the +5 VDC is distributed. In the event the +5 VDC drops below a given value, in one version of the invention, +4.5 VDC, reset timer 560 will also assert the RESET_CONTROLLER signal.

Figure 18A:
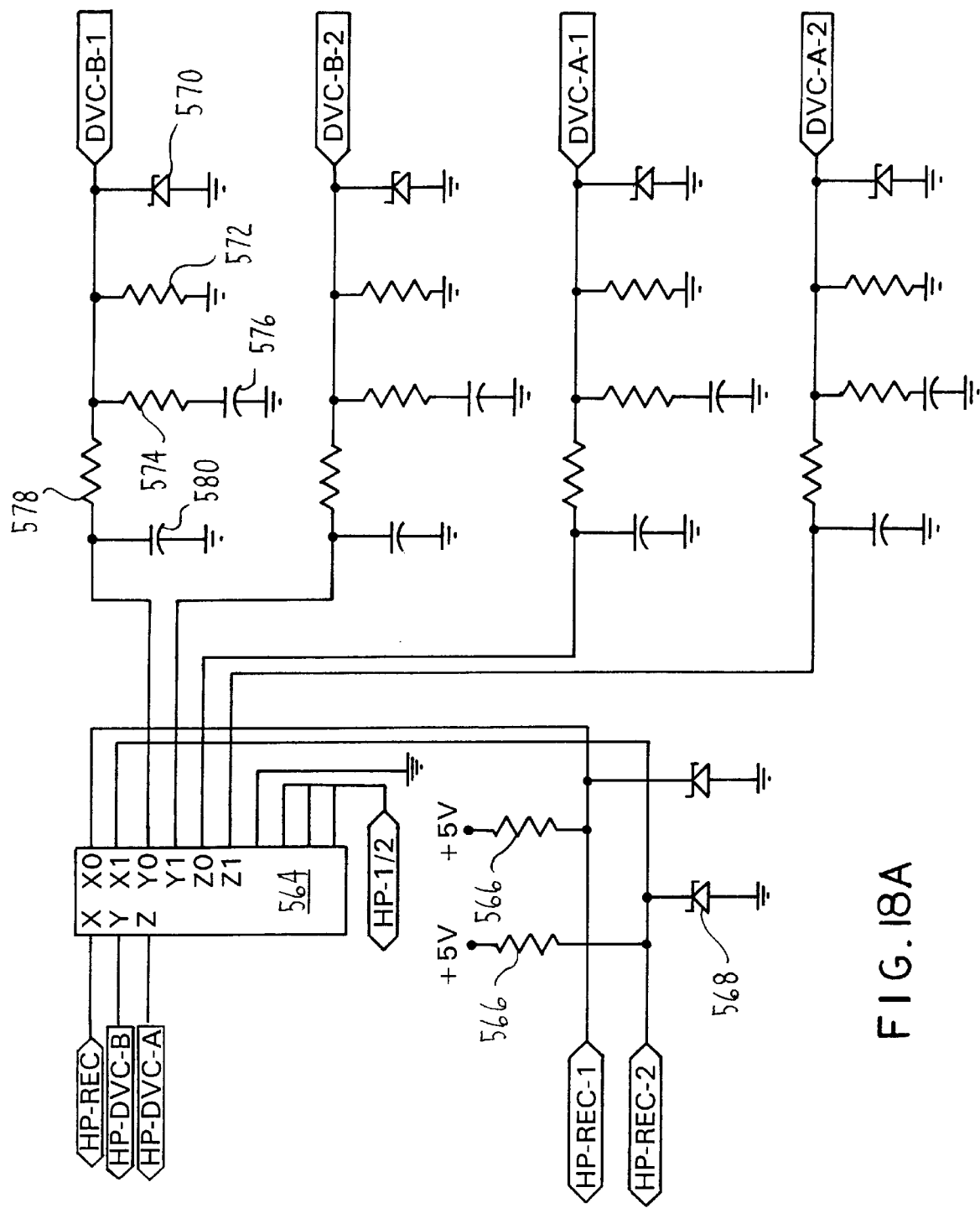
FIGS. 18A, 18B and 18C are schematic diagrams of the components forming the handpiece interface of the control circuit.

FIG. 18A is a schematic diagram of the components of the handpiece interface 502 that retrieve the data stored in the memories 72 and 74 internal to the handpieces 32 and 33 and that read the signals generated by the devices incorporated into the handpieces. A multiplexer 564 connects the microprocessor 518 to the active one of the two handpieces 32 connected to the control console 36. The connection established by multiplexer 564 is determined by the state of the HP_1/2 signal that is asserted by microprocessor 518. Attached to the side of the multiplexer directed towards the handpieces 32 are two identical signal paths over which the HP_RECx signals containing the stored data are supplied to the microprocessor 518. Each signal path includes a pull-up resistor 566 that is; tied to the +5 VDC voltage source. A surge suppressor 568, schematically represented as a reverse biased zener diode, is between resistor 566 and prevent excessive voltages from being applied to the handpiece 32 or 33.

The circuit of FIG. 18A further includes for signal paths over which the signals from the four devices, (two devices associated with each of the two handpieces 32 and 33) are applied to the input terminals of multiplexer 564. As now can be seen by reference to the signal path over which the DVC__B__1 signals, the signals generated by device B of the first handpiece 32, travel, each signal path includes a surge suppressor 570 immediately down line of the point the signal is introduced into the signal path. A pull down resistor 572 is tied in parallel across diode 570. A resistor 574 and series connected capacitor 576 are further connected in parallel between the signal path and ground to further signal generated by the device internal to the handpiece. The signal path further includes a current limiting resistor 578 through which the device signal flow into the input terminal of the multiplexer 564. A capacitor 580 is connected between resistor 578 and multiplexer 564 that is tied to ground provides additional filtering of the DVC__x__x signal. Multiplexer 564 produces three output signals: the HP__REC signal, the HP__DVC__A signal and the HP__DVC__B signal. The handpiece 32 or 33 from which these signals are supplied is a function of the HP__1/2 signal.

Figure 18B:
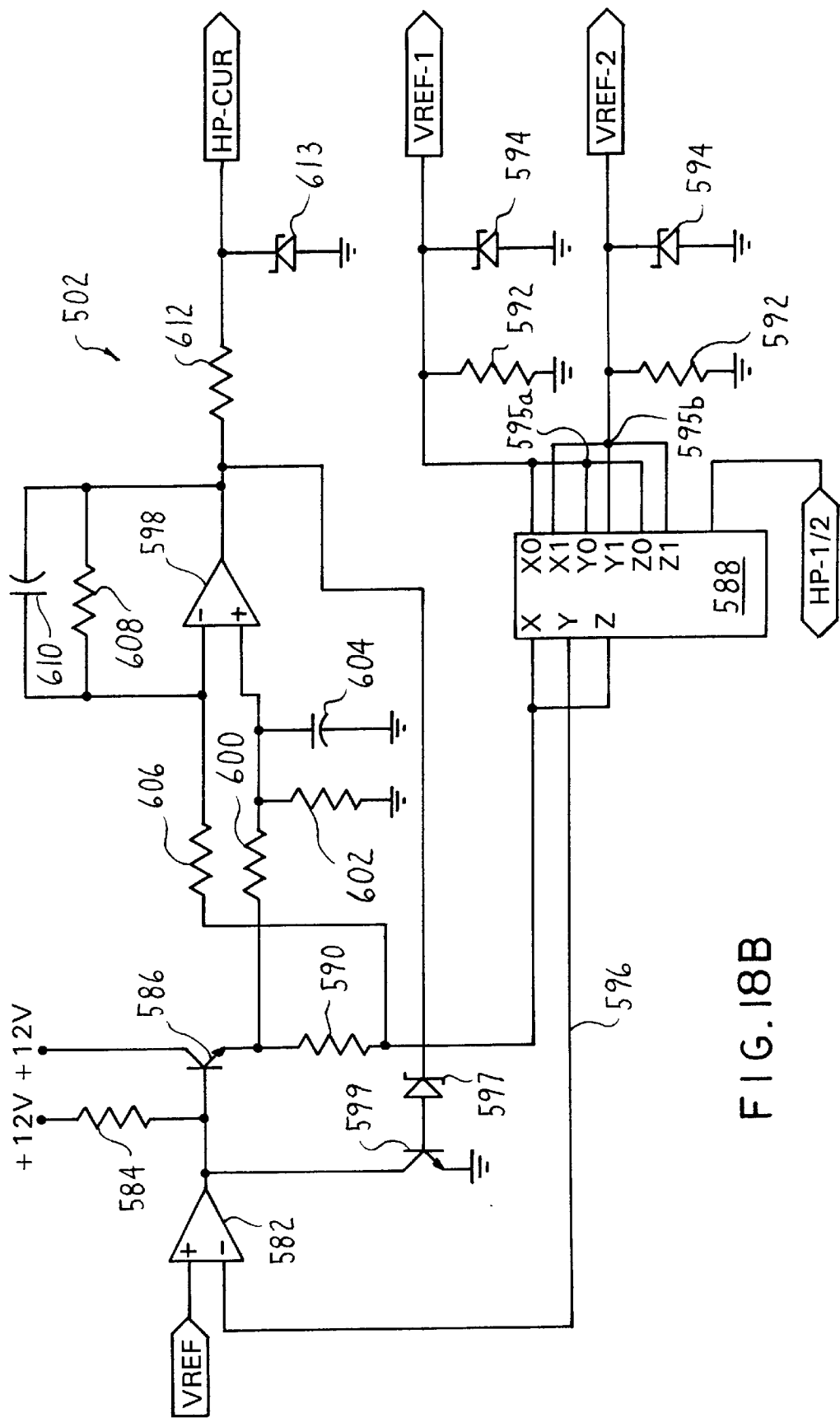

FIG. 18B illustrates the components of the handpiece interface 502 that both supply the reference voltage to the active handpiece 32 or 33 and that generate the HP__CUR signal. The V__REF signal produced by the main controller 492 is applied to the noninverting input of an operational amplifier 582. A pull-up resistor 584 is tied between +12 VDC voltage source and the output of the amplifier 582. The output of the amplifier 582 is applied directly to the base of an NPN transistor 586. As will be described hereinafter, the output VREFx signal applied to the actuated handpiece 32 or 33 is fed back to the inverting input of amplifier 582 to ensure that it remains constant.

The emitter of transistor 586 is tied to the +12 VDC voltage supply. The base of transistor 586 is tied to an input terminal of a multiplexer 588 through a resistor 590. Multiplexer 588 controls to which of the two handpieces 32 or 33 the power boosted VREFx signal is supplied. In the depicted version of the invention, the reference signal is applied to the active handpiece 32 or 33 across two channels in the multiplexer 588. This parallel routing of the reference signal is performed to minimize the effect of the internal resistance of the multiplexer 588 on the reference signal. Two signal paths, one to each of the handpieces 32 and 33, are attached to the multiplexer output ports that complement the input terminals to which the VREF__x signal is supplied. As seen by reference to the signal path over which the VREF__1 signal, the reference voltage to the first handpiece travels each signal path includes a pull down resistor 592. A surge suppressor 594 is connected in parallel across resistor 592. The VREF__x signal is then applied to the handpiece 32 or 33 to energize the devices internal to the handpiece. For example, if the V__REF signal is applied to handpiece 32, the signal is used as the reference signal by both the Hall effect sensor 94 and temperature sensor 96 internal to the handpiece.

A feedback line 596 is connected between nodes 595a and 595b from which the VREF__x signal is applied to the handpiece 32 or 33 and the inverting input of amplifier 582 so as to form a Kelvin connection. Feedback line 596 starts at the nodes, 595a or 595b on the output side of multiplexer 588, the side of the multiplexer closest to the handpiece. Feedback line 596 then goes back through a third channel of multiplexer 588 into the inverting input of amplifier 582. When the system 30 is in operation, amplifier 582 monitors the difference between the VREF signal from the main controller 492 and the VREF__x signal applied to the active handpiece 32 or 33. Based on this comparison, amplifier 582 drives transistor 586 to ensure that the VREF__x signal stays constant. During this signal monitoring, owing to the high impedance of amplifier 582, the relatively low resistance to which the feedback signal is exposed as it flows through multiplexer 588 can be ignored.

Resistor 590 functions as current sensor that monitors the current drawn by the active handpiece 32 or 33 as a result of the application of the VREF__x signal. The signal present at the junction of transistor 586 and resistor 590 is applied to the noninverting input of an amplifier 598 through a resistor 600. A resistor 602 and a capacitor 604 are connected in parallel between the noninverting input of amplifier 598 to respectively, divide and filter the filter the voltage presented to the amplifier. The VREF__x signal, the signal present at the junction between resistor 590 and multiplexer 588, is applied to the inverting input of amplifier 598 through a resistor 606. A resistor 608 and a capacitor 610 are connected in parallel between the output of amplifier 598 and the inverting input to cause the amplifier to produce a varying average signal representative of the current drawn by the devices internal to the active handpiece.

The output signal produced by amplifier 598 is supplied to a resistor 612 wherein the signal then functions as the HP__CUR signal. A surge suppressor 613 tied to ground clamps the HP__CUR signal to an acceptable, maximum voltage.

The output signal from amplifier 598 is also applied to reverse biased zener diode 597. The opposed end of diode 597 is tied to the base of an NPN transistor 599. The collector of transistor 599 is tied to the output of amplifier 582; the emitter of the transistor is tied to ground. In the event the signal produced by amplifier 598 indicates the handpiece is drawing an excessive current, diode 597 is forced into conduction so as to close transistor 599. The closing of transistor 599 shorts the application of the VREF signal to the handpiece.

Figure 18C:
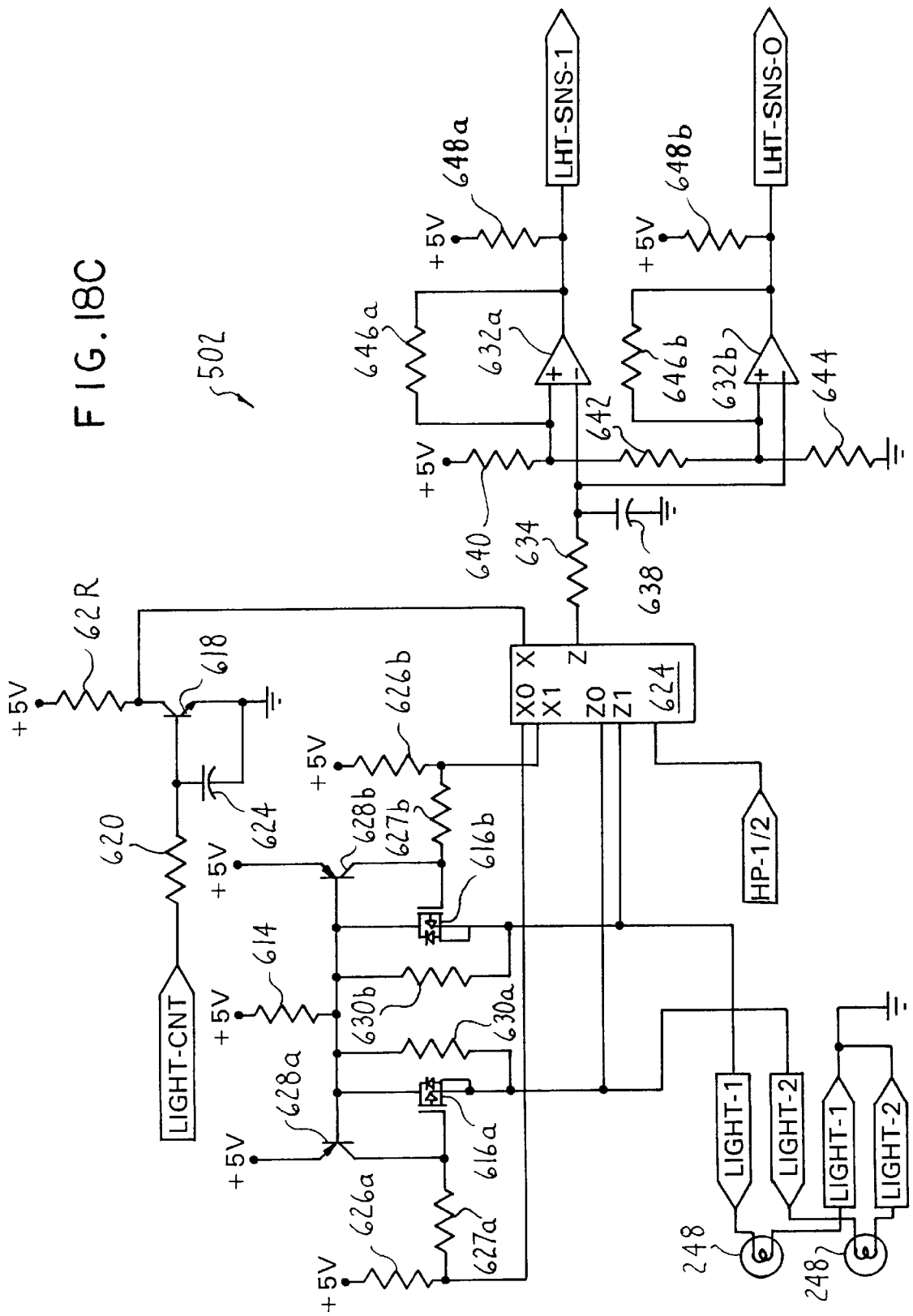

FIG. 18C is a schematic diagram of the portion of the handpiece interface 502 that energizes and monitors the state of the bulbs 248 integral with the light-and-water clips 45 that may be attached to the handpieces 32 and 33. In the depicted system 30, the intensity of the light illuminated by a bulb 248 is controlled by applying a pulse-width modulated energization signal to the bulb. Since separate light-and-water clips 45 attached to both handpieces 32 and 33 may be provided, handpiece interface 502 has two energization sub-circuits for selectively energizing the bulb 248 associated with each handpiece. Since the energization sub-circuits are identical, duplicate description of their identical feature will hereinafter be minimized.

The bulb energization voltage is taken from the +5 VDC voltage source through a resistor 614 that is common to both energization sub-circuits. The energization signal is applied to the bulb 248 as a LIGHT__1 signal through a control FET 616a capable of rapidly cycling on and off. The control FET 616a is switched by the LIGHT__CONTROL signal from the microprocessor 618. The LIGHT__CONTROL signal is initially applied to the base of an NPN transistor 618 through a resistor 620. The collector of transistor 618 is tied to the +5 VDC voltage source through a resistor 622. A capacitor 624 is tied between the base of transistor 622. Collectively, resistor 620 and capacitor 624 damper the slope of the pulse width modulated signal used to energize the bulb so as to minimize the electromagnetic interface generated by this signal.

FET 616a is a p-channel FET that is normally pulled high by the +5 VDC signal that is applied to the gate of the FET 616a through resistors 626a and 627a. The signal applied to FET 616a thus keeps the FET in the off, non conducting, state. The output signal at the collector of transistor 618 is used to turn on a selected one of the FETs 616a or 616b. The FET 616a or 616b turned on by the collector output signal is controlled by a multiplexer 624. The particular FET 616a or 616b to which the multiplexer 624 applies the signal is controlled by the HP_1/2 which sets the switch state of the multiplexer. This collector output signal is, for example, applied to the junction of resistors 626a and 627a so as to drive the voltage of the gate of FET 616a below the source voltage so as to turn on the FET. The assertion of the LIGHT_CONTROL signal by the microprocessor 518 thus causes the FET 616a or 616b to which the signal is applied to cyclically turn on and off. The cyclic turning on of the FET 616a or 616b causes the energization voltage to be applied to the associated light-and-water clip bulb 248.

The energization sub-circuits are further constructed to prevent excess current from being drawn by the associated light-and-water clips 45 in the event there is an electrical malfunction in the clips. Resistor 614 has a relatively low resistance, typically under 10 ohms. A PNP transistor 628a between resistor 614 and FET 616a so that base of transistor 628a is tied to the resistor-source junction and the collector of the transistor 628a is tied to the gate of the FET 616a. The emitter of transistor 628a is tied to the +5 VDC voltage source. In the event there is a short circuit down line from FET 616a, the voltage across resistor 614 will rise to above the turn on level for transistor 628a. The turning on of transistor 628a results in the application of an overdrive voltage to FET 616a which causes the FET to turn off and the application of the energization signal to the light-and-water clip 45 to cease. This current limit circuit also prevents excess current from being applied to the light-and-water clip when the bulb 248 is initially actuated. Moreover, a surge suppressor, (not identified,) is connected between FET 616a and ground.

The circuit of FIG. 18C also provides an indication of the clip/no-clip and good bulb/bad bulb state of the associated handpieces 32 and 33. These states are determined by making an inferential measurement of the resistance between the point where the signal from the handpiece interface 502 is applied to the light-and-water clip 45 and the point where the signal is returned to ground. If there is a clip 45 installed and a good bulb 248 in the clip, the resistance is approximately one ohm. If the clip 45 has a bad bulb, the resistance is approximately 400 ohms. If there is no clip in place or a no bulb within the clip, there is an infinite resistance across this circuit path.

In order to measure this resistance, an intermediate resistance, approximately 400 ohms, resistors 630a and 630b are connected from the +5 VDC voltage source and across FETs 616a and 616b. When the LIGHT_CONTROL signal is not being asserted, the voltages across these resistors are measured to provide an indication of bulb resistance, which indicates bulb state.

The measurement of the voltage across resistor 630a or 630b is made by two identical comparators 632a and 632b that are selectively tied to one of the resistors through multiplexer 624. Comparators 632a and 632b collectively produce the two-bit LIGHT_SENSE signal. More particularly, the end of the selected resistor 630a or 630b distal from the +5 VDC voltage rail is applied to the inverting inputs of both comparators 632a and 632b through a resistor 634. Voltage spikes in the signal from FET 616a or 616b are removed by a capacitor 638 tied between the inverting inputs of comparators 632a and 632b and ground. The noninverting inputs of the comparators are tied to a voltage divider which consists of series connected resistors 640, 642 and 644. One terminal of resistor 640 is tied to the +5 VDC and the other terminal is tied to resistor 646. Resistor 644 is tied between resistor 642 and ground. The noninverting input of comparator 632a is tied to the junction of resistors 640 and 642. The noninverting input of comparator 632b is tied to the junction of resistors 642 and 644.

Feedback resistors 646a and 646b are, respectively, tied between the outputs and noninverting inputs of comparators 632a and 632b. Pull-up resistors 648a and 648b are, respectively, tied between the +5 VDC source and the outputs of comparators 632a and 632b so as to produce cause the comparators to collective produce the two-bit LIGHT_SENSE signal. If there is no light-and-water clip 45 or no bulb 248 attached to the selected handpiece 32 or 33, comparators 632a and 632b are presented with an open loop-zero voltage condition. Consequently, comparators 632a and 632b combine to assert a first LIGHT_SENSE signal indicative of a no-clip/no-bulb state. If there is a clip 45 installed and the bulb is good, the low resistance of the bulb causes the comparators to assert a second LIGHT_SENSE signal indicative of clip-in/good-bulb state. If there is a clip installed but the bulb is bad, the higher resistance of this state over the good-bulb state will cause the comparators to assert a third LIGHT_SENSE signal indicative of a clip-in/bad-bulb state.

The foot switch interface 506 contains components for the analog processing of the signals from the foot switch assembly 46 that are similar to those described with respect to FIG. 18A for the handpiece interface 502. Resistors, capacitors and surge suppressors similar to those used to process the DVC_x_x signals from the handpieces are used process the signals that result from the depression of pedals 44a and 44b so as to produce the FS_FWD and FS_RVS signals. Surge suppressors, filter capacitors and pull-up resistors are used to preprocess the analog signals generated as a result of the depression of pedals 44c, 44d and 44e so as to respectively produce the FS_LFT, FS_CNTR and FS_RGHT signals. A circuit similar to that used to process the HP_RECx signals is used to process the signals exchanged with the memory 329 internal to the foot switch assembly 46 in order to facilitate the exchange of the FS_REC signals.

In some preferred versions of the invention, the VREF_FS signal is not applied to the foot switch assembly 46 through the foot switch interface 506. Instead, a dedicated conductor in the control console 36 is used to apply the VREF_FS directly to an appropriate socket opening on the face of the control console, conductor not illustrated.

Figure 19A:
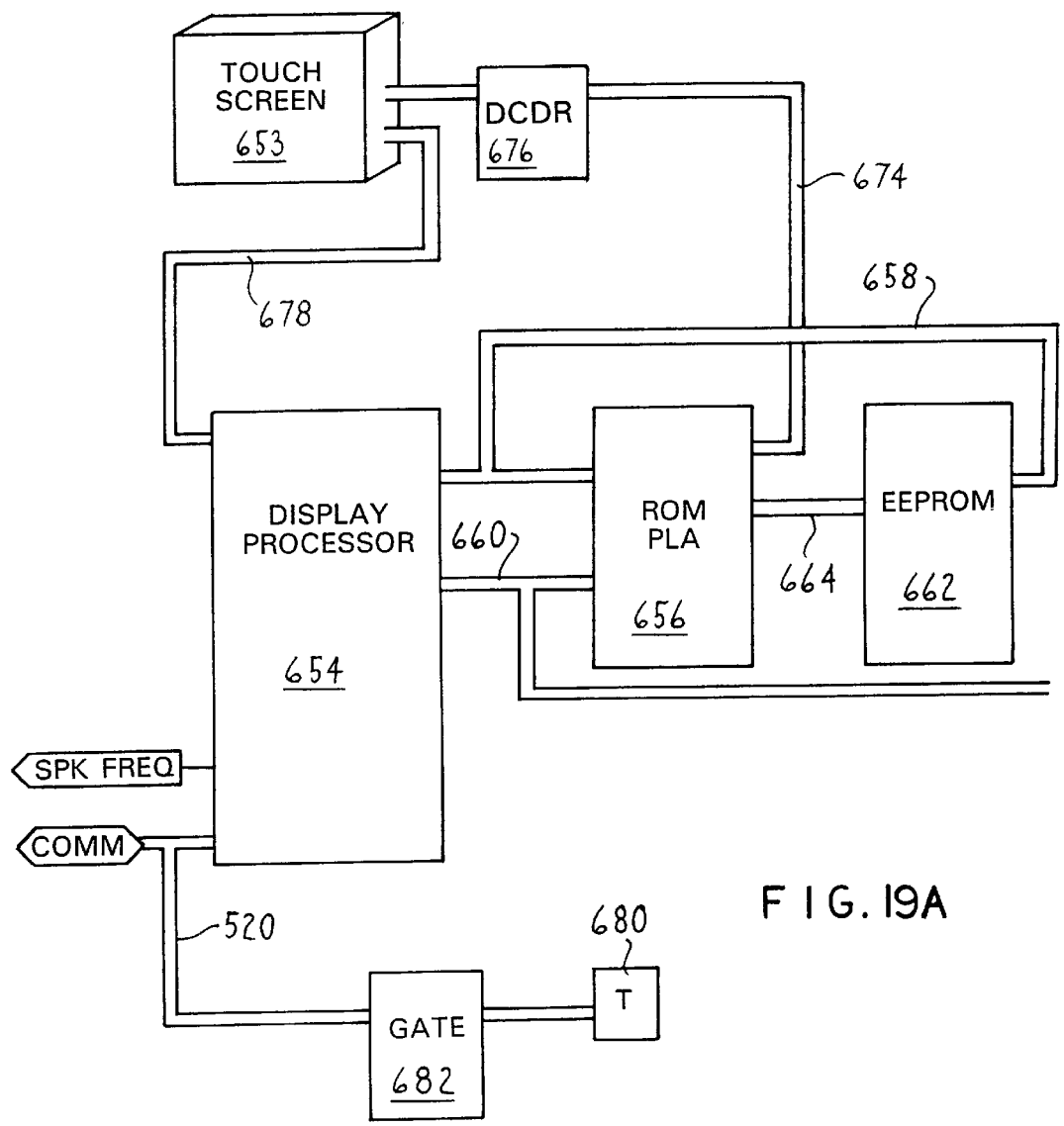
FIGS. 19A and 19B are assembled to form a block diagram display-input/output controller of the control circuit.
Figure 19B:
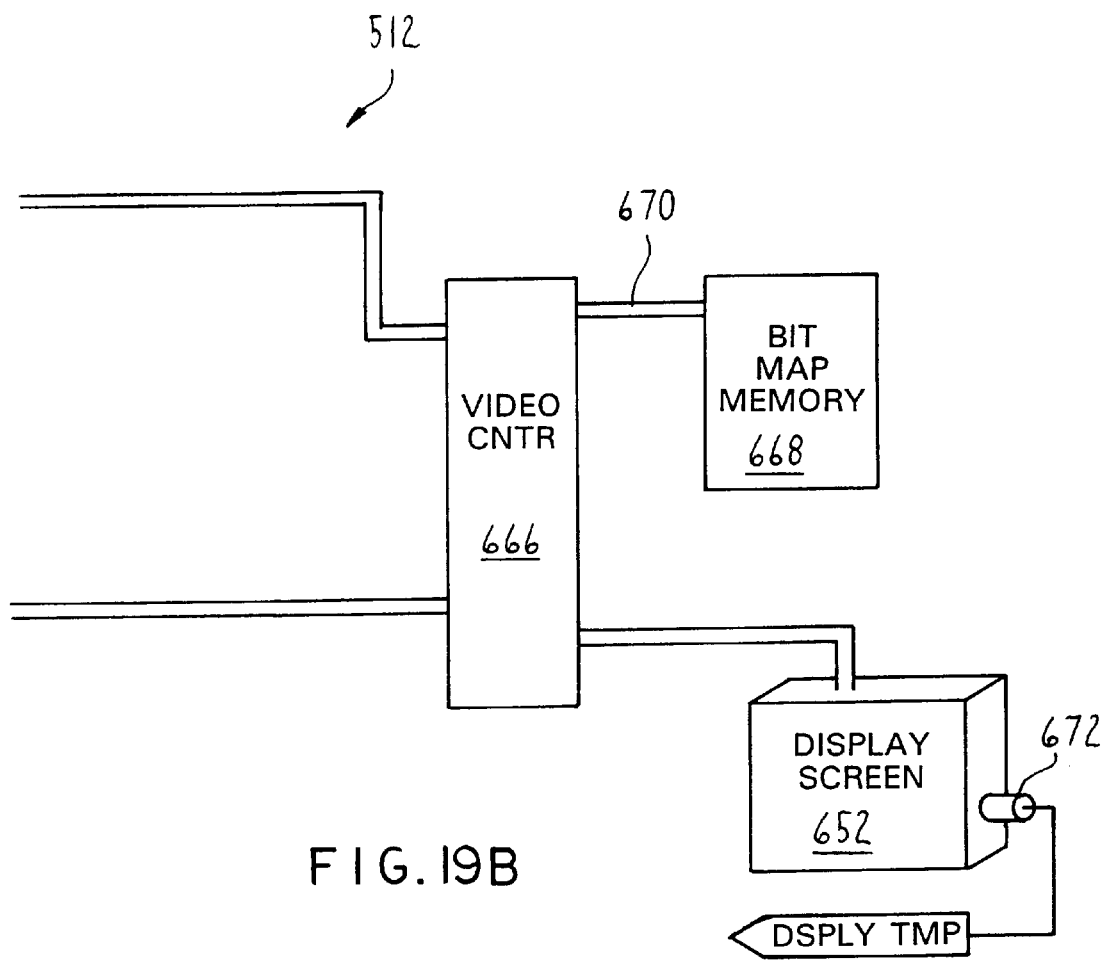

The display input/output controller 512 is now described by reference to FIGS. 19A and 19B. Initially, it should be recognized that the touch screen display 37 includes both display screen 652 and a transparent touch screen 653 that is fitted over the display screen. The display screen 652 is the portion of display 37 that produces the images seen by the surgeon. In one embodiment of this invention, display screen 652 is a liquid crystal display. A processor, integral with the display controls the energization of the electrodes in the display so as to cause the desired image to appear, (processor and electrodes not illustrated). The touch screen 653 is the element of the display that includes the switch surfaces the surgeon selectively touches in enter instructions and acknowledgements into the control console 36. The touch screen 653 contains a number of transparent pressure or heat sensitive switches, such as variable capacitance switches, that are visually defined by the images presented on the display screen 652.

Display input/output controller 512 includes a display processor 654. Display processor 654 performs overall control of the images presented on touch-screen display 37, the audio tones generated through speaker 513 and the generation of commands to the main controller 492 based on the commands entered into the console over the touch-screen display. One suitable processor that can be employed as the touch screen display is the 80C31 processor manufactured by Phillips Semiconductor. Display processor 654 receives basic commands regarding the images to be displayed and audio tones to be generated from microprocessor 518 over communications bus 520. In response to user-entered commands entered from the touch screen 653, the display processor 654 generates commands to microprocessor 518 and forwards them to the microprocessor 518 cover bus 520.

Display processor 654 also generates the SPEAKER_FREQUENCY signal that is applied to converter 558 as a the speaker reference signal. The SPEAKER_FREQUENCY signal is variable frequency pulse signal. The frequency of the SPEAKER_FREQUENCY serves as the basis for the frequency of the analog audio SPEAKER_OUT signal that is selectively asserted by converter 558. The display processor 654 generates the appropriate SPEAKER_FREQUENCY signal based on specific command signals received from microprocessor 518.

Display input/output controller 512 includes a ROM-PLA 656. One suitable ROM-PLA 656 is the PSD313 marketed by Wafer Scale Integration. ROM-PLA 656 contains non volatile data used by the display processor 654 to control the generation of display images, the generation of audio tones and the assertion of commands to the main controller 492. ROM-PLA 656 also contains a fixed logic array that produces some of the commands that need to be asserted as part of the process of generating the required images, tones and processor commands. Address and data signals are exchanged between display processor 654 and ROM-PLA 656 over a 16-bit address-and-data bus 658. The writing of data to ROM-PLA 656 and the reading of signals from the ROM-PLA is controlled by display processor 654 by the exchange of signals over a separate over a read-write control bus 660.

An EEPROM 662 is also part of the display input/output controller 512. The EEPROM stores instructional data that is required by both microprocessor 518 and display processor 654 and that can change during the use of the control console. Such data includes a list of custom configurations a number of doctors find useful for the procedures they perform, the last settings of the control console 36, the last contrast voltage supply to display 37 and the last brightness setting of the display. EEPROM 662 is connected to display processor 654 over address-and-data bus 658. The ROM-PLA 656 controls the addressing of data from EEPROM 662 through the generation of signals asserted over a dedicated EEPROM bus 664. Microprocessor 518 receives data from and writes data to EEPROM 662 by exchanging basic commands and data with display processor 654; based on this exchange of data, display processor 654 performs the required data read or write from or to the EEPROM 662.

Display input/output controller 512 has a video controller 666 that actually generates the commands that cause the desired video images to be generated. One suitable video controller 666 is the E1330 controller manufactured by Epson America. Video controller 666 generates its specific image formation commands based on instructions received from the display processor 654 over a branch of address-and-data bus 658. The reading of data by video controller 666 is controlled by display processor 654 by the assertion of commands over read-write bus 660. The image formation commands generated by video controller 666 are supplied directly to the display screen 652. The processor internal to the display screen 652, based on the received commands, causes the appropriate electrodes internal to the display screen to energize so as result in the formation of the desired image.

A bit map memory 668 is connected directly to the video image controller 666. Bit map memory 668 contains sufficient memory to store multiple pages of data, each page representing a complete image that may need to be presented on the display screen 652. Bit map memory 668 is connected directly to the video image controller 666 which over a dedicated memory bus 670. The video image controller 666 uses the bit memory 668 as a temporary storage unit for holding image formation commands representative of images that are needed for presentation on the display screen 652. If a particular stored image is required, the instructions for that image ar retrieved from the bit map memory 668 by the video image controller 666 and forwarded by the controller 666 to the display screen 652.

In the described version of the system 30 of this invention, there is a temperature sensor 672 mounted to the display screen 652. Temperature sensor 672 is used to monitor the temperature of the display screen and assert the DISPLAY_TEMP signal which is representative of the this temperature. The DISPLAY_TEMP signal is applied to the microprocessor 518. Microprocessor 518 monitors the DISPLAY_TEMP in order to make real time adjustments of the contrast of tine image presented of the display screen 652 in order to compensate for temperature induced changes in contrast.

The states of the switches internal to the touch screen 653 are repeatedly evaluated by display processor 654 and ROM-PLA 656. The switches internal to the touch screen 653 are arranged in a row-by-column array. The ROM-PLA 656 is connected to the touch screen 653 for selectively energizing a column of switches to be scanned. The ROM-PLA 656 asserts a command indicating which column is to be scanned over a dedicated column bus 674. The command asserted by the ROM-PLA 656 is applied to a decoder 676. The decoder 676, in turn, energizes the selected column of switches so that the state of the individual switches therein can be evaluated.

Once a column of switches is energized for scanning, display processor 654, selectively scans each switch therein. The individual switch scanning is performed on a row-by-row basis by the display processor 676. This individual switch scanning is performed by the selective tieing of each switch row to the display processor 654 over a multi-line dedicated row bus 678. The state of the signal present on each line of the row bus 678 serves as an indication of whether or not a switch in the selected row-and-column position is open or closed. If the switch is closed, display processor 654 sends the appropriate message to microprocessor 518 over bus 520.

The display input/output controller 512 also includes a terminal 680 to facilitate the connection of the control console 36 to a manufacturing/maintenance computer, (not illustrated). The manufacturing/maintenance computer provides commands to and exchanges data with the main controller microprocessor 518 and the display processor 654 over a branch of bus 520. A gate 682 connected between bus 520 and terminal 680 controls the exchange of signals from with the manufacturing/maintenance computer. An enable signal that is transmitted by the display processor 654 over a conductor associated with by 520 to gate 682 controls the connection of the manufacturing/maintenance computer to the bus 520. The connection established by bus 520, terminal 680 and gate 682 make it possible for the control console to readily receive software updates from the manufacturing/maintenance computer and for the console to provide the computer with information about the operating history of the console.

Figure 20:
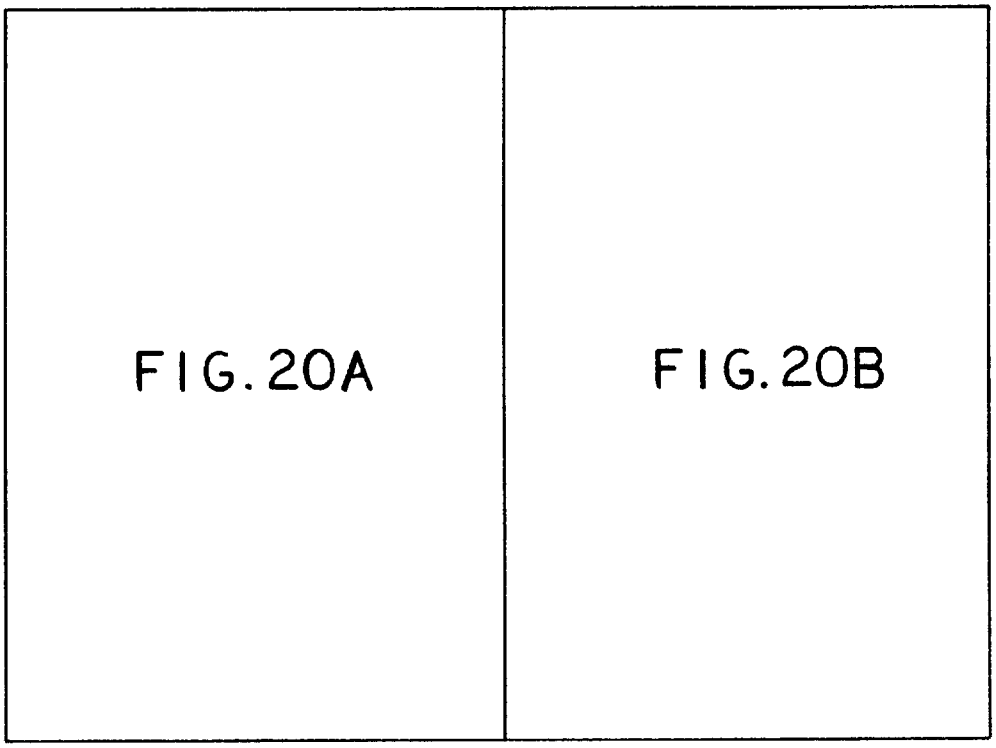
FIG. 20 is a block diagram illustrating how
Figure 20A:
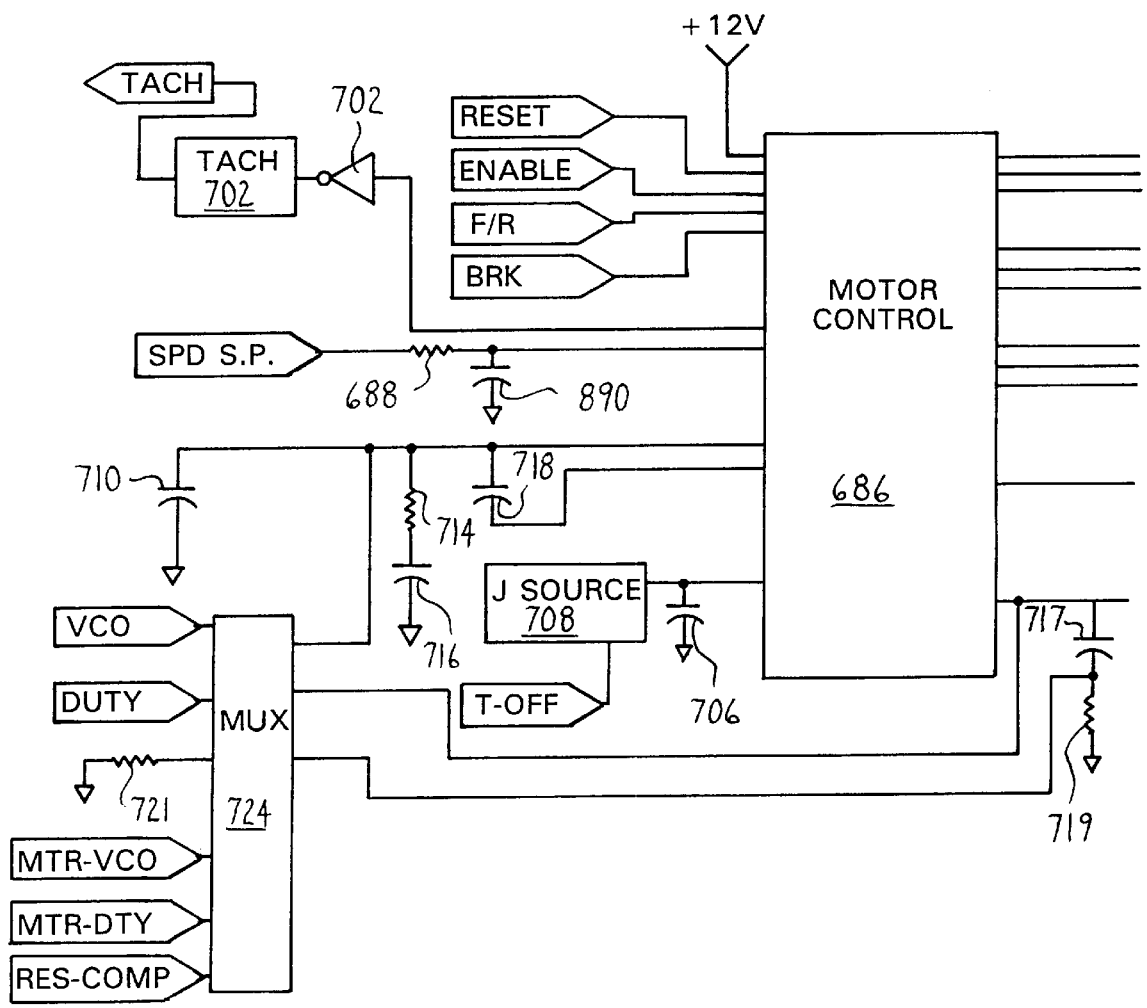
FIGS. 20A and 20B are assembled to form a block diagram of the motor controller and current sensing circuit of the control circuit.
Figure 20B:
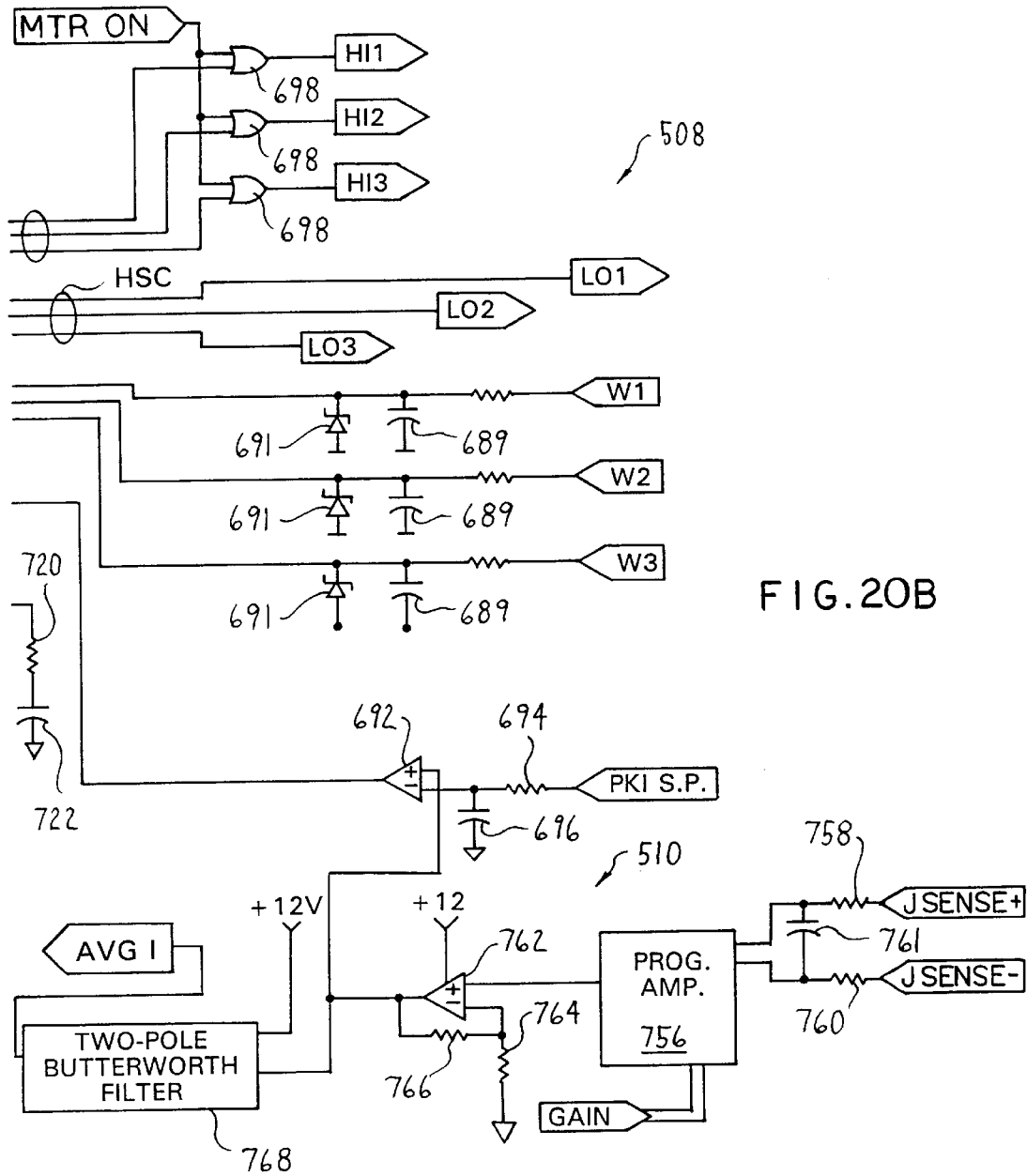

The motor controller 508, now discussed by reference to FIGS. 20A and 20B, determines which signal connections should be made to the windings internal to the motor 52 of the active handpiece 32 or 33 in order to cause the desired rotation of the motor. Motor controller 508 includes a motor control chip 686. Motor control chip 686 asserts the requisite command signals to the motor driver and current sense circuit 510 that cause each winding to either be connected to receive the MOTOR_POWER signal or tied to tied to ground. One suitable motor control chip 686 that can be incorporated into control console 36 is the ML4426 chip manufactured by Micro Linear.

One input signal into motor control chip 686 is the SPEED_SET_POINT signal from converter 536. Motor control chip 686 uses the SPEED_SET_POINT signal as a reference signal for determining the speed at which the handpiece motor 52 should rotate. In the depicted version of the invention, the SPEED_SET_POINT signal is applied to motor control chip 686 through a resistor 688. A capacitor 690 is tied between the SPEED_SET_POINT input terminal and ground in order to damp any voltage spikes that may be in the SPEED_SET_POINT signal.

The FORWARD/REVERSE, BRAKE, RESET and ENABLE signals asserted by microprocessor 518 are applied to the motor control chip 686. Motor control chip 686 uses the state of the FORWARD/REVERSE signal to determine the direction in which the handpiece motor 52 should be rotated. The BRAKE signal is applied to the motor control chip 686 in order to cause the chip 686 to assert the signals to the windings necessary to cause a magnetic field-induced deceleration of the rotor 56 of the handpiece motor 52. The RESET and ENABLE signals are applied to the motor control chip 686 in order to start the rotation of the motor 52. Based on the state of the RESET and ENABLE signals, the motor control chip 686 asserts the signals that cause the initial MOTOR_POWER and ground connections to be made to the motor windings that are necessary to accelerate the rotor 60 from the fully stopped state.

Motor control chip 686 also receives from the field coil assembly 58 internal to the handpiece motor 50 three signals, W1, W2 and W3. The W1, W2 and W3 signals are the back EMF pulse signals generated by the windings as a consequence of the rotation of the rotor 60. Once the rotor 60 starts to rotate, these back EMF signals are used by the motor control chip to determine when each of the windings should be connected to receive the MOTOR_POWER signal or tied to ground. In the depicted version of the control console, a capacitor 689 is tied between the conductor over which the individual W1, W2 or W3 signal is applied to the motor control chip 686 and ground for filtering the back EMF pulses. A reverse biased zener diode 691 is also connected between the conductor and ground. Diode 691 provides current protection for the motor control chip 686 in the event the associated W1, W2 or W3 back EMF signal exceeds an acceptable potential.

The motor control chip 686 is also configured to receive as an input signal a signal based on the PEAK_I_SET_POINT signal. Motor controller 508 has a comparator 692 with an inverting input to which the PEAK_I_SET_POINT signal from converter 556 is applied. The PEAK_I_SET_POINT is applied to comparator 692 through a resistor 694. A capacitor 696 is tied between the inverting input of comparator 692 and ground in order to filter the PEAK_I_SET_POINT signal. A signal representative of the current drawn by the windings in the handpiece motor 52 is applied to the noninverting input of comparator 692 from the motor driver and current sense circuit 510. The output signal from comparator 692 is applied to the motor control chip 686. When comparator 692 determines that the measured current exceeds the maximum established current as indicated by the PEAK_I_SET_POINT signal, the output signal from the comparator changes state. In response to the state change of the output signal from comparator 692, motor control chip 686 stops asserting LOW_SIDE_CONTROL signals. As discussed below, these LOW_SIDE_CONTROL signals must be asserted in order to close the loop through which energization signals are applied to the motor windings.

The primary output signals from the motor control chip 686 are HIGH_SIDE_CONTROL (HSC) signals and LOW_SIDE_CONTROL (LSC) signals. The HIGH_SIDE_CONTROL signals are asserted by the motor control chip 686 so as to cause the motor driver and current sense circuit 510 to selectively apply the MOTOR_POWER signal to the windings. The LOW_SIDE_CONTROL signals are asserted so as to cause the motor driver and current sense circuit to selectively tie the windings to ground. Motor control chip 686 asserts three HIGH_SIDE_ and LOW_SIDE_CONTROL signals, one pair of signals for each winding forming the motor field coil assembly 58.

The three individual HIGH_SIDE_CONTROL signals, which are asserted low, are each applied to the motor driver and current sense circuit 510 through separate two-input OR gates 698. The MOTOR_ON signal from microprocessor 518 is applied to OR gates 698 as the second inputs thereto. The MOTOR_ON signal is also asserted low. Thus, if the MOTOR_ON signal is not asserted, a high signal will be present at least one input into each of the OR gates 698. The high signal at the input of OR gates 698 will cause the gates to assert high signals which are not recognized by the motor driver and current sense circuit 510 as control signals for applying the MOTOR_POWER signal to the windings. The three LOW_SIDE_CONTROL signals are applied directly to the motor driver and current sense circuit 510.

Motor control chip 686 also asserts a variable frequency DC-pulse output signal, not identified, that is representative of the speed of the motor 52 sensed by the chip 686 as a consequence of the monitoring of the back EMF signals by the chip. This output signal is applied through an inverter 702 to a divide-by-N counter 704. The output pulses from counter 704 are applied to the microprocessor 518 as the TACHOMETER signal.

A capacitor 706 is tied between one terminal, (not identified), of the motor control chip 686 and ground. Capacitor 706 serves as an external timing capacitor for establishing a "time-out period" during which the LOW_SIDE_CONTROL signals are negated when the current drawn by the handpiece motor 52 exceeds the peak current set point established by main controller 492. Normally, a current source internal to motor control chip 686 provides a charge to capacitor 706. A transistor internal to motor controller chip 686 is tied between capacitor 706 and ground. This transistor is normally turned on so as to prevent capacitor 706 from charging. A comparator internal to the motor controller chip 686 monitors the potential across capacitor 706.

In the event the current drawn by the handpiece motor 52 exceeds the peak current set point established by the main controller 492, motor controller chip stops asserting the LOW_SIDE_CONTROL signals. Simultaneously, the transistor internal to the motor control chip 686 that is tied across capacitor 706 is turned off. The turning off of the transistor internal to motor control chip 686 allows capacitor 706 to charge. The charging of capacitor 706 causes the voltage across the capacitor to rise above an internal reference voltage within motor control chip 686. Once the voltage across capacitor 706 rises above the internal reference voltage, the output signal from the internal comparator undergoes a state transition so as to cause the motor control chip 686 to start reasserting LOW_SIDE_CONTROL signals. The time-out period for which the motor control chip 686 negates the assertion of LOW_SIDE_CONTROL signals is a function of the time it takes capacitor 706 to charge to the point where the voltage across the capacitor will rise above the internal reference voltage.

In order to provide the control console 36 with the ability to vary the time-out period in which the assertion of LOW_SIDE_CONTROL signals are negated, a programmable current source 708 is attached to the junction of motor control chip 686 and capacitor 706. The current applied to capacitor 706 by current source 708 is established by the TIME_OUT signal from converter 556.

Motor controller 508 includes a pulse width modulator control circuit (internal PWM), not illustrated, which is part of the speed control feedback loop for controlling the duty cycle of the chop periods as discussed hereinafter. The duty cycle of the chop period is controlled in order to regulate the acceleration and deceleration of the rotor 56 so that the motor runs at the desired speed as indicated by the SPEED_SET_POINT signal. An external impedance network in combination with an amplifier integral with the internal PWM, is provided to ensure that there is an accurate gain roll off for the handpiece motor 52 attached to the control console 36 to ensure speed loop stability through the range of operation of the motor. As seen in FIGS. 20A and 20B, this external network consists of a capacitor 717 and a resistor 719 that are series connected between a PWM adjust terminal on motor control chip 686 and ground. The external impedance network further includes a resistor 720 and a capacitor 722 that are connected across capacitor 717 and resistor 719.

This external impedance network of the motor controller 508 of this invention further includes additional components that are capable of changing the impedance of the network. In the depicted version of the invention, the external impedance network includes a resistor 721. Resistor 721 is connected at one end to ground and is selectively tied to the junction of capacitor 717 and resistor 719 through a multiplexer 724. Multiplexer 724 connects/disconnects resistor 721 to the external impedance network based on the state of the RESISTOR_COMPENSATION signal asserted by the main microprocessor 518.

Motor controller 508 also controls the application of direct drive mode energization signals to a handpiece. The control console 36 is operated in the direct drive mode by having the main controller 492 take control of a voltage controlled oscillator (internal VCO) in motor controller chip 686, not illustrated, and the internal PWM. The internal VCO controls the commutation frequency of the application of the MOTOR_POWER signals to the motor windings. This commutation frequency is the basic frequency with which the MOTOR_POWER signal is applied to the separate windings, the time period each HIGH_SIDE_CONTROL signal is asserted. The chop cycle regulated by the internal PWM is the on-off duty cycle the winding complementary to the winding to which the MOTOR_POWER signal is applied is tied to ground. Typically multiple "on" chop periods occur during an individual commutation "on" period. Thus, during each period a particular HIGH_SIDE_CONTROL signal is asserted to one winding, the LOW_SIDE_CONTROL signal that is asserted to the complementary winding is cycled on and off a number of times.

In the depicted motor controller 508, the internal VCO of motor control chip 686 is normally adjusted by a capacitor 710 which is tied between a VCO adjust terminal on chip 686 and ground. A series connected resistor 714 and capacitor 716 that are connected across capacitors 710 and 712 also adjust the internal VCO tuning and compensation. Further adjustment of the internal VCO is accomplished with an additional external capacitor 718 that is connected between the VCO adjust terminal and a ramp terminal also on the chip 686.

The control console 36 is operated in the direct drive energization mode by the selective assertion of the VCO and DUTY signals to, respectively, the internal VCO and internal PWM within the motor control chip 686. The VCO and DUTY signals are applied from converter 556 to inputs of separate channels of multiplexer 724. Multiplexer 724 functions a switch to control the application of VCO and DUTY signals to the motor control chip 686. The VCO signal is selectively applied from multiplexer 724 to the VCO adjust terminal of the motor control chip 686. The DUTY signal is selectively applied from multiplexer 724 to the PWM adjust terminal of the motor control chip 686. The application of the VCO and DUTY signals to the motor control chip is controlled by the assertion of the MOTOR_VCO and MOTOR_DUTY signals by microprocessor 518. The MOTOR_VCO and MOTOR_DUTY signals are applied to the address inputs of multiplexer 724 in order to establish the circuit connections made by the multiplexer. Depending on the state of the MOTOR_VCO and MOTOR_DUTY signals, none, one of or both of the VCO and DUTY signals may be applied to the motor control chip 686. When the VCO and DUTY signals are applied to the motor control chip 686, the chip asserts the necessary HIGH_ and LOW_SIDE_CONTROL signals to effect the desired application of direct drive energization signals.

Figure 21:
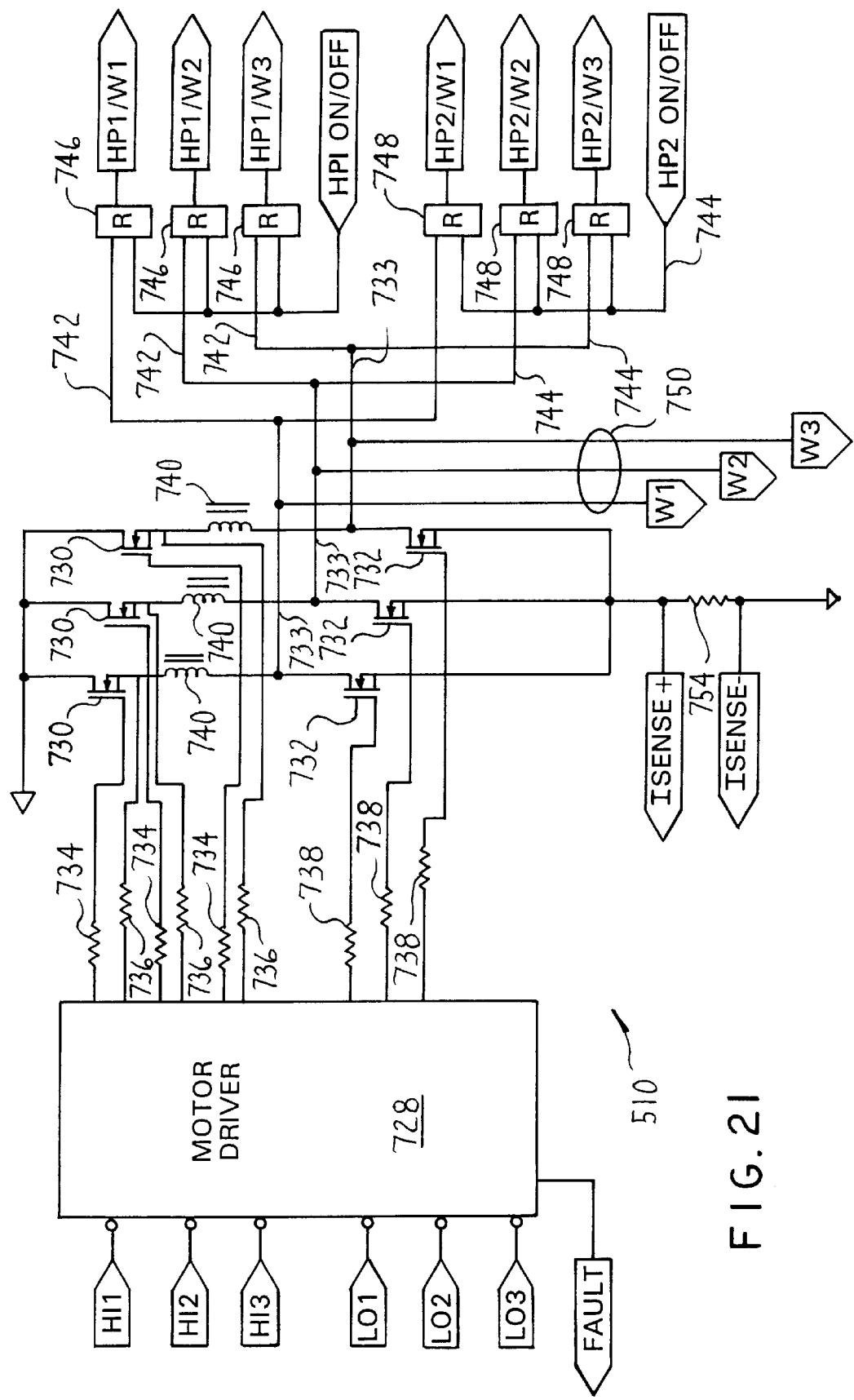
FIG. 21 is a schematic diagram of the motor driver of the control circuit.

The motor driver and current sense circuit 510 is now described by initial reference to FIG. 21. Motor driver and current sense circuit 510 includes a motor driver chip 728 to which both the HIGH_ and LOW_SIDE_CONTROL signals from the motor control chip 686 are applied. Based on the state of the HIGH_ and LOW_SIDE_CONTROL signals, the motor driver chip 728 asserts the FET driver signals employed to cause the application of the MOTOR_POWER signals to the windings or to tie the windings to ground. One suitable chip that can be used as the motor driver chip 728 is the IR2130 manufactured by International Rectifier.

In the illustrated version of the invention, motor driver chip 728 is also configured to assert a FAULT signal to microprocessor 518(connection to microprocessor 518 not shown). Motor driver chip 728 asserts the FAULT signal whenever it receives HIGH_ and LOW_SIDE_CONTROL signals that would cause the motor driver chip 728 to assert FET driver signals that would result in improper MOTOR_POWER or ground connects to the windings. The FAULT signal may be asserted, for example, if the motor driver chip 728 receives an indication it is connect one winding to both the MOTOR_POWER signal and ground. Microprocessor 518 recognizes receipt of the FAULT signal as an indication of a fault in the application of energization signals to the motor and takes appropriate action.

Motor driver and current sense circuit 510 also includes three high side FETs 730 each of which is series connected to a complementary low side FET 732. Conductors 733, which supply the energization signals to the individual windings, are connected to the source terminals of FETs 732. Each high side FET 730 serves as the switch for connecting the conductor on which the MOTOR_POWER signal is present to one of the windings internal to a handpiece 32 or 33. Each complementary low side FET 732 serves as the switch to connect the handpiece winding to ground.

The on\off stales of FETs 730 and 732 are controlled by the FET driver signals applied to their gates from motor driver chip 728. The FET driver signals are applied to the gates of FETs 730 through individual load resistors 734. The signals present at the drains of FETs 730 are applied back to the motor driver chip 728 to provide a reference for determining the appropriate amplitude of the signals that should be provided to the gates of the FETs 730. The signals from the drains of the FETs 730 are applied back to the motor driver chip 730 through separate resistors 736. The FET driver signals applied to the gates of FETs 732 are applied thereto through load resistors 738.

An inductor 740 is connected between the drain of each FET 730 and the associated FET 732-conductor 733 junction. Each inductor 740 has an inductance that is relatively small compared to the inductance of the associated winding that is part of the motor field coil assembly 58. For example, in some versions of the invention each inductor 740 has an inductance of approximately 0.1 to 10 microhenrys, in more preferred versions and inductance of 0.1 to 1 microhenrys and in still more preferred versions approximately 0.5 microhenrys.

Inductor 740 functions as a suppressor for a high current spike that would other wise develop during the commutation cycle when a FET 730 is turned off and the complementary FET 732 is turned on. A current spike occurs at this moment because, prior to the transition of the states of the FETs, FET 730 acts as a capacitor across which there is a 0 VDC potential. At the time the state of the FET 732 changes, the FET 732 becomes a low resistance conductor. Consequently, the voltage across FET 730 rapidly charges. Owing to the low on-state resistance of FET 732, this voltage causes a relatively high current spike to flow through a sense resistor 754 to ground. Inductor 740 suppresses the magnitude of the current spike.

Conductors 733 separate into two sets of branch conductors, conductors 742 and 744. Conductors 742 extend to the first socket on the face of the control console 36 to which handpiece 32 is connected and conductors 744 extend to the second socket to which handpiece 33 is connected. Conductors 742 are connected to the associated socket contacts, (not illustrated), through separate relays 746. The open/closed state of relays 746 is controlled by the HANDPIECE1_ON/OFF signal. Relays 746 are configured so as to be in the open state unless the HANDPIECE1_ON/OFF is asserted. Conductors 744 are connected to their associated socket contacts through individual relays 748. Relays 748 are closed only when the HANDPIECE2_ON/OFF signal is asserted.

Also attached to conductors 733 are three additional branch conductors 750. Conductors 750 serve as the conductors over which the W1, W2 and W3 back EMF signals from the individual windings are applied to the motor driver chip 728.

As seen by reference to FIG. 21, the current sense portion of the motor driver and current sense circuit 510 includes a resistor 754 that is tied between the drains of FETs 732 and ground. Resistor 754 serves as the current measuring resistor through which the current drawn by the windings flows for measurement. The voltage across resistor 754 is measured as measured as ISENSE+ and ISENSE− signals.

The ISENSE+ and ISENSE− signals are applied to the rest of the motor driver and current sense circuit which is now described by returning to FIGS. 20A and 20B. The ISENSE+ and ISENSE− signals are applied to a programmable amplifier 756 through resistors 758 and 760, respectively. A capacitor 761 is tied between resistors 758 and 760. Amplifier 756 can amplify the ISENSE signal by a gain of 1, 2 5 or 10. The gain with which amplifier 756 boosts the ISENSE signal is modified is a function of the GAIN signal applied to the amplifier 756 from microprocessor 518.

The output signal from programmable amplifier 756 is applied to the noninverting input of a fixed gain amplifier 762. A resistor 764 is tied between the inverting input of amplifier 762 and ground and a resistor 766 is tied between the output of amplifier 762 and the inverting input. In one version of the invention, resistors 764 and 766 are selected so that amplifier 762 has again of 10.

The output signal from amplifier 762 is branched to two locations. A first location to which the output signal is branched is the noninverting input of comparator 692 of motor controller 508. Thus, the instantaneous amplified ISENSE signal serves as the signal against which the PEAK_I_SET POINT signal is compared in order to determine if the active handpiece 32 or 33 is drawing more than the allowed amount of current. The second location to which the output signal from amplifier 762 is applied is a two-pole Butterworth filter 768. Butterworth filter 768 averages the amplified ISENSE signal in order to produce the AVERAGE_I signal. The AVERAGE_I signal is applied to the microprocessor 518 as the measurement of the current drawn by the active handpiece 32 or 33.

Any suitable CCFT controller and audio amplifier may be incorporated into the backlight and speaker controller 514, (controller and amplifier not illustrated). One suitable CCFT controller that can be employed is the LT1182CS manufactured by Linear Tech. The BRIGHTNESS and CCFT_ON signal from the main controller 492 are typically applied directly to the CCFT controller. The CONTRAST signal from the main controller is applied to a balancing circuit that controls the application of contrast signals to the display screen 652. In one version of the system 30, the backlight and speaker controller 514 audio amplifier amplifies the SPKR_OUT signal by a gain of approximately 5 before applying the signal to the speaker 513.

The pump controller 515 includes any suitable motor control circuit. One such circuit is the UC 3823 controller manufactured by Unitrol. Pump controller 515 is also configured so to serve as a connector that supplies the PUMP_SENSE signal to indicate whether or not a pump 40 is attached to the system 30.

Figure 22:
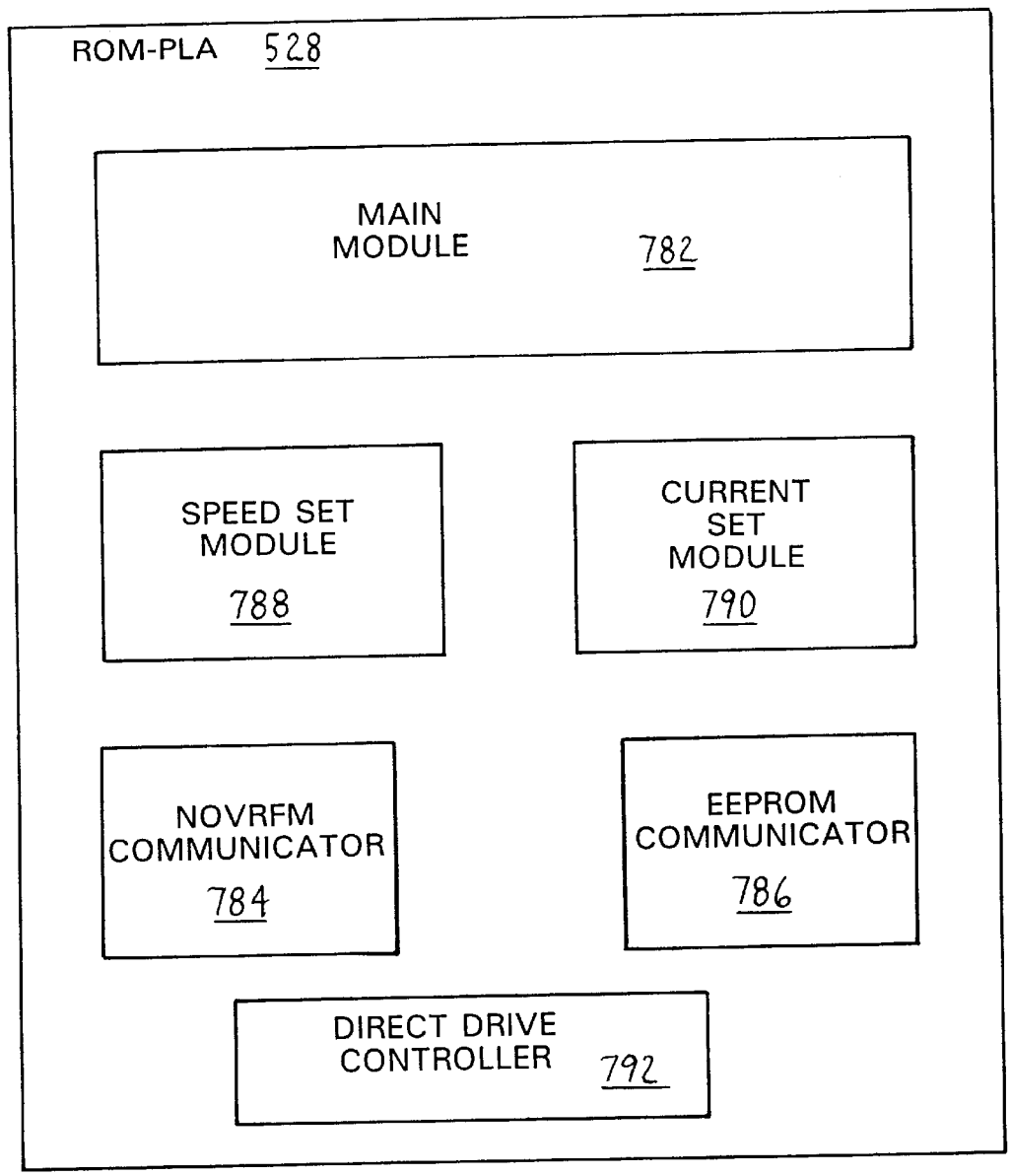
FIG. 22 is a block diagram of the memory accessed by the microprocessor within the main controller illustrating the modules that are selectively executed by the microprocessor during the operation of the system.

FIG. 22 depicts in block diagram the primary modules stored within ROM-PLA 528 that contain the instructions that are selectively executed by microprocessor 518 during the operation of the system 30. Not depicted is the basic operating system that performs the input/output functions, handles interrupts and exceptions and performs the other operating chores required to make the system operate. A main module 782 is the primary module. Main module 782 is the module that is first actuated when the system 30 is initialized and the module that selectively controls the actuation of the other modules. A NOVRAM communicator 784 contains the software instructions that control the retrieval of the data contained within handpiece NOVRAM 72 and the complementary NOVRAM within the footswitch assembly 46. An EEPROM communicator 786 contains the instruction used to control the reading of data from and the writing of data to the EEPROM 74 within the handpiece 32 or 33. Communicator modules 784 and 786 are designed to retrieve and write data serially in accordance with the particular specifications of, respectively, the NOVRAM 72 and the EEPROM 74. Accordingly the specific design of the communicators 784 and 786 will not hereinafter be discussed in any additional detail.

The ROM-PLA 528 includes three additional modules that are executed by microprocessor 518 so that control console 36 applies the correct energization signals to handpiece 32 or 33. A speed set module 788 contains the instructions for generating the SPEED_SET_POINT signal. A current set module 790 contains the instructions for generating the remaining primary control signals generated by microprocessor 518, such as the PEAK_I_SET_POINT signal. A third module, a direct drive module 792, contains the instructions for generating the signals that are asserted by microprocessor 518 when the control console 36 is selected to operate in the direct drive mode.

Figure 23:
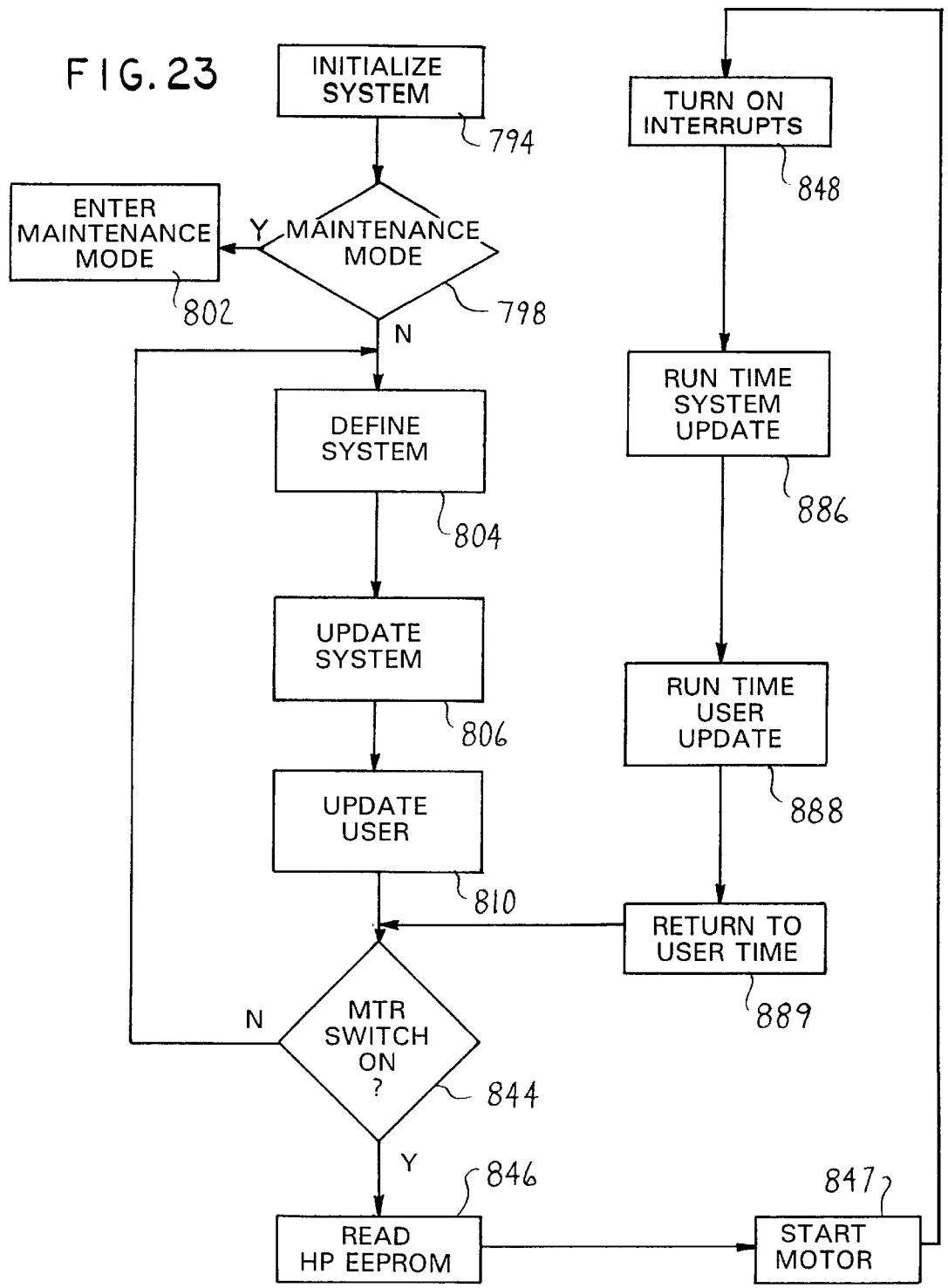
FIG. 23 is a flow chart of the primary processing steps executed by the microprocessor within the main controller based on the instructions contained within the main module.
Figure 24:
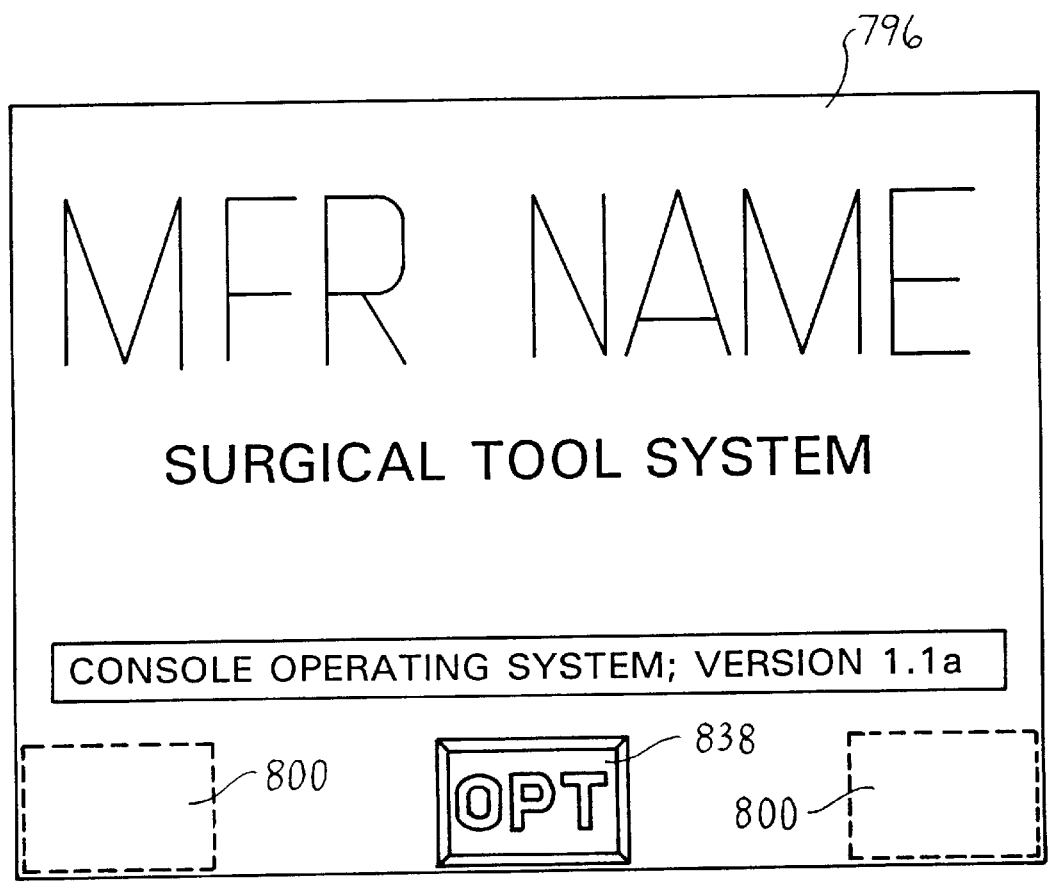
FIG. 24 is an illustration of the sign-on screen, image, presented by the control console when the system is initialized.

FIG. 23 provides a basic explanation of the process steps executed by microprocessor 518 based on the instructions contained within main module 782. When control console 36 is initially actuated, a system initialization step 794 is initially performed. During system initialization step 794, microprocessor 518 as well as the other components of the system are placed in an initial ready to run state. During initialization step 794, microprocessor 518 directs the display input/output controller 512 to present an a sign-on image 796, illustrated by FIG. 24, on display 37. Sign-on image 796 contains initial information that there is an interest in presenting to the system user.

After initialization step 794 is executed, microprocessor 518 makes an evaluation to determine if the system 30 is to be placed in a maintenance mode as illustrated by step 798. Step 798 is actually a multi-step process. Initially, when the sign-on image 796 is presented, microprocessor reviews the data received from display input/output controller 512 to determine if two phantom buttons 800 presented on touch screen display 37 have been depressed. Buttons 800, which are depicted in dashed lines, are not actually visible images that form part of the sign-on image 796. Instead, only support personnel, not surgical personnel, know of the existence of these buttons. If the buttons 800 are depressed, microprocessor 518 then evaluates whether or not a maintenance key with a maintenance code is attached to one of the sockets on the face of the console 36. A maintenance key is shaped similar to a handpiece motor housing 50 and plugs directly into a cable socket 504 or 506 on control console 36. A NOVRAM is contained within the maintenance key. Microprocessor 518 reads the maintenance key NOVRAM. If the microprocessor 518 determines that the NOVRAM within the maintenance key contains a valid code, the microprocessor exits the main module and enters a maintenance module, represented by step 802, (maintenance module not identified.)

If control console 36 is not to enter the maintenance mode, microprocessor 518 proceeds to define the system as represented by step 804. In step 804 microprocessor 518 reads a number of the signals that it is presented in order to determine how the system should be configured. With regard to the handpieces, microprocessor first reviews the state of the CABLE_x signals to determine cables 43 or 47 are coupled to the complementary sockets 504 and 506 on the face of the control console 36. If a cable 43 or 47 is connected to a socket, microprocessor 518 evaluates whether or not a handpiece 32 or 33 is connected to the end of the cable. Initially, this evaluation begins by microprocessor 518 asserting or negating the HP_1/2 signal as is appropriate to connect the cable, and any handpiece attached thereto, to the microprocessor through the handpiece interface 502. In one version of this invention, the evaluation of whether or not a handpiece is connected to a cable is made by evaluating the state of the HP_CUR signal. If the HP_CUR signal indicates that a current is being drawn, this state is recognized as an indication that a handpiece 32 or 33 is attached to the control console 36.

If a handpiece 32 or 33 is attached to the control console 36, as part of system definition step 804, microprocessor 518 retrieves the data contained in the handpiece NOVRAM 72 and EEPROM 74. This data retrieval is performed with the aid of the instructions contained in the NOVRAM communicator and EEPROM communicator modules 784 and 786, respectively. This data is forwarded to microprocessor 518 in the form of HP_REC signals.

System definition step 804 also includes a retrieval of the ancillary data needed to configure the control console 36. This data includes determining whether or not a pump 40 and a foot switch assembly 46 are connected to the control console 36. If microprocessor 518 determines that a foot switch assembly 46 is present, the microprocessor accesses the NOVRAM communicator module 784 in order to retrieve the calibration data for the attached foot switch assembly 46 from its memory 329. This data is retrieved by microprocessor 518 as the FS_REC signals. Also, the current user-selected settings for the ancillary components of the system are read. These settings include, the brightness and contrast of the display 37, the speed of the pump 40, the volume of the speaker 513 and the intensity selection for the bulb 248 attached to light and water clip 45. During the initial execution of the system definition step 804, these settings are retrieved from display input/output controller EEPROM 662 wherein the settings from the last use of control console 36 are stored.

Once system definition step 804 is complete, microprocessor 518 executes an update system step 806. In update system step 806, microprocessor 518 determines the appropriate control signals based on information received during system definition step 804. With regard to the ancillary components, microprocessor 518 establishes the BRIGHTNESS, CONTRAST, PUMP_SET_POINT, and SPEAKER_OUT, and CCFT_ON signals. Once the appropriate levels for these control signals are determined, the signals that need to be asserted are asserted, while the signals that may be needed later are stored. For example, the BRIGHTNESS and CONTRAST signals are immediately asserted since these signals are used to control the presentation of all images on display 37. The PUMP_SET_POINT and LIGHT_CONTROL signals, in contrast, are stored in the event the components to which these signals are applied are to be actuated.

As part of update system step 806, microprocessor 518 makes the appropriate calculations needed to run the handpieces 32 or 33 attached to the control console 36. These calculations include the generation of a data table representative of the speed-to-torque plot 438 of FIG. 14. This data table is based on the data retrieved from the handpiece NOVRAM 74.

Figure 25:
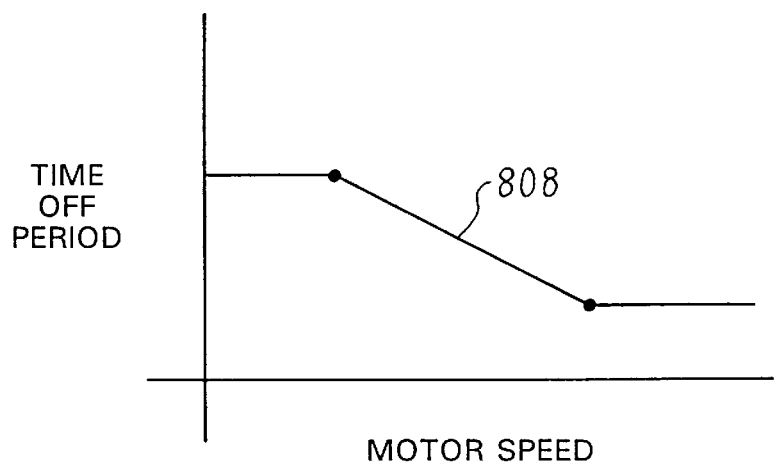
FIG. 25 is graphical illustration of how the excess current limit time out period for a handpiece motor varies as a function of the current operating speed of the handpiece.

Microprocessor 518 also uses the data retrieved from the time out field 449 in handpiece NOVRAM 72 to generate a data table representative of the time out plot 808 of FIG. 25. The time out plot 808 is a graphical representation of the relationship between the measured speed of the motor 52 and the time period after the motor has drawn a current in excess of that specified by the PEAK_I_SET_POINT for which energization signals should not be applied to the motor. Time out field 449 contains data representative of two plot points; a first, low speed point and second, high speed point. As seen by reference to FIG. 25, when the motor is running at a lower speeds, the time period for which its operation should be timed out is greater than when it is running at higher speed. As indicated by plot 808, for speeds less than the first, low speed, the time out period is the time period specified for the first speed. For speeds less than the second, high speed, the time period is that of the second speed.

Figure 26:
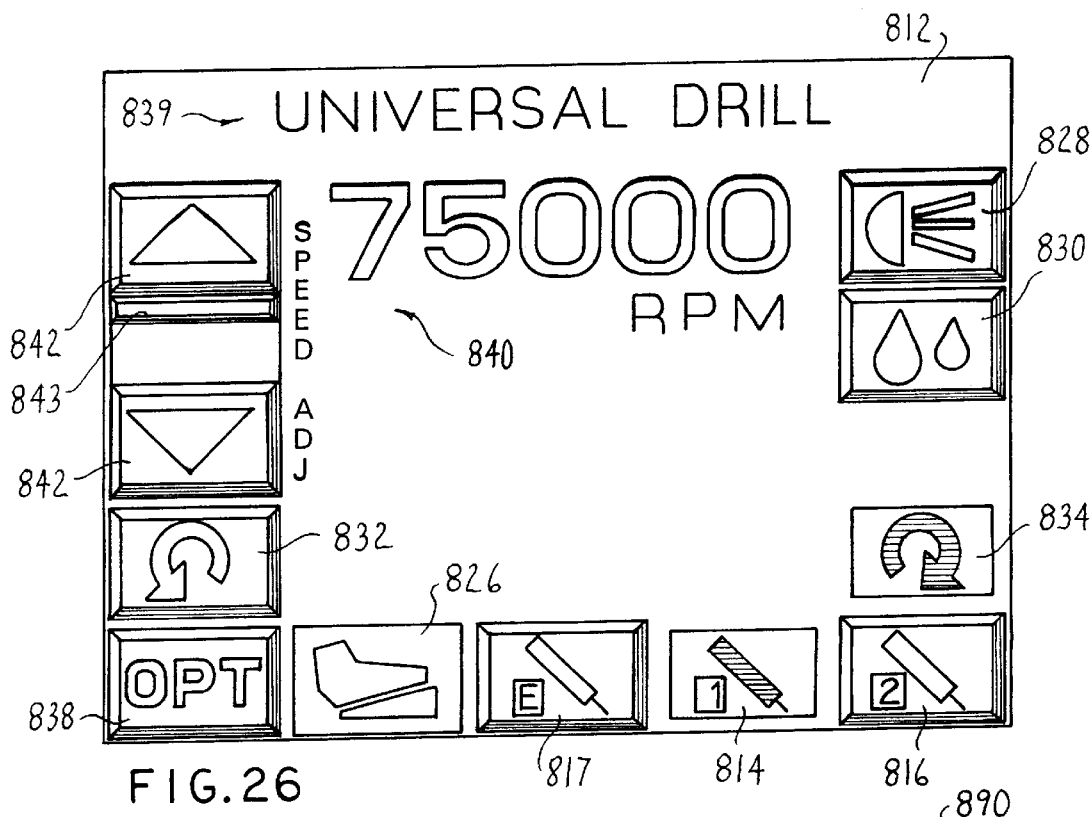
FIG. 26 is an illustration of the primary user time image presented by the control console after the system is initialized and when at least one handpiece is plugged into the control console when the system is initialized.

After update system step 806, microprocessor 518 performs an update user step 810 (FIG. 23). In update user step 810, information regarding the status of the system 30 is presented to the user. The primary means by way system information is provided is by the presentation of a user time image 812 on display 37, which is now described by reference to FIG. 26. The commands to generate the individual elements forming the images are generated by the display input/output controller 512. Microprocessor 518, during update user step 810 and during other times microprocessor displays information, actually generates general image display commands to the display input/output controller 512. Based on these commands, display input/output controller 512 causes the appropriate image to be presented on the display 37.

User time image 812 includes a set of buttons, icons and data lines depending on the particular state of the system. Along the bottom right edge of image 812, smaller images indicate whether or not any handpieces are connected to the complementary sockets of the control console 36. If handpieces 32 or 33 are connected to both sockets, buttons 814 and 816 appear indicating the presence of the handpieces. The user can then select one of the handpieces to be active by depressing the button 814 or 816 for the associated socket. If neither button 814 and 816 are depressed, each button has the three-dimensional profile of button 816 and the handpiece symbol within the button appears white. Once a button is depressed, it has the flat profile of button 814 and the handpiece symbol within the button goes black so as to collectively provide a quick visual indication of which of the two sockets has the active handpiece. Main module 782 further includes instructions that cause microprocessor 518 to recognize the assertion of the FS_CNTR signal as an indication to switch the active handpiece from the designed one to the inactive one. Regardless of the means by which a handpiece is selected, microprocessor 518 negates or asserts the HP_1/2 signal as is necessary to connect the selected handpiece to the control console 36 through handpiece interface 502.

The illustrated user time image 812 also includes an auxiliary button 817. Button 817 is used to indicate the presence of and control the active state of handpieces that could be energized by the system but that do not include the NOVRAM with handpiece data as described with reference to handpieces 32 and 33.

Figure 27:
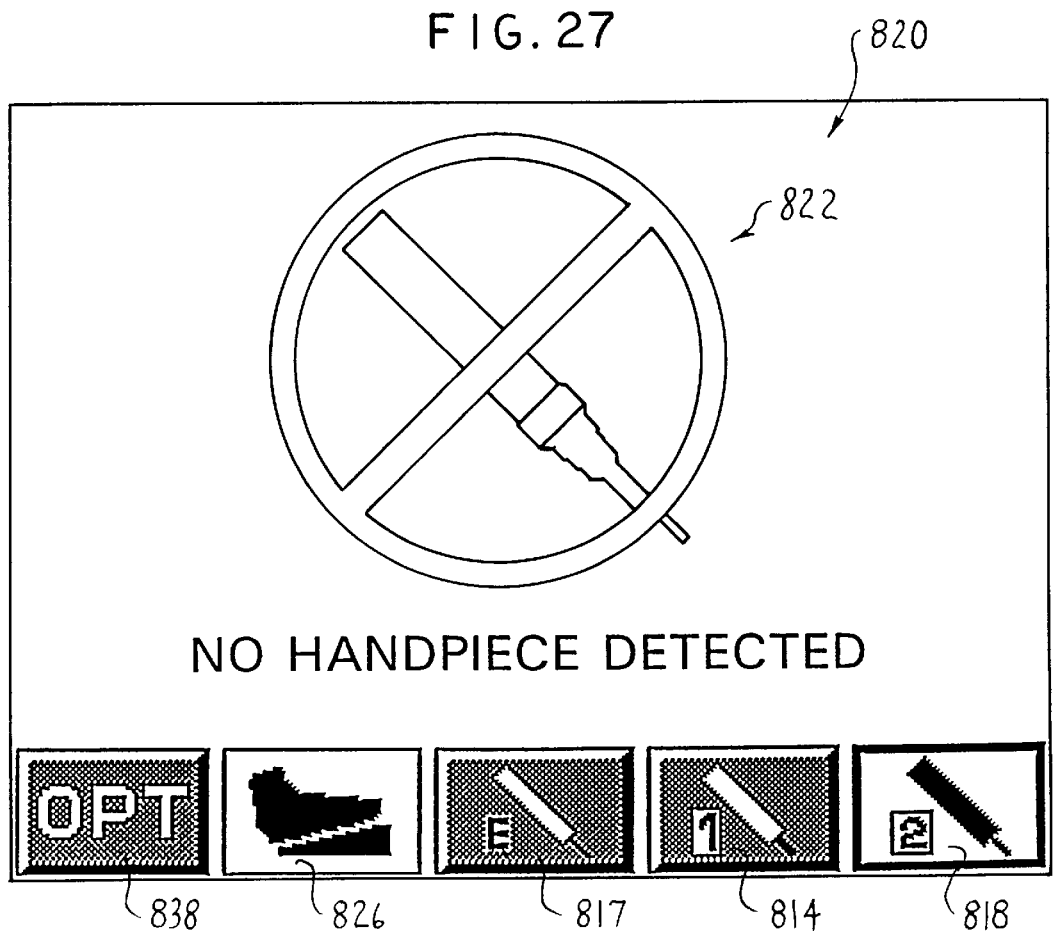
FIG. 27 is an illustration of the cable only/no handpiece connected image presented by the control console when there is a cable without a complementary handpiece attached to the control console and an individual indicates an interest in actuating the cable.

In the event a cable 43 or 47 with no handpiece is attached to control console 36, a cable only icon 818 appears on the screen as represented by cable only image 820 now described by reference to FIG. 27. Alternatively, in some versions of the invention a socket cable-only state is represented as a button without a handpiece symbol therein. If a person depresses the cable only the button or foot switch 44*d*, microprocessor 518 causes a large no handpiece detected icon 822 to be presented on display 37.

Returning to FIG. 26, it can be seen that if a button 814 or 816 associated with a handpiece 32 or 33 connected to control console 36 is depressed, other information is presented as part of user time image 812. If a foot switch assembly 46 is attached to control console 36, a foot switch icon 826 is presented.

If a light and water clip 45 is attached to the selected handpiece 32 or 33, and these ancillary components are compatible with the handpiece, microprocessor 518 will cause image 812 to include buttons 828 and 830 indicating the availability of these features. It should be recognized that microprocessor 518 will only cause button 828, the light option button, to be presented if the LIGHT_SENSE signal from the handpiece interface 502 indicates that for the active handpiece the bulb 248 in light-and-water clip 45 is in the good state. If the LIGHT_SENSE signal indicates the bulb 248 is burned out, microprocessor 518 will instruct display input/output controller 512 to generate an appropriate fault message on screen 37. Depression of buttons 828 and 830 will, respectively, cause bulb 248 and pump 40 to be actuated with the actuation of the handpiece to which they are coupled.

If appropriate for the handpiece, buttons 832 and 834 respectively provide in indication of whether or not the handpiece can be driven in the forward or reverse direction. Depression of one of the buttons 832 and 834 will cause the button to flatten and the symbol contained therein to darken as indicated by button 834. An option button 838 gives the user the opportunity of switching to different screens that present switches that allow the user to control the ancillary components of the system 30. The buttons associated with the option screens allow the user to control the brightness and contrast of the images presented on the display, the volume of the speaker 513, the rate at which pump 40 supplies water and the intensity of the light emitted by the bulb associated with the light-and-water clip 45. Moreover, as described hereinafter, a special options screen allows the surgical personnel to enter a set of pre-defined system settings that are customized for a specific procedure performed by an individual doctor.

Another feature that can be selected by initial actuation of options button 838 is the language in which information about the system 30 is presented. In one version of the invention, at the time use is allowed to select the settings for the display 37 and speaker 513, display input/output controller 512 also presents a set of buttons and icons that allow the user to select the language in which the information presented on display 37 is presented.

For some handpieces, still other option features allow the user to set the rate at which the motor internal to the handpiece accelerates or decelerates. The fastest acceleration rate is based on data contained in NOVRAM field 442. The fastest deceleration is contained in NOVRAM data field 444.

User time image 812 also includes a tool identification lines 839 that provides the name of the active handpiece 32 or 33. This name is based on the data retrieved from handpiece identifier field in NOVRAM 72. Immediately below tool identification line 839 is maximum speed identifier 840. Maximum speed identifier 840 is a data line that indicates the maximum speed at which the handpiece 32 or 33 can be operated. It should be recognized that this speed, as well as all other speed information presented on display 37 are "tip speeds" that is, speeds at the tip end, the driving end, of the handpiece. If there is a transmission within the handpiece, microprocessor 518 will make the appropriate speed conversion based on the data contained within gear ratio field 394 of NOVRAM 72 to present tip speed to the surgical personnel.

Immediately to the left of maximum speed identifier 840 are speed adjustor buttons 842. Speed adjustor buttons 842 allows the medical personnel to reset the maximum speed so it can be adjusted downward from the actual maximum speed of the handpiece. During update system step 806, microprocessor 518 will selectively adjust the maximum speed of the handpiece subject to the limit data retrieved from fields 386, 388 and 390 in handpiece NOVRAM 72. A slide bar 843 is located between speed adjustor buttons 842. Slide bar 843 provides surgical personnel with a visual indication of the extent it is further possible for them to either increase or decrease the maximum speed of the handpiece.

Also as part of user update step 810, microprocessor 518 will generate the appropriate signals to the display input/output controller 512 to cause controller 512 to generate the appropriate SPEAKER_FREQUENCY signals so that speaker 513 will produce the appropriate audio tones. Alternatively, the display processor 654 internal to display input/output controller 512 may be configured to automatically generate the appropriate SPEAKER_FREQUENCY signals based on the image generation commands it receives from microprocessor 518. In one version of the invention, an audio tone is generated each time a button or foot switch 44 is depressed in order to provide audio confirmation that the button/switch was depressed. Microprocessor 518 and display processor 654 cooperate to cause the generation of other, distinct audio tones when either new information is presented on the display 37 and/or it is determined that a particular warning needs to be presented to the system user.

Once user update step 810 is executed, microprocessor 518 determines if the user has entered a command indicating user of the selected handpiece is now required, represented in FIG. 23 by motor switch on step 844. In this step, microprocessor 518 reviews the state of the on-off switch of the active handpiece, the appropriate HP_DVC_x signal, and the FS_FWD and FS_RVS signals, to determine if any of these signals is above its hystersis level as specified by the data in the complementary memories. If all of these signal states are below their hystersis, start, levels, microprocessor 518 returns and executes an abbreviated form of the system definition step 804.

In the abbreviated form of step 804, microprocessor reviews the signals presented to it to determine if the state of any of the signals has changed. As part of this review, microprocessor 518 reads the header data contained in the NOVRAMs 72 of the handpieces attached to the control console 36. A comparison revealing that the header data has not changed is interpreted as an indication that the same handpieces are still attached to the control console 36. Changes in the header data are interpreted as an indication that a new handpiece has been attached to the control console 36. If this latter condition exists, microprocessor 518 will read the encyclopedia data for the handpiece.

As part of this abbreviated define system step, microprocessor 518 also reviews what, if any, changes the user has been made to the system 30. Microprocessor 518 receives information regarding these changes in the form of data messages from the display processor 654 that indicate which, if any, buttons presented on display 37 have been actuated. These changes include adjustments of such variables as maximum tool speed, display brightness, and pump speed, the selection of a new handpiece to be active, or the activation of device such as the light bulb 248 of clip 45.

In the described version of the invention, main module 784 further include instructions that cause microprocessor 518 to recognize the continued assertion of the FS_LEFT signal as a result of the depression of footswitch 44c as indication that the pump 40 is to be actuated regardless of the on/off state of the associated handpiece. The continued assertion of the FS_RGHT signals as result of the depression of foot switch 44e is recognized by microprocessor 518 as an indication that the bulb 248 is to be actuated regardless of the on/off state of the complementary handpiece. The short term depressions of switches 44c and 44e are recognized as simple commands to activate the pump and bulb, respectively, with the actuation of the handpiece.

After microprocessor 518 performs the abbreviated define system step 804, similar abbreviated update system and update user steps 806 and 810, respectively, are executed. In the abbreviated update system step 806, microprocessor 518 makes the appropriate adjustments to the data it generates that control the other components of the system 30. For example, if FS_LFT signal was received for an extended period of time, microprocessor 518 will generate the appropriate PUMP_SET_POINT signal so as to cause pump controller 515 to actuate the pump 40. In the update user step 810, microprocessor 508 generates the appropriate commands to the display input/output controller 512 to cause the appropriate images regarding any changes in system state.

When microprocessor loops between steps 804, 806, 810 and 844, in other words no handpiece has been actuated, the system 30 is referred to as being in a user time mode.

If as a result of a review of the HP_DVC_x, FS_FWD and FS_RVS signals during motor switch on step 844, microprocessor 518 determines that surgical personnel want a handpiece to be activated, system 30 transitions from a user time mode to a run time mode. This transition begins with microprocessor, 518 rereading the data in handpiece EEPROM 74 as represented by step 846. The reread of EEPROM 74 is necessary because, as will become clear hereinafter, the data contained therein may have been updated after the initial read of the EEPROM.

After the handpiece EEPROM 74 has been read, microprocessor 518 executes a start motor step 847. In step 847, microprocessor 518 generates the appropriate RESET and ENABLE signals to the motor controller 508 so that correct HIGH _ and LOW_SIDE_CONTROL signals are asserted to cause the initial movement of the motor 52. The time periods for which these signals are asserted are based on the data retrieved from field 442 of NOVRAM 74. The current drawn by motor 52 during the initial phase of its operation is monitored based on the current level data contained in fields 402 and 403 of the NOVRAM 74.

Also as part of the start motor step 847, microprocessor 518 asserts the MOTOR_POWER_ON signal, the MTR_ON/OFF signal and places the FORWARD/REVERSE signal in the appropriate state. Microprocessor 518 also asserts the appropriate HPx_ON signal to close the correct relays 746 or 748 internal to motor driver and current sense circuit 510. Only with the closing of relays 746 or 748 will connections to the control console socket be made that will allow energization signals to be applied to the contacts internal to the associated socket.

After start motor step 847, microprocessor 518 turns on the speed and current set interrupts as represented by step 848. These interrupts cause main module 782 to selectively call speed set module and current set module 788 and 790, respectively, for execution. During the period of time the handpiece 32 or 33 is actuated, the instructions within the speed set module 788, the current set module 790 along with those in a run time module, not illustrated, integral with the main module 782 are executed by microprocessor 518. Once the interrupts are set, microprocessor 518 generates the signals to the other components of control console 36 to cause the appropriate energization signals to be provided to the active, actuated handpiece 32 or 33.

Figures 28, 29:
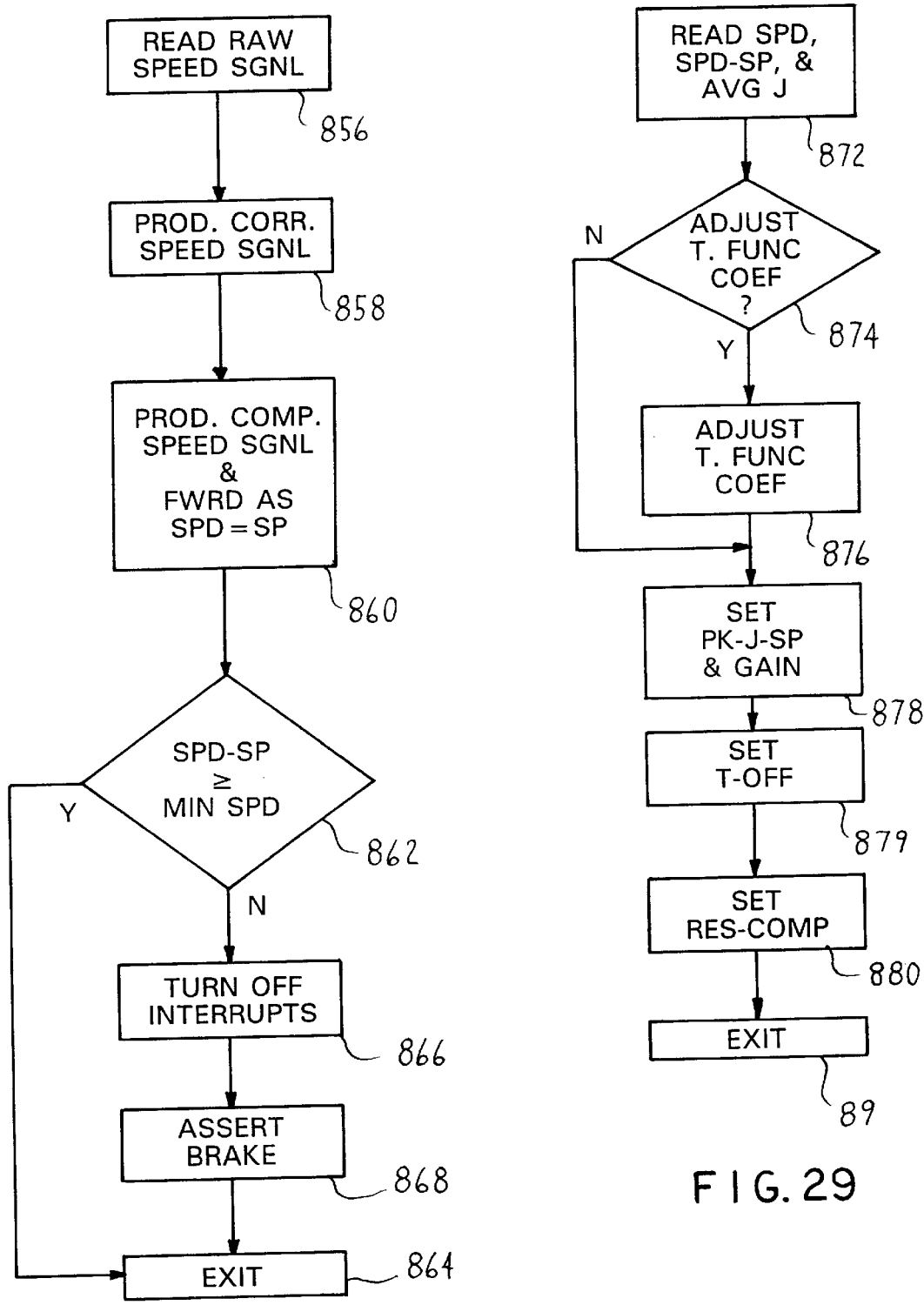
FIG. 28 is a flow chart of the processing steps executed by the microprocessor within the main controller based on the instructions contained within the speed set module.
FIG. 29 is a flow chart of the processing steps executed by the microprocessor within the main controller based on the instructions contained within the current set module.

Once the motor 52 has been initially actuated, a primary signal generated by microprocessor 518 is the SPEED_SET_POINT signal since this is the signal used by motor controller 508 to regulate motor speed. The instructions for establishing the SPEED_SET_POINT signal are contained within speed set module 788. FIG. 28 illustrates the process steps performed by microprocessor 518 based on the instructions contained within this module. The initial step performed by microprocessor 518 is a read raw speed signal step 856. In step 856, microprocessor 518 reads the basic analog signal represented of the user-selected speed for the handpiece. This signal may be the HP_DVC_signal from the sensor 94 in the handpiece that monitors the position of lever arm 186. Alternatively this signal may be either the FS_FWD or FS_RVS switch if the surgeon depressed either foot switches 44a or 44b.

Once the raw speed signal is read, in step 858 microprocessor 518 produces a corrected speed signal. The corrected speed signal is calculated using an established correction function wherein the coefficients of the function are retrieved from the memory associated with the source of the speed signal. Thus, if sensor 94 is the source of the raw sensor signal, the coefficients in fields 372–376 of the handpiece NOVRAM 72 are used as the coefficients of the correction function. If either the FS_FWD or FS_RVS signals are used as the raw speed signal, coefficients retrieved from foot switch assembly memory 392 are used in the correction function.

The corrected speed signal is then used as a variable in a transfer function to produced a adjusted speed signal as represented by step 860. This second compensation of the speed signal is performed in order to minimize any system error so that the resultant SPEED_SET_POINT signal accurately indicates the surgeon desired speed for the handpiece. The relationship established by the transfer function is that when the corrected speed signal indicates that the motor should be operating at the highest possible speed, (either the surgeon set maximum speed or the default maximum speed,) then the motor should actually be running at that speed. In one version of the invention, this transfer function is a first order function. Initially the coefficient of this function is unity. As described hereinafter, as long as the handpiece remains actuated, the microprocessor 518 will continually adjust the coefficient of this function.

As part of adjustment step 860, microprocessor 860 may further adjust the SPEED_SET_POINT signal to prevent the handpiece motor 52 at a rate greater than that specified by the default (NOVRAM) or use-set acceleration/ deceleration rate. In order to perform this step it may be necessary for the microprocessor 518 to compare the user speed to the actual speed of the motor based on the filtered TACHOMETER signal.

The adjusted speed signal produced as a result of the application of the corrected speed signal to the transfer function is then outputted by microprocessor 518 as the SPEED_SET_POINT signal. Motor controller 508 then controls the assertion of the HIGH_ and LOW_SIDE_CONTROL signals based in part on the amplitude of this signal.

Microprocessor 518 then determines if the SPEED_SET_POINT signal indicates that the motor is to be operated below the )minimum, stall, speed as specified from the data retrieved field 388 of NOVRAM 72, represented by step 862. If this comparison indicates that the motor is to be operated above the stall speed, execution of speed set module 788 is terminated as represented by exit step 864.

If, however, the comparison of step 860 indicates that the motor is to be run below the stall speed, microprocessor 518 turns off the speed set and current set interrupts in a step 866. Integral with this step is the zeroing of the SPEED_SET_POINT signal. Microprocessor 518 then asserts an appropriate set of BRAKE signals to motor controller 508 as represented by step 866. Motor controller 508, based on the assertion of the BRAKE signals, causes HIGH_ and LOW_SIDE_CONTROL signals to be actuated that result in the ordered stopping of motor 52. The rate at which microprocessor 518 asserts the BRAKE signals is based on the data retrieved from the brake control field 444 of NOVRAM 72.

Once the brake signals are asserted, microprocessor 518 terminates execution of the instructions within the speed set module 788 as represented by the transition to exit step 864. At this time, the control console leaves the run time mode and returns to the user time mode as represented by step 889 on the flow chart of FIG. 23. The next process step microprocessor then performs is the motor switch on determination step 844.

The above described speed set module 788 is constructed so that SPEED_SET_POINT signal is recalculated and asserted before a determination is made regarding whether or not the user-entered command indicates that the handpiece is to be operated above the minimum stall speed. An advantage of this arrangement is that it ensures prompt generation of a SPEED_SET_POINT signal that accurately represents the user-entered speed command. If the subsequent determination reveals that the user actually has deactuated the handpiece, the relatively short assertion of the low SPEED_SET_POINT signal will not adversely affect the subsequent braking of the handpiece.

The process steps performed by microprocessor 518 based on the execution of current set module are now described by reference to FIG. 29. Initially, microprocessor 518 engages in a read step 872. In read step 872 microprocessor 518 obtains the adjusted speed signal, the surgeon-set or default maximum speed signal, the motor speed and the current drawn by the motor.

It should be understood that this motor speed, as all other motor speed calculations performed by microprocessor 518 is based on the received tachometer signal as filtered by the coefficient contained in tachometer filter field 448 of the handpiece NOVRAM 72. Similarly, this and all other current drawn readings are based on the AVERAGE_I from the motor driver and current sense circuit 508 as filtered by the coefficient contained in current filter field 446.

Once the requisite data is read, microprocessor executes a step 874 to determine if the coefficient of the transfer function used to produce the adjusted speed signal should itself be adjusted. In step 874, a first determination is made regarding whether or not the adjusted speed signal indicates the user has indicated that the motor is to be operated at it highest speed. If the user has made such a command, the current drawn by the motor is compared to current limit in the maximum motor current field 404 of NOVRAM 72. If the drawn current is less than the designated maximum current, microprocessor 518 proceeds to an update transfer function coefficient step 876. If either of these two determinations are negative, step 876 is not executed.

In transfer function coefficient update step 876, the coefficient of the transfer function used to produce the adjusted speed signal in step 860 is updated. More particularly, the coefficient is revised to produce an adjusted speed signal that, assuming the corrected speed signal indicates that the motor is to be run at the maximum speed, will cause the motor to run at the maximum speed. This continual adjustment of the transfer function coefficient serves to minimizes variations in the control of the handpiece owing to the individual variations of the control console 36. Since this updating occurs continually it also compensates for changes in component characteristics within the control console 36 that occur as result of thermal changes in the control console. A more detailed explanation of how this coefficient is updated is found in U.S. Pat. No. 5,543,695, which is incorporated herein by reference.

After step 876, a set PEAK_I_SET_POINT and GAIN signals step 878 is executed. In step 878, microprocessor initially determines the peak current that the motor 52 should draw based on its current speed of operation. This determination is made by first determining the maximum torque the motor should be drawing based on its speed. This maximum torque is determined by reference to the data table containing the representation of the speed/torque plot 438 of FIG. 14. Once the maximum torque is determined, the equivalent maximum current is calculated based on a quadratic equation. The coefficients for this coefficient are those contained with torque-to-current fields 406–410 within the handpiece NOVRAM 72.

Microprocessor 518 then establishes the PEAK_I_SET-POINT and GAIN signals based on the calculated maximum current. If the motor is operating at a relatively high speed such that it should only be drawing relatively small current, microprocessor 518 will generate a relatively low PEAK_I_SET_POINT signal. The complementary GAIN signal will be one that will cause programmable amplifier 756 to significantly amplify the basic current measurement made across resistor 754. In contrast, if the motor is in a state where it is able to develop a relatively large torque, draw a significant current, microprocessor 518 will set the PEAK_I_SET_POINT signal relatively high. The complementary GAIN signal is set so that there will be little, if any amplification of the basic current signal.

Microprocessor 518 then proceeds to execute step 879 in order to set the TIME_OFF signal. This step is performed by reference to the data tables containing the representation of speed/time out plot 808 of FIG. 25. Based on reference to the present speed of the motor and by reference to this data table, microprocessor determines the appropriate time out period for the motor 52 in the event the motor draws a current in excess of that specified by the PEAK_I_SET_POINT signal. A TIME_OUT signal representative of this period is then forwarded to motor controller 508.

Microprocessor then executes a step 880 to establish the state of the RESISTOR_COMPENSATION signal. As discussed with respect to motor controller 508, resistor 721 is selectively connected to the external impedance network of the speed feedback control loop. The tieing of resistor 721 to this network is a function of the speed of the handpiece motor 52.

In one preferred version of this invention, resistor compensation field 450 of handpiece NOVRAM 72 includes two speed settings for the complementary handpiece regarding when resistor 721 should be connected/disconnected to the associated external impedance network. A first one of the speed settings indicates when the resistor should be connected/disconnected as the motor speed is increasing. A second one of the speed setting indicates when the resistor should be connected/disconnected as the motor speed is decreasing. These separate speed settings are not typically not identical. In step 880 microprocessor 518 reviews the current speed of the motor, its past speed and the speed settings contained in field 450. Based on this information, microprocessor 518 asserts and negates the RESISTOR_COMPENSATION as is appropriate. Thus, microprocessor 518 is real time adjusts the external impedance of the speed loop compensation allowing optimal speed loop stability of multiple speeds. This serves to enhance the range c)f speeds over which control console 36 can hold the speed control stable.

The execution of resistor compensation step 880 completes the execution of the instructions contained within current set module 790. Microprocessor then as leaves this module ;as represented by the transition to exit step 882.

When the system 30 is in the run time mode, the run time module of main module 782 is also executed. This sub-module is represented by two steps, steps 886 and 888 depicted on the flow chart of FIG. 23. Step 886 is a run time update system step. In step 886 microprocessor 518 monitors signals representative of state conditions most critical to the operation of the system 30. These signals include: the TACHOMETER signal representative of motor speed; the AVERAGE_I signal; the 40 VDC signal; the HP_CUR signal representative of the bias current drawn by the devices internal to the actuated handpiece; any signal indicating adjustments have been made to the user-setable motor maximum speed, and the DISPLAY_TEMP signal indicating the temperature of display 37. Also during the update system step 886 microprocessor 518 monitors the signals of the devices internal to the actuated handpiece if these signals are not used to established speed control. For example, if one of the devices is the described temperature sensor 96, the complementary HP_DVC_x signal is monitored during the execution of step 886.

Also during step 886, microprocessor 518 responds to the monitored signals as appropriate. For example, if the surgeon has adjusted the maximum speed for the handpiece, the internal maximum speed setting for the main controller 492 are made. If the DISPLAY_TEMP signal indicates a change in display temperature, the appropriate adjustments are made to the CONTRAST and BRIGHTNESS signals in order to maintain a constant image on display 37.

Figure 30:
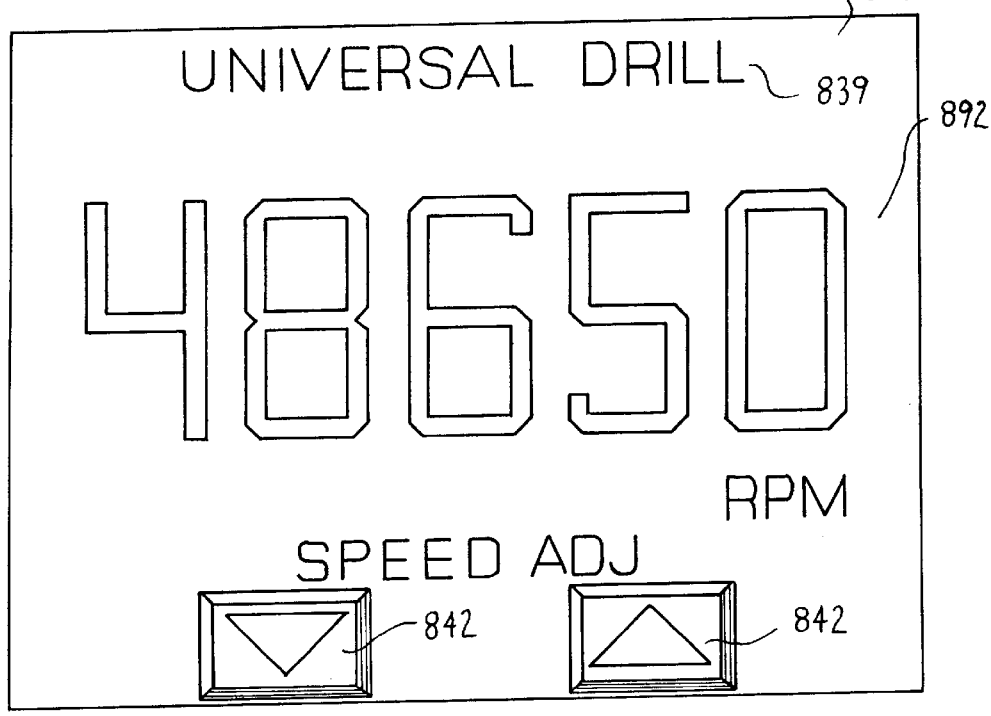
FIG. 30 is an illustration of the run time image presented by the control console when a handpiece is actuated.

Following step 886, microprocessor performs a run time update user step 888. Initially, it should be recognized that as soon as the system 30 transitions from the user time mode to the run time mode, display input/output controller 512 is instructed to switch from presenting the user time image of 812 of FIG. 26 to a run time image 890 now described with respect to FIG. 30. Run time image 890 contains only the information surgeon personnel consider significant when a handpiece is actuated. In the depicted version of image 890, this information is simply the actual speed of the handpiece and the buttons required to adjust the maximum motor speed of the handpiece. As can be seen by reference to FIG. 30, image 890 has a speed presentation 892 that is larger than the maximum speed presentation 840 presented on the user time image 812 and that occupies the substantially the width of the screen. The increase in size of the speed presentation and the elimination of substantially all other images from display 37 minimizes the amount of effort required to read the run time speed of the handpiece.

During execution of the majority of the run time user update steps 888, the primary task of microprocessor 518 is to forward the appropriate command to the display input/output controller to cause the motor speed to be presented in real time. If other signals monitored by microprocessor 518 indicate other component state changes about which the user should be notified, other appropriate commands are sent to the display input/output controller 512. For example, if a HP_DVC_x signal indicates that a handpiece is excessively warming up, microprocessor 518 will instruct display input/output controller 512 to both present an appropriate warning image and generate an appropriate audio warning tone.

The processing steps performed by microprocessor 518 during return to user time mode step 889 will now be discussed in more detail. As part of step 890, microprocessor 518 accesses EEPROM communicator module 786 to write into the handpiece EEPROM 74 data reflecting the new use history of the handpiece. Microprocessor 518 also instructs display input/output controller 512 to stop producing run time image 890 and return to producing user time image 812.

Once system 30 of this invention enters the run time mode, the execution of the run time module steps 886 and 888 are the primary processing steps executed. The execution of the instructions contained within the speed set and current seat modules 788 and 790, respectively, occur as the interrupt executions. It is however, most important that the SPEED_SET_POINT signal be updated as frequently as possibly. Accordingly, in preferred version of the invention, the interrupts are set so that the instructions within speed set module 788 are called for execution every 5 msec. The remaining motor control signals, the PEAK_I_SET_POINT, the GAIN, the TIME_OFF and the RES_COMP signals do not need to be updated as frequently. Accordingly, the interrupts are set so that the instructions within the current set point module 790 are called for execution approximately every 50 msec. Steps 886 and 888 of the run time module do not have to be executed as frequently, these steps are only called for execution once every 150 to 500 msec. In some preferred versions of the invention steps 886 and 888 are executed approximately once every 200 msec.

In order to ensure that the above processing can all take place, in a preferred of the invention it takes approximately 2 msec to execute the instructions contained in speed set module 788, approximately 15 msec to execute the instructions contained in current set module 790 and approximately 60 msec to execute steps 886 and 888 of main module. Collectively, this ensures that once every 200 msec, the SPEED_SET_POINT signal is updated 40 times, the remaining motor control signals are updated four times and the remain system control signals are updated once. This rapid updating of the SPEED_SET_POINT signal assures that the changes in the signal presented to motor controller 508 appear essentially analog.

Figure 31:
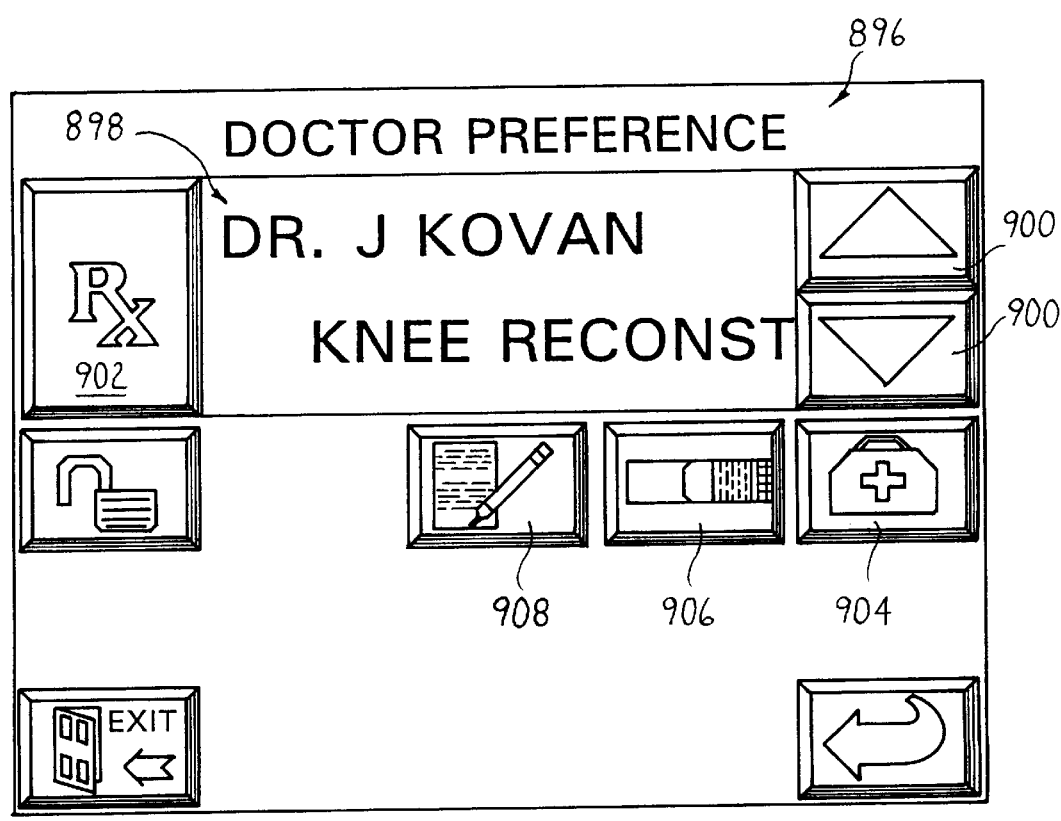
FIG. 31 is an illustration of the surgeon selector image presented by the control console.

As discussed above, one option system 30 allows surgical personnel is to retain an indication of the system settings preferred by individual surgeons for specific medical procedures. This information is stored in display input/output controller EEPROM 662 and is selectively retrieved while the system is in the user time mode. FIG. 31 illustrates a surgeon selector image 896 that is presented on the display 37 based on the depression of options button 838 and other appropriate buttons, not illustrated.

Surgeon selector image 896 includes scroll lines 898 that identify both a specific surgeon and a specific surgical procedure. Buttons 900 to the right of scroll lines 898 are manipulated to present a list of surgeons/surgical procedures stored in the system. A doctor select button 902 to the left of scroll lines 898 is depressed to enter the surgeon preferences for the indicated surgeon/procedure. Once surgeon select button 902 is depressed, microprocessor 518, through display processor 654, retrieves from EEPROM 662 the selected stored settings.

If settings for a new surgeon/procedure are to be entered, a new surgeon 904 button is depressed. The depression of new surgeon button causes a keyboard to be presented on display 37 so that identifying data about the surgeon/procedure can be entered. Then, at the end of the procedure the settings established by the doctor are stored. These settings may be initially stored as part of the return to user time step 889. Button 906 is depressed to erase the record for a particular surgeon/procedure. Button 908 is depressed if there is a need to edit the surgeon/procedure identifier.

Normally, for each surgeon with a stored procedure, after the procedure is again performed, the new settings entered by the doctor are stored. The depression of lock procedure button 910 stops this system from engaging in this automatic rewriting of the stored settings.

The direct drive controller 792 includes the software instructions microprocessor 518 requires to supply energization signals to a handpiece operated in the direct drive mode as opposed to the above described motor drive mode. When these instructions are executed, the commutation cycle of FETs 730 and duty cycle of FETs 732 are controlled directly by microprocessor, independent of any back EMF pulses received as Wx signals. Consequently, it is possible to include in the handpiece a transformer for converting the high voltage (40 VDC) low current (10 Amp) signal produced by the control console into a lower voltage (10 VDC) high current (40 Amp) signal used by some surgical tools. Such conversion is possible by including in direct drive controller module 792 instructions for appropriately regulating the chop and duty cycles established by motor controller 508. The instructions in module 792 would be executed based on appropriate instructional commands stored in NOVRAM 72 for the complementary handpiece.

Thus, when a handpiece is connected to the complementary control console 36 of system 30 of this invention, main processor initially reads the data stored in the handpiece NOVRAM 72 to determine if the handpiece is to be driven in the motor drive mode wherein the drive signals generated based on the state of feedback signals supplied from the motor, the back EMF signals, or in the direct drive mode.

If the handpiece is driven in the motor drive mode, main controller 492 generates the requisite SPEED_SET_POINT, PEAK_I_SET_POINT, GAIN, RES_COMP and TIME_OUT signals the complementary sub assemblies require in order to ensure the proper energization signals are applied to the windings of the motor internal to the handpiece. As long as the motor is developing less than its maximum torque for its given speed, motor controller 508 and motor driver and current sense circuit 510 will assert the correct signals to tie the windings of the motor to the +40 VDC rail 498 and ground. The actual timing of these connections, is further regulated by when the back EMF signals from the motor are received. Proper speed feedback control is maintained by the RESISTOR-COMPENSATION signal regulating the impedance of the external impedance network connected to the speed feedback control loop.

Comparator 692 continually compares the selectively amplified ISENSE signal to the PEAK_I_SET_POINT signal to determine if the torque developed by the motor exceeds its established maximum. If this condition occurs, the output signal from comparator 692 changes state. Motor control chip 686 interprets the change in the state of the comparator signal as a command to negate the assertion of LOW_SIDE_CONTROL signals. The period of time in which the assertion of these signals is to be negated is a function of the TIME_OUT signal.

Control console 36 also monitors the internal temperature of the actuated handpiece. If this temperature exceeds a selected level, an appropriate warning message, and/or override re(quest will be presented on display 37.

The surgical tool system 30 of this invention is configured so that the information regarding the operating parameters of each handpiece is stored within memories 72 and 74 internal to the handpiece. When the system is initialized, the control console 36 reads this data and configures itself to supply the appropriate energization signals to the handpiece. Thus, the system 30 of this invention makes it possible to provide a single control console 36 that can be used to provide energization signals to handpieces with motors that rotate at speeds as low as 10 RPM to speeds as high as 100,000 RPM and that have power requirements that range from as low as 20 Watts to as high as 500 Watts. (This upper limit assumes an appropriate power supply module 494 is attached.) The ability to provide a single control console that can be used to energize such a wide range of instruments eliminates the cost and surgical suite clutter required with having to provide the multiple consoles.

The control console 36 is also configured to not only supply the energization signals required to actuate a motor internal to a handpiece, it can supply direct drive energization signals to a handpiece. This further increases the number and kind of handpieces that can be incorporated into this system 30 so as to further reduce the number of additional control consoles that need to be provided Moreover, the control console 36, by reading the memories 72 and 74 internal to the handpiece, automatically establishes limits regarding the maximum speed at which the handpiece motor should be driven and the current that can be drawn by the handpiece. This eliminates the possibility that, as a result of human error, the control console 36 could be configured so as to result in the application of energization signals that cause the motor to be overdriven or that would allow the handpiece to draw excessive current. Both of the situations could potential cause inadvertent injury to the patient or the hands of the surgeon working with the handpiece.

Still another feature of the system of this invention is that it allows each handpiece to be readily combined with accessory units. A handpiece can, for example be easily fitted with a hand switch 39 and/or a light-and-water clip 45. Both these accessories are completely removable from the handpiece; the handpiece does not have any mounting tabs f:or facilitating accessory attachment. Thus, a single handpiece can be used both by personnel that prefer using a smooth, cylindrical tool and by personnel who prefer working with the accessory attachments. This feature of the invention serves to eliminates the need to provide different handpieces to accommodate the personnel preferences of the surgeons working with the handpiece. This elimination in the need to provide handpieces with different accessories permanently attached thereto further serves to reduce the cost of outfitting a surgical suite.

Furthermore, the removable hand switch 39 of this invention is designed so that slip ring 184 prevents the switch from being fitted over the rear of a handpiece 32 when a cable 43 is coupled thereto. Tab 196 integral with slip ring 184 is dimensioned to prevent the hand switch 39 from being slipped over the forward end of the handpiece 32. These features of the invention thus prevent the hand switch 39 from being fitted to a handpiece while a cable 43 is attached thereto. The cable 43 must be disconnected from the handpiece 32. Thus, if during the process of attaching the hand switch 39, magnet 190 inadvertently comes within close proximity to Hall effect sensor 94, since the handpiece 32 is disconnected from the control console 36, accidental actuation of the handpiece is prevented. In order for the system 30 to operate, the cable 43 must be properly coupled to the handpiece. In order for cable 43 to be so coupled, tab 196 must be seated in complementary slot 185. These features ensure that the hand switch 39 will not fall out of alignment with the handpiece 32 once the system is properly configured.

Moreover, in this invention, the data regarding the characteristics of the output signals asserted by the on/off/speed Hall effect sensors in each handpiece is stored within the handpiece. This makes it possible to use each handpiece with different removable hand switches 39 since the control console 36 can make the necessary signal processing adjustments to adjust for deviations in the magnetic flux of the hand switch magnets 190.

Similarly, the instillation of the memory 329 in the foot switch assembly 46 allows the foot switch assemblies and control consoles 36 to likewise be interchanged.

Still another feature of this invention is that the handpieces can be provided with internal temperature sensors and the NOVRAMs 72 internal to the handpieces contain data regarding the acceptable operating temperatures for the handpieces. This makes it possible to configure the system so that in the event the operating temperature for any of the handpieces exceeds the normal temperature for that specific handpiece, the console will provide a warning statement, reduce the power applied to the handpiece and/or deactivate the handpiece if it becomes excessively warm. This feature of the invention ensures that, if due to use or malfunction, a handpiece becomes excessively heated, there will be little possibility that it will burn the hands of the person holding it. Moreover, as described with respect to handpiece 32, it is possible to provide handpieces of this invention so that the there is a relatively short thermally conductive path between temperature sensor 96 and the windings 58 and front bearing assembly 64 For example, in some versions of the invention temperature sensor 96 is less than 100 mils for windings 58 and more preferably only approximately 20 to 50 mils from the windings. Temperature sensor 96 is likewise less than 500 mils from front bearing assembly 64 and more preferably less than 300 to 400 mils from the bearing assembly. In the event the handpiece 32 is dropped this front bearing assembly 64 may go out of alignment even though such failure is not readily detectable by the operation of the handpiece. As a consequence of this or other failures, windings 58 may rapidly heat. When this bearing assembly is so out of align, the actuation of the handpiece will, however, result in the significant generation of heal: by the windings 58 and/or bearing assembly 64. Owing to the relatively close placement of the temperature sensor 96 to the windings 58 and bearing assembly 64 the sensor will provide a prompt indication to through the control console display 37 that the handpiece is overheating. This will give the personnel using the handpiece some indication of the malfunction before excessive, injury or component failure inducing heat is generated.

The EEPROM 74 internal to the handpiece provides an indication of the total time the handpiece has been actuated. Having the ability to easily obtain this information makes it easy for personnel charged with the maintenance of the handpiece to determine if the handpiece needs to be subjected to a maintenance inspection. The information in EEPROM 74 can also be used by the manufacturer of the handpiece as the basis for determining if a particular handpiece is still under warranty.

The ability of the EEPROM 74 to store data regarding the maximum internal temperature of the handpiece, the highest current drawn by the handpiece and the total power consumed by the handpiece is also useful to persons charged with the maintenance of the handpiece for determining whether or not the handpiece is functioning normally.

The control console 36 of the system 30 of the invention does more than just regulate the operation of handpiece having different energization signal requirements. The control console is further configured to provided integrated control of the accessories, an irrigation pump 40 and an illuminating bulb 248 that are often used in conjunction with a surgical tool. This integrated control eliminates the need to provide an additional controller in the surgical suite.

Still another feature of the control console 36 of this invention is that has three safety switches to prevent power from unintentionally being applied to a handpiece. For the MOTOR_POWER energization signals to be applied from the AC-to-DC converter 494 to a handpiece port, first the MOTOR_POWER_ON signal must be asserted by microprocessor 518. Then, the MOTOR_ON signal must be asserted by the microprocessor 518 to avoid the default negation of the HIGH_SIDE_CONTROL signals by OR gates 698. Finally, even if the FETs 728 are switched on, the MOTOR_POWER signals will only be applied to a handpiece socket if the associated relays 7416 or 748 are closed by the assertion of the requisite HPx_ON signal. This redundancy substantially eliminates the possibility that the control console 36 will inadvertently apply the MOTOR_POWER energization signals to a handpiece.

Still another feature of this invention is that the inductors 740 substantially reduce the magnitude of the current drawn by the FETs 732 as a result of the state transition of FETs 730 and 730. The reduction of this current draw eliminates the need to provide filters in the current sense portion of the motor driver and current sense circuit 510 or software filters in the main controller 492 to compensate for the apparent excessive current draw that would other wise be measured by the current sense circuit.

The control console 36 of the system 30 of this invention is further configured so that the post-excess current drawn time-out period during which the assertion of energization signals to the handpiece is negated is set as part of the process of configuring the control console for use with a handpieces The ability of the motor controller 508 to make this adjustment further enhances the ability to use the control console 36 with handpieces that have different power operating requirements.

Still another feature of this invention is that control console 36 allows a surgeon to rapidly alternate between using a first handpiece and a second handpiece. This facilitates the rapid as possible completion of the surgical procedure. By being able to perform the surgical procedure as quickly as possible, the amount of time the surgical site is open to infection and the patient must be kept anesthetized is likewise lessened. System 30 of this invention also make it possible for the surgeon to set the rates at which the handpiece motor 52 accelerates or decelerates.

It should be recognized that the foregoing description is directed to a specific embodiment of this invention. It will be apparent, however, from the description of the invention that it can be practiced using alternative components other than what has been specifically described. For example, it is clearly not always necessary to provide a handpiece with EEPROM for storing data about events that occur during the operating life of the handpiece. Similarly, it may not always be necessary to provide the non volatile memory internal to the handpiece with all the data provided in the described version of the invention. For example, in some versions of the invention it may be necessary to provide only a minimal amount of data regarding the maximum speed at which the handpiece motor can operate and the maximum current the motor should draw. Alternatively, in some versions of the invention it may be desirable to provide the handpiece memory with data different from what has been described.

Figure 32:
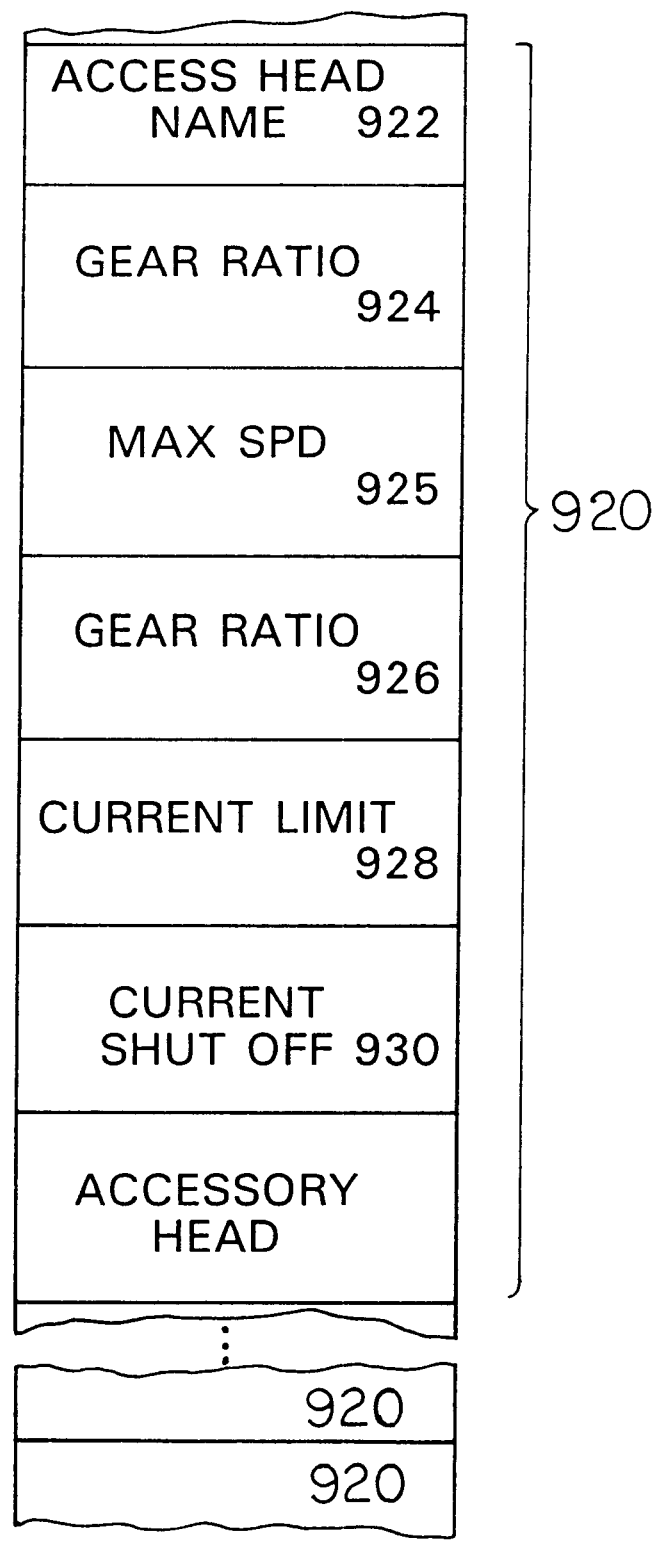
FIG. 32 is a block diagram of a set of accessory head data fields that may be present in the handpiece memory.

For example, as illustrated by FIG. 32, handpiece NOVRAM 72 may be provided with a set of accessory head fields 920. These Fields 920 are provided in a handpiece to which it is necessary to attach a complementary accessory head. This accessory head contains gears and a transmission mechanism necessary for transferring the motive power produced by the motor internal to the handpiece into a form in which it can be used by a cutting accessory attached to the accessory head. Typically these gears reduce the rotational rate of the motor for application to the cutting attachment.

As represented by the first accessory head field 920, each of these fields is composed of a number of sub fields. The first sub field is an accessory head name field 922 that identifies the specific accessory head. The second field is a ratio field 924. Ratio field 924, like gear ratio field 398 indicates the gear ratio for the particular accessory head. A maximum speed field 925 contains information regarding the maximum speed at which the tip of the accessory held can be driven. An increment field 926 contains an indication of the rate at which the user-set maximum speed of the accessory head can be driven. There is also an current limit field 928. Current limit field 928 contains data indicating a correlation between the maximum current the handpiece can draw and the maximum current the accessory head can draw. Typically field 928 contains an indication of the percent of the maximum torque the handpiece can develop, (the current the handpiece can draw). There is also a current shut-off field 930. Current shut-off field 930 contains an indication of the maximum current the handpiece with the particular accessory head attached can draw. If the AVERAGE_I signal indicates the current drawn by the handpiece exceeds the amount specified in current shut-off field 930, microprocessor 518, prevents the further application of energization signals to the handpiece, in some cases by requiring a cold start of the handpiece.

In this version of the invention, during the initial system definition step 804, microprocessor 518 reads the handpiece NOVRAM 72 to determine if it contains any accessory head fields 922. If these fields are absent, microprocessor 518 proceeds to initialize the system 30 as described. If accessory head fields 922 are present, microprocessor !518 instructs display input/output controller 512 to present the retrieved names from the individual accessory head name fields 922 on the initial user time image 812. These names are presented below tool identification line 839 as actuatable buttons. The surgeon using the system is then required to press then appropriate name button to identify the accessory head that is attached to the handpiece. Main controller 492 then regulates the application of energization signals to the handpiece based on the remain data contained in the accessory head sub-fields 924–930 for the selected accessory head.

System 30 may further be configured to provide different, user-selectable control options. For example it may be desirable to configure the system so that the user can first established a fixed speed for the handpiece. Then, the depression of either the hand switch or foot pedal will cause the motor to operate only at the established, fixed speed. Alternatively, it may be desirable to give the option of allowing surgical personnel to reset the hand switch or foot switch controlling the motor from functioning as contact switches that require constant depression in order for the motor to be actuated to single pull switches that can be pressed once to turn the motor on and a second time to turn the motor off.

It should similarly be recognized that the devices installed in a handpiece may be different than what have been described. For example, if a particular handpiece is cauterizing tool, it may be desirable to provide a remote sensor internal to the handpiece that can measure the temperature of the surgical site to which the tool is applied. Similarly, this tool may also be provided with a second temperature sensor that monitors the internal temperature of the tool. In a similar context, it should also be recognized that other handpieces may be provided with none, one, three or more devices each of which assert a signal that is monitored by the control console.

Also, while one specific construction was described, other handpieces could have different structures without departing from the nature of this invention. It may, be desirable to provide to circuit planes inside the handpiece. A first one of the circuit planes could provide the conductive paths to the devices and power consuming members inside the handpiece while the second plane could provide the conductive paths to a removable memory module.

In the described version of the invention the motors 52 internal to the handpieces were described as three-winding brush less, Hapless DC motors. It should be recognized that in other versions of the invention handpieces with different motors may be provided. In these versions of the invention, the motor control and motor drive portions of the control console 36 would be appropriately reconfigured to provide the necessary energization signals to the handpieces. Alternatively, it may be desirable to provide a control console 36 with different motor controllers and motor drivers so that it can be used to provide the different types of energization signals required by different handpieces. Similarly, it is contemplated that different power converter modules 494 can be provided to facilitate the use the surgical tool system 30 of this invention with line voltages of different countries.

As discussed above with regard to the ability of the control console 36 to provide direct drive energization signals, it should be further be recognized that not all handpieces may have direct driven motors internal therewith. The system may be configured so that the control console substitutes as battery pack for a handpiece. Alternatively a handpiece may be some type of device such as a laser or ultrasonic generator or sensor that does not have an internal motor.

It should also be recognized that the control console 36 may have a different configuration that what has been described. For example, some versions of the invention may have parallel or multiple microprocessors that perform the functions of both the main controller 492 and the motor controller 508. Similarly, it may not be necessary to provide the processor internal to the control console 36 with the software tools employed in the described version of the invention. Furthermore, while one particular timing sequence for executing software tools during the actuation of a handpiece was disclosed, in other versions of the invention tool execution may occur at a different rate. For example, it may in some versions of the invention be necessary to execute the software tool that determines if a desired current it being drawn more often than other software tool. Also, the algorithms employed may vary from what has been described.

Moreover, while in the described version of the invention, the control console is described as having a power supply 494 for converting line voltage into voltages useful for energizing components internal to the control console and useful for application to the complementary handpiece, this module may not always be required. It may be possible to provide the control console with a battery pack capable of supplying the power required for energization of the control components and the handpiece. In these versions of the invention, in order to reduce control console size and internal console power draw, the touch screen display and other components such as the pump may be eliminated.

It should also be recognized that the control console 36 can be provided with additional components and/or process instructions so that in, addition to be used with handpieces 32 or 33 provided with NOVRAMs 72 containing data regarding their operating characteristics, it can also can be used with handpieces without such memories. To provide such control it may be necessary to provide one or more additional sockets 505 (FIG. 1) on the face of the console 36 to provide for the cables used with these handpieces. In such a system, main controller 492 is further provided with an additional software module that contains the instructions for providing energization signals to this handpiece. Button 817 presented with user time image 812 (FIG. 26) illustrates one way of selecting this handpiece to be the active handpiece.

It should likewise be understood that the disclosed process steps performed by main controller 492 represent only a single set of such steps that can be performed in one version of this invention. For example, in the described version of the invention, main controller 492 has bee described as basically reading the available data and then asserting or adjusting the associated output signals. This may not always be required. In some versions of the invention, main processor may read some data and immediately act on it. For example, the system could, upon reading the desired pump setting, immediately readjust the complementary PUMP_SET_POINT.

Similarly, the sequence and timing of the processing steps may be different from what has been described. For with the described handpieces the SPEED_SET_POINT signals is that is most frequently updated, there may be some systems or some handpieces for which that is not always the situation. Thus, for some surgical procedures the speed of the handpiece may not be the most critical factor but the torque it develops, the current it draws, may be. For these system/handpieces, the PEAK_I_SET_POINT signal or a CURRENT_SET_POINT signal may be the signal that is most often reset by the main controller 492.

Moreover, some preferred versions of the invention are further configured so that if two handpieces, both with hand switches 39 attached to control console 36, and one hand switch is depressed, the control console will automatically designated the associated handpiece as the active, actuated handpiece. If both hand switches 39 are depressed, the first one to send a signal to the console 36 locks out the switch signal from the other handpiece. In these versions of the invention microprocessor 518 is configured so that when in the user time mode, it cycles the HP_1/2 to periodically pole the HP_DVC_x_x signals that could potentially generate the switch signals. The control console 36 typically does not present any message to the user on display 37 to indicate that this poling is occurring.

It should likewise be recognized that the images presented on the display 37 can vary from what has been described. As previously discussed, the handpiece NOVRAM 72 can store data regarding any custom image that needs to be presented during its operation. Alternatively, user time and run time images only slightly different from what has been illustrated may be presented. For example, for some handpieces it may be desirable to prevent a graphical indication of the speed at which the handpiece is operating. This presentation may also be a matter of physician preference. For still other handpieces, it may be desirable or optional to, in addition to presenting an indication of handpiece speed, further present an indication of the torque developed by the handpiece. For both these options, it is still anticipated that the run time images presenting this information will be larger in size than the initial image presented as the user time image.

Therefore, it is an object of the appended claims to cover all such modifications and variations as come within the true spirit and, scope of the invention.

The embodiments of the invention in which an exclusive property or privilege is claimed are defined as follows:

1. A surgical handpiece, said surgical handpiece including:
   a housing having opposed front and rear ends;
   an electrical power consuming unit located within said housing, said power consuming unit being configured to receive energization signals;
   a surgical attachment designed for application to a surgical site that is connected to said power consuming unit for actuation by said power consuming unit;
   a removable switch assembly, said switch assembly including a collar adapted to be releasable fitted to said housing and a switch lever movably secured to said collar; and
   a sensor disposed in said housing, said sensor configured to generate a sensor signal representative of the position of said switch lever of said switch assembly relative to said sensor.

2. The surgical handpiece of claim 1, further including a tab formed integrally with said collar of said switch assembly, said tab positioned to prevent said collar from being fitted over said front end of said housing.

3. The surgical handpiece of claim 1, wherein said switch lever is pivotally mounted to said collar so that one end of said switch lever will move towards and away from said housing.

4. The surgical handpiece of claim 1, wherein: a magnet is disposed in said switch lever of said switch assembly and said sensor is configured to monitor magnetic fields produced by said magnet.

5. The surgical handpiece of claim 1, wherein said electrical power consuming unit is a motor.

6. A powered surgical tool system, said system including:
   a powered surgical handpiece for actuating an attachment, said handpiece having a variable speed motor for actuating the attachment, wherein said motor is actuated by an energization signal;
   a manually actuatable switch for regulating the speed of said motor, said switch generating a control signal;
   a non-volatile memory integral with said handpiece, said memory containing data representative of the maximum current for said motor at a plurality of different speeds; and
   a control console connected to said handpiece for applying energization signals to said motor and connected to said memory for reading the data from said memory, said control console being configured to:
   monitor the speed of said motor;
   monitor the current drawn by said motor;
   apply the energization signals to said motor based on the control signal and the speed of said motor;
   calculate a maximum allowed current to be drawn by said motor based on the speed of said motor and the data in said memory representative of the maximum current for said motor at a plurality of speeds;
   compare the current drawn by said motor to the maximum allowed current; and
   when the comparison of the current drawn by the motor to maximum allowed current indicates said motor is drawing more current than the maximum allowed current, modulating the application of energization signals to said motor.

7. The powered surgical tool system of claim 6, wherein:
   said memory includes a first set of data fields that contain data indicating the maximum torque of said motor for a plurality of different motor speeds and a second set of data fields that contain the coefficients of a torque-to-current relationship for said motor; and
   said control console is configured to calculate the maximum allowed current for said motor by:
   determining a maximum allowed torque for said motor based on the speed of said motor and the data in said memory indicating the maximum torque of said motor; and
   calculating the maximum allowed current for said motor based on the maximum allowed torque of said motor and the coefficients of the torque-to-current relationship for said motor.

8. The powered surgical tool system of claim 6, wherein:
   said switch includes a control member located outside of said handpiece and a switch sensor located in said handpiece, wherein said control member is movable relative to said switch sensor and said switch sensor generates the control signal as a function of the relative position of said control member to said switch sensor; and
   said memory includes a set of coefficients for correcting the control signal; and
   said control console is further configured to:
   produce a corrected control signal based on the control signal from said switch sensor and the coefficients for correcting the control signal; and
   apply energization signals to said motor based on the corrected control signal and the speed of the motor.

9. The powered surgical tool system of claim 6, wherein said memory is disposed in said handpiece.

10. A powered surgical tool system, said system including:
    a powered surgical handpiece for actuating an attachment, said handpiece having a variable speed motor for actuating the attachment, wherein said motor is actuated by an energization signal;
    a manually actuated switch assembly for indicating a speed at which said motor is to be operated, said switch assembly having state sensor that generates a variable control signal that indicates the speed at which said motor is to be operated, wherein said state sensor is located in said handpiece or in a supplemental component separate from said handpiece;
    a non-volatile memory integral with said handpiece, said memory containing data indicating if said state sensor is located in said handpiece; and a control console connected to said handpiece for applying energization signals to said motor and connected to said memory for reading the data therein, said control console being configured to:
  read the data from said memory;
  if the data in said memory indicates said state sensor is in said handpiece, retrieve from said handpiece the control signal;
  if the data in said memory indicates said state sensor is not in said handpiece, retrieve from the supplemental component the control signal;
  monitor the speed of said motor; and
  generate the energization signals to said motor based on the speed of said motor and the control signal.

11. The powered surgical tool system of claim 10, wherein:
  a foot switch assembly is selectively connected to said control console, said foot switch assembly having an auxiliary state sensor that generates the control signal; and
  said control console is further configured to:
    determine if said foot switch assembly is connected to said control console; and
    if said foot switch assembly is connected to said control console, to generate the energization signals to said motor based on the control signals from said auxiliary state sensor regardless of the presence of said state sensor in said handpiece.

12. The surgical tool system of claim 10, wherein said memory is disposed in said handpiece.

13. A powered surgical tool for actuating an attachment, said tool including:
  a handpiece having a variable speed motor for actuating the attachment, wherein said motor is actuated by an energization signal and a coupling assembly for releasable connecting the attachment to said motor; and
  a non-volatile memory integral with said handpiece, said memory having therein data describing the characteristics of the energization signal to be applied to said motor, said memory including data indicating, for a plurality of distinct speeds, the maximum current said motor is allowed to draw.

14. The powered surgical tool of claim 13, wherein said memory includes a first set of data fields that contain data indicating the maximum torque of said motor for a plurality of different speeds and a second set of data fields that contain the coefficients of a torque-to-current relationship for said motor.

15. The powered surgical tool of claim 13, wherein said memory further includes data indicating whether or not an auxiliary sensor is fitted to said handpiece, said auxiliary sensor producing an output signal, and, if said auxiliary sensor is fitted to said handpiece, data indicating the type of output signals produced by said auxiliary sensor.

16. The powered surgical tool of claim 13, wherein said memory is disposed in said handpiece.

17. A powered surgical tool for actuating an attachment, said tool including:
  a handpiece having a power producing unit for actuating the attachment, wherein said power producing unit is actuated by an energization signal and a coupling assembly for releasably connecting the attachment to said power producing unit;
  a first sensor disposed in said handpiece wherein said first sensor is one from a plurality of different types of sensor and said first sensor produces a specific type of output signal as function of the type of the sensor;
  a non-volatile memory integral with said handpiece, said memory having therein data descriptive of the energization signals to be applied to said power producing unit and data that describes the type of output signal produced by said first sensor.

18. The powered surgical tool of claim 17, wherein said memory further includes data defining coefficients that are used by a processor separate from said handpiece to produce a corrected output signal from the output signal produced by said first sensor.

19. The powered surgical tool of claim 17, wherein said first sensor is part of a switch assembly used to control actuation of said power producing unit, said switch assembly having a manually-actuated member and said first sensor is configured to produce the output signal based on actuation of the manually-actuated member.

20. The powered surgical tool of claim 19, wherein said switch assembly includes a member that is moved relative to said first sensor and said first sensor is configured to produce the output signal as a function of the distance of said member to said first sensor.

21. The powered surgical tool of claim 17, wherein said first sensor is configured to monitor operation of said handpiece and said first sensor produces the output signal as a function of the operating state of said handpiece monitored by said first sensor.

22. The powered surgical tool of claim 21, wherein said first sensor is a temperature sensor configured to monitor the temperature of said handpiece and is configured to produce the output signal as a function of the temperature of said handpiece.

23. The powered surgical tool of claim 17, wherein:
  a second sensor separate from said first sensor is disposed in said handpiece, said second sensor being one from the plurality of different types of sensors and said second sensor produces an output signal wherein the output signal of said second sensor is different from the output signal produced by said first sensor; and
  said memory further includes data that describes the type of output signal produced by said second sensor.

24. The powered surgical tool of claim 23 wherein:
  said first sensor is part of a switch assembly used to control actuation of said handpiece wherein the output signal produced by said first sensor is a function of a manually actuated switch member; and
  said second sensor is configured to monitor operation of said handpiece and said second sensor produces the output signal as a function of the operating state of said handpiece monitored by the said second sensor.

25. The powered surgical tool of claim 17, wherein said memory is seated in said handpiece.

26. A powered surgical tool for actuating an attachment, said tool including:
  a handpiece having a power consuming unit for actuating the attachment, wherein said power consuming unit is actuated by an energization signal and a coupling assembly for releasable connecting the attachment to said power consuming unit;
  a sensor disposed in said handpiece wherein said sensor generates an output signal used to control or monitor the operation of said power consuming unit; and
  a non-volatile memory integral with said handpiece, said memory having therein data descriptive of the energization signals to be applied to said power consuming unit and data defining coefficients that are used by a processor remote from said handpiece to define a corrected output signal based on the output signal produced by said sensor.

27. The powered surgical tool of claim 26, wherein:
a switch assembly is attached to said handpiece, said switch assembly including a lever that is positioned to move relative to said sensor and wherein said sensor is part of said switch assembly and is configured to vary the output signal produced thereby as a function of the relative distance of said lever to said sensor.

28. The powered surgical tool of claim 17, wherein said lever is removably secured to said handpiece.

29. The powered surgical tool of claim 26, wherein said sensor a temperature sensor is configured to vary the output signal produced thereby as a function of the internal temperature of said handpiece.

30. The powered surgical tool of claim 26, wherein said memory is seated in said handpiece.

31. A powered surgical tool system, said system including:
a handpiece having a power producing unit for actuating an attachment, wherein said power producing unit is actuated by an energization signal and a coupling assembly for releasably connecting the attachment to said power producing unit;
a sensor disposed in said handpiece wherein said sensor generates a sensor output signal used to control or monitor the operation of said power producing unit;
a non-volatile memory integral with said handpiece, said memory having therein data descriptive of the energization signals to be applied to said power producing unit and data defining coefficients for producing a corrected sensor output signal based on the sensor output signal; and
a control console connected to: said handpiece for applying energization signals to said power producing unit; said sensor for receiving the sensor output signal; and to said memory for reading the data stored therein, said control console configured to:
produce a corrected sensor output signal based on the sensor output signal and the coefficient data in said memory; and
selectively apply energization signals to said power producing unit based on the corrected sensor output signal.

32. The powered surgical tool system of claim 31, wherein:
said sensor is one from a plurality of different types of sensors and the sensor output signal produced by said sensor is one from a plurality of different types of sensor output signals;
said memory further includes data indicating the type of the sensor output signal produced by said sensor; and
said control console is further configured to:
determine from the data in said memory the type of the sensor output signal produced by said sensor; and
based on the determination of the type of the sensor output signal, engage in one of a plurality of different control sequences for regulating the generation of the energization of said power producing unit based on the corrected output signal.

33. The powered surgical tool system of claim 32, wherein:
a switch assembly is attached to said handpiece to control actuation of said power producing unit, said switch assembly having a manually-actuated member and said sensor forms part of said switch assembly wherein the sensor output signal is based on the actuation of said manually-actuated member;
said memory contains data indicating that said sensor output signal represents the user-selected actuation of said power producing unit; and
said control console, upon reading the data in said memory, applies energization signals to said power producing unit based on the corrected sensor output signal.

34. The powered surgical tool system of claim 32, wherein:
said sensor monitors operation of said handpiece and the sensor output signal produced by said sensor is representative of the operating state monitored by said sensor;
said memory includes data indicating the type of operating state information represented by said sensor output signal and an operating limit for said handpiece;
said control console, upon reading the data in said memory, compares the corrected sensor output signal to the operating limit and, when the comparison indicates that the operating state of said handpiece exceeds the operating limit, selectively modulates the application of the energization signals to said power producing unit.

35. The powered surgical tool system of claim 34, wherein said memory is located in said handpiece.

36. A powered surgical handpiece comprising:
a housing;
a variable-speed motor disposed in said housing, said motor being actuated by energization signals;
a coupling assembly attached to said housing for releasably coupling a cutting attachment to said motor; and
a memory integrally associated with said motor, said memory containing data describing the energization signals that are to be applied to said motor, data describing whether or not a sensor is present in said housing that produces an output signal for controlling the motor or monitoring the operating state of the handpiece, and, if the sensor is present, data describing the type of the sensor output signal and any coefficients required to produce a corrected sensor output signal.

37. The powered surgical handpiece of claim 36, wherein said memory is located in said housing.

* * * * *

UNITED STATES PATENT AND TRADEMARK OFFICE
CERTIFICATE OF CORRECTION

PATENT NO.   : 6,017,354
DATED        : January 25, 2000
INVENTOR(S)  : Jerry A. Culp et al.

It is certified that error appears in the above-identified patent and that said Letters Patent is hereby corrected as shown below:

Column 61,
Lines 35 & 36, change "releasable" to -- releasably --.

Column 64,
Line 4, after "energization" insert -- signals --.
Line 5, after "corrected" insert -- sensor --.

Signed and Sealed this

Sixth Day of November, 2001

*Attest:*

*Nicholas P. Godici*

NICHOLAS P. GODICI
*Attesting Officer*   *Acting Director of the United States Patent and Trademark Office*